US010899800B2

(12) United States Patent
Langedijk et al.

(10) Patent No.: US 10,899,800 B2
(45) Date of Patent: *Jan. 26, 2021

(54) STABILIZED SOLUBLE PRE-FUSION RSV F POLYPEPTIDES

(71) Applicant: Janssen Vaccines & Prevention B.V., Leiden (NL)

(72) Inventors: Johannes Petrus Maria Langedijk, Leiden (NL); Anders Krarup, Leiden (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 381 days.

This patent is subject to a terminal disclaimer.

(21) Appl. No.: 14/786,955

(22) PCT Filed: Apr. 24, 2014

(86) PCT No.: PCT/EP2014/058353
§ 371 (c)(1),
(2) Date: Oct. 23, 2015

(87) PCT Pub. No.: WO2014/174018
PCT Pub. Date: Oct. 30, 2014

(65) Prior Publication Data
US 2016/0102123 A1 Apr. 14, 2016

(30) Foreign Application Priority Data
Apr. 25, 2013 (EP) .................................... 13165402

(51) Int. Cl.
*C07K 14/005* (2006.01)
*A61K 39/155* (2006.01)
*C07K 14/135* (2006.01)
*A61K 39/12* (2006.01)
*C12N 7/00* (2006.01)
*A61K 39/00* (2006.01)

(52) U.S. Cl.
CPC ............ *C07K 14/005* (2013.01); *A61K 39/12* (2013.01); *A61K 39/155* (2013.01); *C07K 14/135* (2013.01); *C12N 7/00* (2013.01); *A61K 39/00* (2013.01); *A61K 2039/55561* (2013.01); *C07K 2319/00* (2013.01); *C07K 2319/70* (2013.01); *C07K 2319/73* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| 4,235,877 | A | 11/1980 | Fullerton |
|---|---|---|---|
| 4,372,945 | A | 2/1983 | Likhite |
| 4,474,757 | A | 10/1984 | Arnon et al. |
| 5,057,540 | A | 10/1991 | Kensil et al. |
| 5,122,458 | A | 6/1992 | Post et al. |
| 5,385,839 | A | 1/1995 | Stinski |
| 5,559,099 | A | 9/1996 | Wickham et al. |
| 5,837,511 | A | 11/1998 | Falck-Pedersen et al. |
| 5,837,520 | A | 11/1998 | Shabram et al. |
| 5,846,782 | A | 12/1998 | Wickham et al. |
| 5,851,806 | A | 12/1998 | Kovesdi et al. |
| 5,891,690 | A | 4/1999 | Massie |
| 5,965,541 | A | 10/1999 | Wickham et al. |
| 5,981,225 | A | 11/1999 | Kochanek et al. |
| 5,994,106 | A | 11/1999 | Kovesdi et al. |
| 5,994,128 | A | 11/1999 | Fallaux et al. |
| 6,020,191 | A | 2/2000 | Scaria et al. |
| 6,040,174 | A | 3/2000 | Imler et al. |
| 6,083,716 | A | 7/2000 | Wilson et al. |
| 6,113,913 | A | 9/2000 | Brough et al. |
| 6,225,289 | B1 | 5/2001 | Kovesdi et al. |
| 6,261,823 | B1 | 7/2001 | Tang et al. |
| 6,485,958 | B2 | 11/2002 | Blanche et al. |
| 7,270,811 | B2 | 9/2007 | Bout et al. |
| 7,326,555 | B2 | 2/2008 | Konz, Jr. et al. |
| 8,772,256 | B2 | 7/2014 | Graham et al. |
| 8,932,607 | B2 | 1/2015 | Custers et al. |
| 2011/0305727 | A1 | 12/2011 | Swanson et al. |
| 2012/0164176 | A1 | 6/2012 | Swanson et al. |
| 2012/0315270 | A1 | 12/2012 | McLellan et al. |
| 2013/0177573 | A1 | 7/2013 | Williamson et al. |
| 2013/0315270 | A1 | 11/2013 | Kumazaki et al. |
| 2014/0073032 | A1 | 3/2014 | Custers et al. |
| 2014/0248314 | A1 | 9/2014 | Swanson et al. |

(Continued)

FOREIGN PATENT DOCUMENTS

| EP | 0853660 | A1 | 7/1998 |
|---|---|---|---|
| EP | 1230354 | A | 8/2002 |

(Continued)

OTHER PUBLICATIONS

McLellan et al., "Structural Basis of Respiratory Syncytial Virus Neutralization by Motavizumab," Nature Structural & Molecular Biology, vol. 17, pp. 248-250 (2010).
Swanson et al., "Structural Basis for Immunization with Postfusion Respiratory Syncytial Virus Fusion F Glycoprotein (RSV F) to Elicit High Neutralizing Antibody Titers," PNAS, vol. 108, pp. 9619-9624 (2011).
Letarov et al., "The Carboxy-Terminal Domain Initiates Trimerization of Bacteriophage T4 Fibritin," Biochemistry (Moscow), vol. 64, No. 7, pp. 817-823 (1999).
Guthe et al., "Very Fast Folding and Association of a Trimerization Domain from Bacteriophage T4 Fibritin," J. Mol. Biol., vol. 337, pp. 905-915 (2004).

(Continued)

Primary Examiner — Shanon A. Foley
Assistant Examiner — Myron G Hill
(74) Attorney, Agent, or Firm — Ice Miller LLP

(57) ABSTRACT

Described are stable pre-fusion respiratory syncitial virus (RSV) F polypeptides, immunogenic compositions comprising the polypeptides and uses thereof for the prevention and/or treatment of RSV infection.

38 Claims, 12 Drawing Sheets
Specification includes a Sequence Listing.

(56) References Cited

U.S. PATENT DOCUMENTS

| | | | |
|---|---|---|---|
| 2014/0271699 A1* | 9/2014 | Kwong | C07K 14/005 424/187.1 |
| 2016/0102123 A1 | 4/2016 | Langedijk et al. | |
| 2016/0145321 A1 | 5/2016 | Wadia et al. | |
| 2016/0145322 A1 | 5/2016 | Wadia et al. | |
| 2016/0176932 A1 | 6/2016 | Langedijk et al. | |

FOREIGN PATENT DOCUMENTS

| | | |
|---|---|---|
| WO | 9003184 | 4/1990 |
| WO | 9014837 | 12/1990 |
| WO | 9609378 | 3/1996 |
| WO | 9611711 | 4/1996 |
| WO | 98/22588 A2 | 5/1998 |
| WO | 98/39411 A1 | 9/1998 |
| WO | 99/12568 A1 | 3/1999 |
| WO | 99/41416 A2 | 8/1999 |
| WO | 00/29024 A1 | 5/2000 |
| WO | 00/32754 A1 | 6/2000 |
| WO | 2000/70071 A1 | 11/2000 |
| WO | 01/66137 A1 | 9/2001 |
| WO | 2001085984 A1 | 11/2001 |
| WO | 02/40665 A2 | 5/2002 |
| WO | 03040178 A1 | 5/2003 |
| WO | 03/049763 A1 | 6/2003 |
| WO | 03/061708 A1 | 7/2003 |
| WO | 03/078592 A2 | 9/2003 |
| WO | 2003/104467 A1 | 12/2003 |
| WO | 2004001032 A2 | 12/2003 |
| WO | 2004004762 | 1/2004 |
| WO | 04/020971 A2 | 3/2004 |
| WO | 2005002620 | 1/2005 |
| WO | 2005071093 A2 | 8/2005 |
| WO | 2005/080556 A2 | 9/2005 |
| WO | 06/108707 A1 | 10/2006 |
| WO | 2007104792 A2 | 9/2007 |
| WO | 07/110409 A1 | 10/2007 |
| WO | 2009/11713 A1 | 1/2009 |
| WO | 2009079796 | 7/2009 |
| WO | 10/060719 A1 | 6/2010 |
| WO | 2010086189 A2 | 8/2010 |
| WO | 2010149743 | 12/2010 |
| WO | 2010149745 | 12/2010 |
| WO | 2011008974 | 1/2011 |
| WO | 2011/020079 A1 | 2/2011 |
| WO | 11/045378 A1 | 4/2011 |
| WO | 11/045381 A1 | 4/2011 |
| WO | 2011050168 | 4/2011 |
| WO | 11/098592 A1 | 8/2011 |
| WO | 2012006596 | 1/2012 |
| WO | 2012158613 | 11/2012 |
| WO | 13/135615 A1 | 9/2013 |
| WO | 2013/139911 A1 | 9/2013 |
| WO | 2013/139916 A1 | 9/2013 |
| WO | 2014005643 A1 | 1/2014 |
| WO | 2014160463 A1 | 10/2014 |
| WO | 2014174018 | 10/2014 |
| WO | 2014202570 A1 | 12/2014 |
| WO | 2015013551 A1 | 1/2015 |
| WO | 2015040002 A1 | 3/2015 |
| WO | 2017174564 A1 | 10/2017 |

OTHER PUBLICATIONS

"Database UniProt Accession W8CJC7," http://ibis.internal.epo.org/exam/dbfetch.jsp?id=UNIPROT:W8CJC7, Download date: Aug. 12, 2015, 1 page.

Widjaja et al., "Recombinant soluble Respiratory Syncytial Virus F Protein That Lacks Heptad Repeat B, Contains a GCN4 Trimerization Motif and is Not Cleaved Displays Prefusion-Like Characteristics," PLOS ONE, 20 pages, Jun. 24, 2015.

Written Opinion dated Oct. 10, 2016 in Int'l Application No. PCT/EP2016/066104.

Int'l Search Report dated Oct. 10, 2016 in Int'l Application No. PCT/EP2016/066104.

Written Opinion dated Oct. 12, 2016 in Int'l Application No. PCT/EP2016/066098.

Int'l Search Report dated Oct. 12, 2016 in Int'l Application No. PCT/EP2016/066098.

Suzuki et al., "An Isoleucine Zipper Peptide Forms a Native-like Triple Stranded Coiled Coil in Solution," Protein Engineering, vol. 11, No. 11, pp. 1051-1055 (1998).

Dames et al., "NMR Structure of a Parallel Homotrimeric Coiled Coil," Nature Structural Biology, vol. 5, No. 8, pp. 687-691 (Aug. 1998).

Calder et al., "Electron Microscopy of the Human Respiratory Syncytial Virus Fusion Protein and Complexes That it Forms With Monoclonal Antibodies," Virology, vol. 271, pp. 122-131 (2000).

Harbury et al., "A Switch Between Two-, Three-, and Four-Stranded Coiled Coils in GCN4 Leucine Zipper Mutants," Science, vol. 262, pp. 1401-1407.

O'Shea et al., "Evidence That the Leucine Zipper is a Coiled Coil," Science, vol. 243, pp. 538-542 (Jan. 27, 1989).

Database EMBL, Aug. 28, 1995, Human respiratory syncytial virus, strain RSB89-1734, fusion protein (F) mRNA, complete CDS, XP002729919.

Int'l Search Report and Written Opinion dated Oct. 9, 2014 in Int'l Application No. PCT/EP2014/062655.

PCT International Search Report, dated Aug. 12, 2014, PCT/EP2014/058353.

PCT Written Opinion of International Searching Authority, dated Aug. 12, 2014, PCT/EP2014/058353.

Magro et al., Neutralizing antibodies against the preactive form of respiratory syncytial virus fusion protein offer unique possibilities for clinical intervention, Proceedings of the National Academy of Sciences, Feb. 21, 2012, pp. 3089-3094, vol. 109, No. 8.

Yin et al., Structure of the parainfluenza virus 5 F protein in its metastable, prefusion conformation, Nature, Jan. 1, 2006, pp. 38-44, vol. 439, No. 7072.

McLellan et al., Structure of RSV Fusion Glycoprotein Bound to a Prefusion-Specific Neutralizing Antibody, Science, Apr. 25, 2013, pp. 1113-1117, vol. 340, No. 6136.

McLellan et al., Structure-Based Design of a Fusion Glycoprotein Vaccine for Respiratory Syncytial Virus, Science, Oct. 31, 2013, pp. 592-598, vol. 342, No. 6158.

Ngwuta et al, "Prefusion F-Specific Antibodies Determine the Magnitude of RSV Neutralizing Activity in Human Sera," Science Translational Medicine, vol. 7, No. 309, pp. 1-9 (2015).

Int'l Search Report and Written Opinion dated Jun. 12, 2017 in Int'l Application No. PCT/EP2017/057962.

Abbink et al, "Comparative Seroprevalence and Immunogenicity of Six Rare Serotype Recombinant Adenovirus Vaccine Vectors from Subgroups B and D," Journal of Virology, vol. 81, No. 9, pp. 4654-4663 (May 2007).

Abrahamsen et al, "Construction of an Adenovirus Type 7a E1A-Vector," Journal of Virology, vol. 71, No. 11, pp. 3946-8951 (Nov. 1997).

Altaras et al, "Production and Formulation of Adenovirus Vectors," Advances in Biochemical Engineering / Biotechnology, vol. 99, pp. 193-260 (2005).

Brough et al, "A Gene Transfer Vector-Cell Line System for Complete Functional Complementation of Adenovirus Early Regions E1 and E4," Journal of Virology, vol. 70, No. 9, pp. 6497-6501 (Sep. 1996).

Fallaux et al, "New Helper Cells and Matched Early Region 1-Deleted Adenovirus Vectors Prevent Generation of Replication-Competent Adenoviruses," Human Gene Therapy, vol. 9, pp. 1909-1917 (Sep. 1998).

Gao et al, "A Cell Line for High-Yield Production of E1-Deleted Adenovirus Vectors without the Emergence of Replication-Competent Virus," Human Gene Therapy, vol. 11, pp. 213-219 (Jan. 2000).

Goerke et al, " Development of a Novel Adenovirus Purification Process Utilizing Selective Precipitation of Cellular DNA," Biotechnology and Bioengineering, vol. 91, pp. 12-21 (2005).

(56) References Cited

OTHER PUBLICATIONS

Havenga et al, "Novel replication-incompetent adenoviral B-group vectors: high vector stability and yield in PER.C6 mils," Journal of General Virology, vol. 87, pp. 2135-2143 (2006).
Hoganson et al, "Development of a Stable Adenoviral Vector Formulation," BioProcessing Journal, vol. 1, No. 1, pp. 43-48 (Mar. 2002).
Kim et al, "Single mucosal immunization of recombinant adenovirus-based vaccine expressing F1 protein fragment induces protective mucosal immunity against respiratory syncytial virus infection," Vaccine, vol. 28, pp. 3801-3808 (2010).
Kohlmann et al, "Protective Efficacy and Immunology of an Adenoviral Vector Vaccine Encoding the Codon-Optimized F Protein of Respiratory Syncytial Virus," Journal of Virology, vol. 83, No. 23, pp. 12601-12610 (Dec. 2009).
Konz et al, "Serotype Specificity of Adenovirus Purification Using Anion-Exchange Chromatography," Human Gene Therapy, vol. 16, pp. 1346-1353 (Nov. 2005).
Konz et al, "Scaleable Purification of Adenovirus Vectors," Methods in Molecular Biology, vol. 434, No. 2, pp. 13-23 (2008).
Krarup et al, "A Highly Stable Prefusion RSV F Vaccine Derived from Structural Analysis of the Fusion Mechanism," Nature Communications, vol. 6, pp. 1-11 (Sep. 2015).
Nan et al, "Development of an Ad7 cosmid system and generation of an Ad7LE1LE3HIVMN env/rev recombinant virus," Gene Therapy, vol. 10, pp. 326-336 (2003).
Pemberton et al, "Cytoxic T Cell Specificity for Respiratory Syncytial Virus Proteins: Fusion Protein is an Important Target Antigen," Journal of General Virology, vol. 68, pp. 2177-2182 (1987).
Solabomi et al, "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, pp. 3817-3823 (Aug. 2008).
Vogels et al, "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 3263-8271 (Aug. 2003).
Yu et al, "Single Intranasal Immunization with Recombinant Adenovirus-Based Vaccine Induces Protective Immunity against Respiratory Syncytial Virus Infection," Journal of Virology, vol. 82, No. 5, pp. 2350-2357 (Mar. 2008).
Int'l Search Report and Written Opinion dated Jun. 12, 2017 in Int'l Application No. PCT/EP2017/057957.
Krause et al, "A Broadly Neutralizing Human Monclonal Antibody That Recognizes a Conserved, Novel Epitope on the Globular Head of the Influenza H1N1 Virus Hemagglutinin," Journal of Virology, vol. 85, No. 20, pp. 10905-10908 (Oct. 2011).
McLellan et al, "Structure of Respiratory Syncytial Virus Fusion Glycoprotein in the Postfusion Conformation Reveals Preservation of Neutralizing Epitopes," Journal of Virology, vol. 85, No. 15, pp. 7788-7796 (Aug. 2011).
Database Geneseq (online) "RSV fusion protein N67I S215P, RSV CL57-v224, fibritin, SEQ: 74", XP002761983, retrieved from EBI accession No. GSP:BBP75438, Database accession No. BBP75438 sequence.

Neuzil, "Progress toward a Respiratory Syncytial Virus Vaccine", Clinical and Vaccine Immunology, vol. 23, pp. 186-188, 2016.
Bangari et al., "Development of nonhuman adenoviruses as vaccine vectors", Vaccine, 24(7), pp. 849-862, 2006.
Cohen et al., "Chimpanzee adenovirus CV-68 adapted as a gene delivery vector interacts with the coxsackievirus and adenovirus receptor", Journal of General Virology, 83, pp. 151-155, 2002.
Farina et al., "Replication-Defective Vector Based on a Chimpanzee Adenovirus", Journal of Virology, vol. 75, No. 23, pp. 11603-11613, Dec. 2001.
Kobinger et al., "Chimpanzee adenovirus vaccine protects against Zaire Ebola Virus", Science Direct, Virology, 346, pp. 394-401, 2006.
Lasaro et al., "New Insights on Adenovirus as Vaccine Vectors", Molecular Therapy, vol. 17, No. 8, pp. 1333-1339, Aug. 2009.
Tatsis et al., "A CD46-binding Chimpanzee Adenovirus Vector as a Vaccine Carrier", American Society of Gene Therapy, vol. 15, No. 3, pp. 608-617, Mar. 2007.
Widjojatomodjo et al., "Recombianant Low-seroprevalent adenoviral vectors Ad26 and Ad35 expressing the respiratory syncytial virus (RSV) fusion protein induce protective immunity against RSV infection in cotton rats", Vaccine, 33, pp. 5406-5414, 2015.
Green et al., "Safety and Immunogenicity of novel respiratory syncytial virus (RSV) vaccines based on the RSV viral proteins F, N and M2-1 encoded by simian adenovirus (PanAd3-RSV) and MVA (MVA-RSV): protocol for an open-label, dose-escalation, single-centre, phase 1 clinical trial in healthy adults", BMJ Open, 13 pages, Oct. 2015.
Grunwald et al., "Novel Vaccine Regimen Elicits Strong Airway Immune Responses and Control of Respiratory Syncytial Virus in Nonhuman Primates", Journal of Virology, vol. 88, No. 8, pp. 3997-4007, Apr. 2014.
Int'l Search Report and Written Opinion dated Sep. 8, 2018 in Int'l Application No. PCT/EP2018/062604.
Vogels et al., "Replication-Deficient Human Adenvirus Type 35 Vectors for Gene Transfer and Vaccination: Efficient Human Cell Infection and Bypass of Preexisting Adenovirus Immunity" Journal of Virology, vol. 77, No. 15, pp. 8263-8271, Aug. 2003.
Gilman et al., "Rapid profiling of RSV antibody repertories from the memory B cells of naturally infected adult donors", Science Immunology, 11 pages, Dec. 2016.
Openshaw et al., "Protective and Harmful Immunity to RSV Infection", Annu Rev. Immunol, vol. 35, pp. 501-532, 2017.
Janssen Vaccines & Prevention B.V.: A Study to Evaluate the Safety, Tolerability and Immunogenicity of Two Vaccinations of Ad26. RSV. preF One Year Apart in Adults Aged 60 Years and Older in Stable Health, Oct. 2016, retrieved from the Internet: http://clinicaltrials.gov/ct2/show/record/NCT02926430 (retrived on Nov. 30, 2018.
Int'l Search Report and Written Opinion dated Dec. 17, 2018 in Int'l Application No. PCT/EP2018/074710.
International Search Report and Written Opinion issued in PCT/EP2017/062875, dated Aug. 14, 2017, 10 pages.

\* cited by examiner

S46G, E92D

N67I, E92D

E92D, S215P

— day 1
— day 5
— day 33

STABILIZED SOLUBLE PRE-FUSION RSV F POLYPEPTIDES

CROSS-REFERENCE TO RELATED APPLICATIONS

This application is a national phase entry under 35 U.S.C. § 371 of International Patent Application PCT/EP2014/058353, filed Apr. 24, 2014, designating the United States of America and published in English as International Patent Publication WO 2014/174018 A1 on Oct. 30, 2014, which claims the benefit under Article 8 of the Patent Cooperation Treaty to European Patent Application Serial No. 13165402.2, filed Apr. 25, 2013.

STATEMENT ACCORDING TO 37 C.F.R. § 1.821(c) OR (e)—SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

TECHNICAL FIELD

This disclosure relates to the field of medicine. The disclosure, in particular, relates to recombinant pre-fusion RSV F polypeptides and uses thereof, e.g., in immunogenic compositions.

BACKGROUND

Respiratory syncytial virus (RSV) is an enveloped non-segmented negative-strand RNA virus in the family Paramyxoviridae, genus *Pneumovirus*. Worldwide, it is estimated that 64 million RSV infections occur each year, resulting in 160,000 deaths (WHO Acute Respiratory Infections Update September 2009). The most severe disease occurs particularly in premature infants, the elderly and immune-compromised individuals. In children younger than 2 years, RSV is the most common respiratory tract pathogen, accounting for approximately 50% of the hospitalizations due to respiratory infections, with a peak of hospitalization occurring at 2-4 months of age. It has been reported that almost all children have been infected by RSV by the age of two. Repeated infection during lifetime is attributed to ineffective natural immunity. The level of RSV disease burden, mortality and morbidity in the elderly are second only to those caused by non-pandemic influenza A infections.

To infect a host cell, RSV, like other enveloped viruses such as influenza virus and HIV, require fusion of the viral membrane with a host cell membrane. For RSV, the conserved fusion protein (RSV F protein) fuses the viral and host cell cellular membranes. In current models, based on paramyxovirus studies, the RSV F protein initially folds into a "pre-fusion" conformation. During cell entry, the pre-fusion conformation undergoes refolding and conformational changes to its "post-fusion" conformation. Thus, the RSV F protein is a metastable protein that drives membrane fusion by coupling irreversible protein refolding to membrane juxtaposition by initially folding into a metastable form (pre-fusion conformation) that subsequently undergoes discrete/stepwise conformational changes to a lower energy conformation (post-fusion conformation).

It is clear from electron microscopy of RSV-F that large structural differences between the pre-fusion and post-fusion F trimer exist, which has recently been confirmed by crystallography (McLellan J. S. et al., Science 340(6136):1113-7 (2013) and McLellan J. S. et al., Science 342(6158):592-8 (2013)). These observations suggest that pre-fusion and post-fusion RSV F protein are antigenically distinct (Calder, L. J. et al., Virology 271:122-131 (2000)).

A vaccine against RSV infection is not currently available, but is desired. Vaccine candidates based on the RSV F protein have failed due to problems with, e.g., stability, purity, reproducibility, and potency. As indicated above, crystal structures have revealed a large conformational change between the pre-fusion and post-fusion states. The magnitude of the rearrangement suggested that only a portion of antibodies directed to the post-fusion conformation of RSV-F will be able to cross-react with the native conformation of the pre-fusion spike on the surface of the virus. Accordingly, efforts to produce a vaccine against RSV have focused on developing vaccines that contain pre-fusion forms of RSV F protein (see, e.g., WO2010/149743, WO2009/079796, and WO2012/158613). However, these efforts have not yet yielded stable pre-fusion RSV F polypeptides that could be used as candidates for testing in humans.

BRIEF SUMMARY

Provided are stable, recombinant, pre-fusion respiratory syncytial virus (RSV) fusion (F) polypeptides, i.e., recombinant RSV F polypeptides that are stabilized in the pre-fusion conformation. The RSV F polypeptides of the disclosure comprise at least one epitope that is specific to the pre-fusion conformation F protein. In certain embodiments, the pre-fusion RSV F polypeptides are soluble. In certain embodiments, the polypeptides are membrane-bound. Also provided are nucleic acid molecules (polynucleotides) encoding the pre-fusion RSV F polypeptides according to the disclosure and vectors comprising such nucleic acid molecules.

The disclosure also relates to compositions, preferably immunogenic compositions, comprising an RSV F polypeptide, a nucleic acid molecule and/or a vector, and to the use thereof in inducing an immune response against RSV F protein, in particular, the use thereof as a vaccine. The disclosure also relates to methods for inducing an anti-respiratory syncytial virus (RSV) immune response in a subject, comprising administering to the subject an effective amount of a pre-fusion RSV F polypeptide, a nucleic acid molecule encoding the RSV F polypeptide, and/or a vector comprising the nucleic acid molecule. Preferably, the induced immune response is characterized by neutralizing antibodies to RSV and/or protective immunity against RSV. In particular aspects, the disclosure relates to a method for inducing neutralizing anti-respiratory syncytial virus (RSV) F protein antibodies in a subject, comprising administering to the subject an effective amount of an immunogenic composition comprising a pre-fusion RSV F polypeptide, a nucleic acid molecule encoding the RSV F polypeptide, and/or a vector comprising the nucleic acid molecule.

BRIEF DESCRIPTION OF THE DRAWINGS

FIG. 1A, SUPERDEX® 200 gel filtration chromatogram of the eluate A2_F24 N67I+S215P from the ion-exchange column. The arrows indicate the elution points of standard protein (1-Thyroglobulin 669 kDa, 2-Ferritin 440 kDa and 3-IgG 150 kDa). FIG. 1B, SDS-PAGE analysis of the pre-fusion F protein containing peak from the SEC chromatogram under reducing conditions.

FIG. 4A illustrates determining the temperature where 50% of the CR9501 binding is lost; FIG. 4B shows a comparison of the stability of pre-fusion F (A2_F24 N67I+S215P) and the unmodified ectodomain when assessed by 50% loss of binding of the pre-fusion-specific antibody CR9501.

FIG. 5A, A2_F24 (SEQ ID NO:19); FIG. 5B, A2_F24 K465Q; FIG. 5C, A2_F24 S46G; FIG. 5D, A2_F24 N67I; and FIG. 5E, A2_F24 E92D at days 1, 5 and 33.

FIG. 6A, A2_F24 K465Q; FIG. 6B, A2_F24 K465Q+N67I; FIG. 6C, A2_F24 S46G; FIG. 6D, A2_F24 S46G+E92D; FIG. 6E, A2_F24 S46G+N67I; FIG. 6F, A2_F24 E92D; FIG. 6G, A2_F24 S46G+E92D; FIG. 6H, A2_F24 N67I+E92D; and FIG. 6I, A2_F24 E92D+S215P at days 1, 5 and 33.

DETAILED DESCRIPTION

Figure 1A:
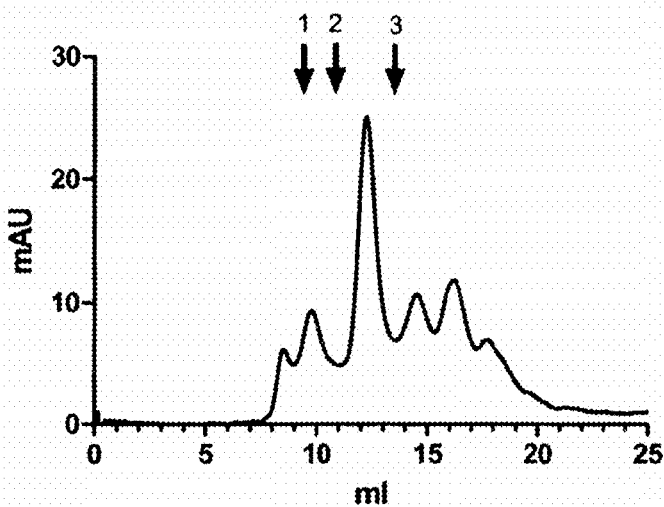
FIGS. 1A and 1B.
Figure 1B:
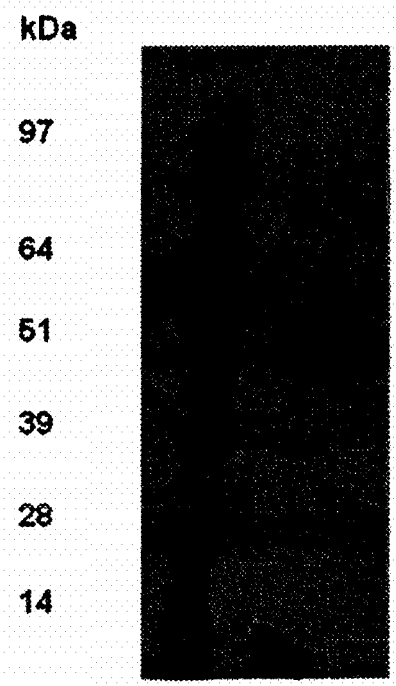
Figure 2:
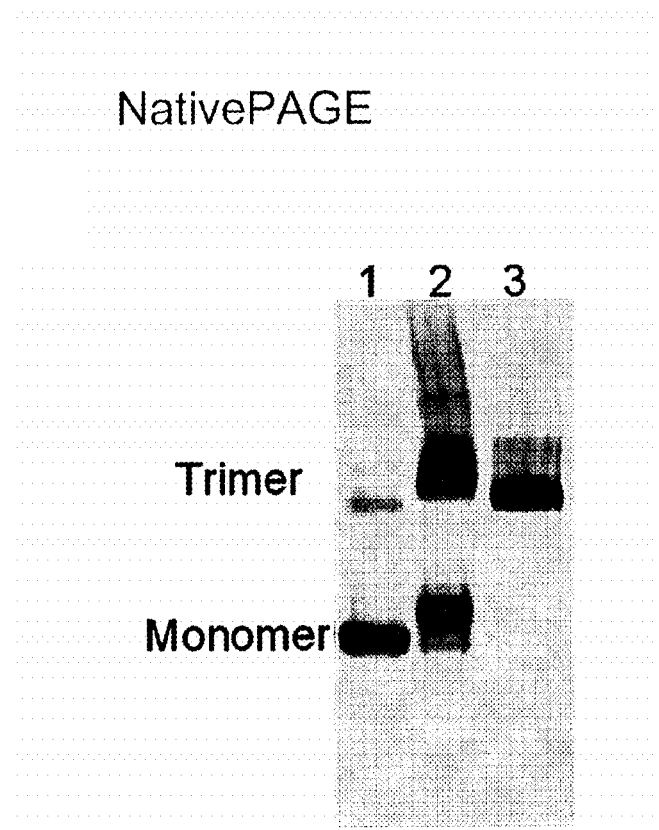
FIG. 2: Western blot of NativePAGE loaded with samples containing 1) supernatant from cells expressing pre-fusion construct with the isoleucine zipper (S) F43; 2) supernatant from cells expressing mainly trimeric (top band) post-fusion RSV F protein; and 3) purified trimeric pre-fusion A2_F24 N67I.
Figure 3:
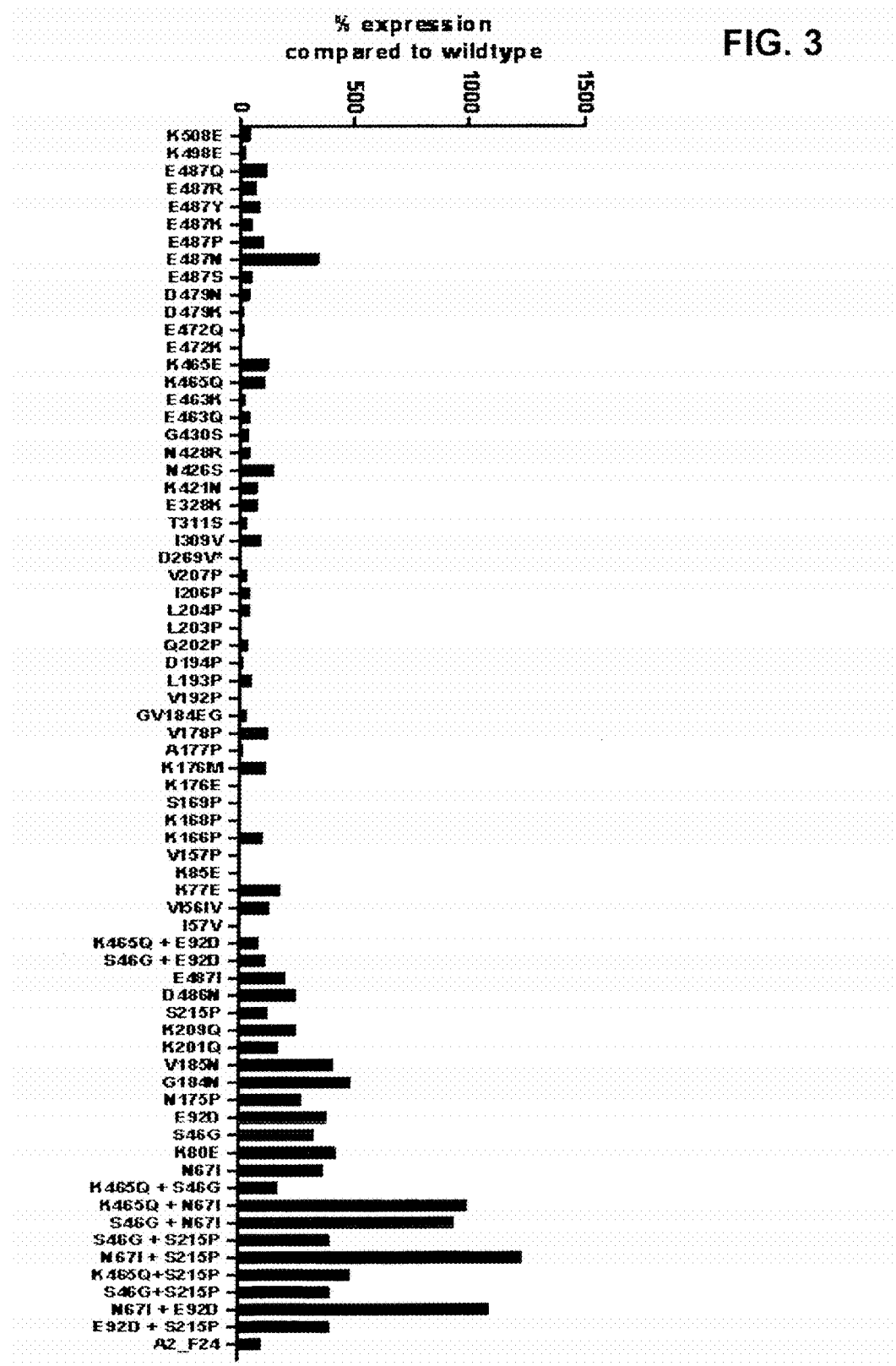
FIG. 3: Expression levels of the point-mutated constructs relative to the non-mutated A2_F24.

The fusion protein (F) of the respiratory syncytial virus (RSV) is involved in fusion of the viral membrane with a host cell membrane, which is required for infection. The RSV F mRNA is translated into a 574-amino acid precursor protein designated F0, which contains a signal peptide sequence at the N-terminus (e.g., amino acid residues 1-26 of SEQ ID NO:1) that is removed by a signal peptidase in the endoplasmic reticulum. F0 is cleaved at two sites (between amino acid residues 109/110 and 136/137) by cellular proteases (in particular, furin) in the trans-Golgi, removing a short glycosylated intervening sequence (also referred to as a "p27 region," comprising the amino acid residues 110 to 136, and generating two domains or subunits designated F1 and F2. The F1 domain (amino acid residues 137-574) contains a hydrophobic fusion peptide at its N-terminus and the C-terminus contains the transmembrane (TM) (amino acid residues 530-550) and cytoplasmic region (amino acid residues 551-574). The F2 domain (amino acid residues 27-109) is covalently linked to F1 by two disulfide bridges. The F1-F2 heterodimers are assembled as homotrimers in the virion.

A vaccine against RSV infection is not currently available, but is desired. One potential approach to producing a vaccine is a subunit vaccine based on purified RSV F protein. However, for this approach, it is desirable that the purified RSV F protein is in a conformation that resembles the conformation of the pre-fusion state of RSV F protein, that is stable over time, and can be produced in sufficient quantities. In addition, for a subunit-based vaccine, the RSV F protein needs to be truncated by deletion of the transmembrane (TM) and the cytoplasmic region to create a soluble secreted F protein (sF). Because the (TM) region is responsible for membrane anchoring and trimerization, the anchorless soluble F protein is considerably more labile than the full-length protein and will readily refold into the post-fusion end-state. In order to obtain soluble F protein in the stable pre-fusion conformation that shows high expression levels and high stability, the pre-fusion conformation thus needs to be stabilized.

Stabilization of another paramyxovirus F protein in the pre-fusion conformation has been successfully accomplished for parainfluenza type 5 (PIV-5). Yin et al. (Nature 439:38-44 (2006)) thus stabilized the pre-fusion structure of PIV-5 F protein by mutation of the furin cleavage site in $F_0$, which blocked processing into F1 and F2. Furthermore, the transmembrane (TM) and cytoplasmic domain were replaced by a well-known helical trimerization domain: GCN4-pII. This domain forms a trimeric helical coiled coil structure and is a modification of the natural dimeric helical coiled coil peptide GCN4 (O'Shea et al., Science 243:538-542 (1989)). The GCN4-pII peptide, in which the amino acid sequence of the GCN4 Leucine zipper was substituted with Isoleucine residues at every a and d position of the heptad, was shown to form a triple-stranded parallel alpha-helical coiled coil (Harbury et al., Science 262:1401-1407 (1993)).

For the stabilization of RSV F in the pre-fusion conformation, the same strategy has been tried, such as, e.g., mutation of the furin cleavage site, and fusion of the RSV-F ectodomain to a GCN4-pII trimerization domain (as disclosed in, e.g., WO2010/149743, WO2010/149745, WO2009/079796, and WO2012/158613) or to the fibritin trimerization domain (MCLellan et al., Nature Struct. Biol. 17:2-248-250 (2010)). This fibritin domain or "foldon" is derived from T4 fibritin and was described earlier as an artificial natural trimerization domain (Letarov et al., Biochemistry Moscow 64:817-823 (1993); S-Guthe et al., J. Mol. Biol. 337:905-915 (2004)). However, these efforts did not result in stable pre-fusion RSV-F protein. Moreover, these efforts have not yet resulted in candidates suitable for testing in humans.

This disclosure now provides recombinant stable pre-fusion RSV F polypeptides, i.e., RSV F polypeptides that are stabilized in the pre-fusion conformation. In the research that led to this disclosure, several modification steps were introduced and/or combined in order to obtain the stable soluble pre-fusion RSV F polypeptides. The stable pre-fusion RSV F polypeptides of the disclosure are in the pre-fusion conformation, i.e., they comprise (display) at least one epitope that is specific to the pre-fusion conformation F protein. An epitope that is specific to the pre-fusion conformation F protein is an epitope that is not presented in the post-fusion conformation. Without wishing to be bound by any particular theory, it is believed that the pre-fusion conformation of RSV F protein may contain epitopes that are the same as those on the RSV F protein expressed on natural RSV virions and, therefore, may provide advantages for eliciting protective neutralizing antibodies.

In certain embodiments, the polypeptides of the disclosure comprise at least one epitope that is recognized by a pre-fusion specific monoclonal antibody, comprising a heavy chain CDR1 region of SEQ ID NO:54, a heavy chain CDR2 region of SEQ ID NO:55, a heavy chain CDR3 region of SEQ ID NO:56 and a light chain CDR1 region of SEQ ID NO:62, a light chain CDR2 region of SEQ ID NO:63, and a light chain CDR3 region of SEQ ID NO:64 (hereafter referred to as CR9501) and/or a pre-fusion specific monoclonal antibody, comprising a heavy chain CDR1 region of SEQ ID NO:58, a heavy chain CDR2 region of SEQ ID NO:59, a heavy chain CDR3 region of SEQ ID NO:60 and a light chain CDR1 region of SEQ ID NO:66, a light chain CDR2 region of SEQ ID NO:67, and a light chain CDR3 region of SEQ ID NO:68 (referred to as CR9502). CR9501 and CR9502 comprise the heavy and light chain variable regions and, thus, the binding specificities of the antibodies 58C5 and 30D8, respectively, which have previously been shown to bind specifically to RSV F protein in its pre-fusion conformation and not to the post-fusion conformation (see WO2012/006596).

In certain embodiments, the recombinant pre-fusion RSV F polypeptides comprise at least one epitope that is recognized by at least one pre-fusion specific monoclonal antibody as described above and are trimeric.

In certain embodiments, the stable pre-fusion RSV F polypeptides according to the disclosure comprise a mutation of the amino acid residue on position 67 and/or a mutation of the amino acid residue on position 215.

In certain embodiments, the amino acid on position 67 is mutated to a hydrophobic amino acid.

In certain embodiments, the stable pre-fusion RSV F polypeptides according to the disclosure comprise a mutation of the amino acid residue N or T on position 67 and/or a mutation of amino acid residue S on position 215.

In certain embodiments, the stable pre-fusion RSV F polypeptides according to the disclosure comprise an F1 domain and an F2 domain, and a linking sequence comprising from 1 to 10 amino acid residues, linking the F1 domain to the F2 domain, wherein the polypeptides further comprise a mutation of the amino acid residue N or T on position 67 and/or a mutation of amino acid residue S on position 215.

In certain embodiments, the stable pre-fusion RSV F polypeptides according to the disclosure comprise a truncated F1 domain and an F2 domain, and a linking sequence comprising from 1 to 10 amino acid residues, linking the truncated F1 domain to the F2 domain, wherein the polypeptides further comprise a mutation of the amino acid residue N or T on position 67 and/or a mutation of amino acid residue S on position 215.

The polypeptides of the disclosure thus comprise at least one stabilizing mutation in the F1 and/or F2 domain as compared to the RSV F1 and/or F2 domain in a wild-type RSV F protein.

In certain embodiments, the pre-fusion RSV F polypeptides comprise a mutation of amino acid residue N or T on position 67 (N/T67I) into I and/or a mutation of amino acid residue S on position 215 into P (S215P).

It is known that RSV exists as a single serotype having two antigenic subgroups: A and B. The amino acid sequences of the mature processed F proteins of the two groups are about 93% identical. As used throughout the present application, the amino acid positions are given in reference to the sequence of RSV F protein from the A2 strain (SEQ ID NO:1). As used in this disclosure, the wording "the amino acid at position "x" of the RSV F protein" thus means the amino acid corresponding to the amino acid at position "x" in the RSV F protein of the RSV A2 strain of SEQ ID NO:1. Note that, in the numbering system used throughout this application, "1" refers to the N-terminal amino acid of an immature F0 protein (SEQ ID NO:1). When an RSV strain other than the A2 strain is used, the amino acid positions of the F protein are to be numbered with reference to the numbering of the F protein of the A2 strain of SEQ ID NO:1 by aligning the sequences of the other RSV strain with the F protein of SEQ ID NO:1 with the insertion of gaps as needed. Sequence alignments can be done using methods well known in the art, e.g., by CLUSTALW, Bioedit or CLC Workbench.

An amino acid according to the disclosure can be any of the twenty naturally occurring (or "standard" amino acids) or variants thereof, such as, e.g., D-amino acids (the D-enantiomers of amino acids with a chiral center), or any variants that are not naturally found in proteins, such as, e.g., norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that induces turns of the polypeptide backbone, and glycine that is more flexible than other amino acids. Table 11 shows the abbreviations and properties of the standard amino acids.

It will be appreciated by a skilled person that the mutations can be made to the protein by routine molecular biology procedures. The mutations according to the disclosure preferably result in increased expression levels and/or increased stabilization of the pre-fusion RSV F polypeptides as compared to RSV F polypeptides that do not comprise these mutation(s).

In certain embodiments, the pre-fusion RSV F polypeptides are soluble.

In certain embodiments, the pre-fusion RSV F polypeptides further comprise a heterologous trimerization domain linked to the truncated F1 domain. According to the disclosure, it was shown that by linking a heterologous trimerization domain to the C-terminal amino acid residue of a truncated F1 domain, optionally combined with a linking sequence linking the F1 and F2 domains, and the stabilizing mutation(s), RSV F polypeptides are provided that show high expression and that bind to pre-fusion-specific antibodies, indicating that the polypeptides are in the pre-fusion conformation. In addition, the RSV F polypeptides are stabilized in the pre-fusion conformation, i.e., even after processing of the polypeptides, they still bind to the pre-fusion-specific antibodies CR9501 and/or CR9502, indicating that the pre-fusion-specific epitope is retained.

In further embodiments, the pre-fusion RSV F polypeptides comprise one or more further mutations (as compared to the wild-type RSV F protein), selected from the group consisting of:

(a) a mutation of the amino acid residue on position 46;
(b) a mutation of the amino acid residue on position 77;
(c) a mutation of the amino acid residue on position 80;
(d) a mutation of the amino acid residue on position 92;
(e) a mutation of the amino acid residue on position 175;
(f) a mutation of the amino acid residue on position 184;
(g) a mutation of the amino acid residue on position 185;
(h) a mutation of the amino acid residue on position 201;
(i) a mutation of the amino acid residue on position 209;
(j) a mutation of the amino acid residue on position 421;
(k) a mutation of the amino acid residue on position 426;

(l) a mutation of the amino acid residue on position 465;
(m) a mutation of the amino acid residue on position 486;
(n) a mutation of the amino acid residue on position 487; and
(o) a mutation of the amino acid residue on position 508.

In preferred embodiments, the one or more further mutations are selected from the group consisting of:
(a) a mutation of the amino acid residue S on position 46 into G (S46G);
(b) a mutation of the amino acid residue K on position 77 into E (K77E);
(c) a mutation of the amino acid residue K on position 80 into E (K80E);
(d) a mutation of the amino acid residue E on position 92 into D (E92D);
(e) a mutation of the amino acid residue N on position 175 into P (N175P);
(f) a mutation of the amino acid residue G on position 184 into N (G184N);
(g) a mutation of the amino acid residue V on position 185 into N (V185N);
(h) a mutation of the amino acid residue K on position 201 into Q (K201Q);
(i) a mutation of the amino acid residue K on position 209 into Q (K209Q);
(j) a mutation of the amino acid residue K on position 421 into N (K421N);
(k) a mutation of the amino acid residue N on position 426 into S (N426S);
(l) a mutation of the amino acid residue K on position 465 into E or Q (K465E/Q);
(m) a mutation of the amino acid residue D on position 486 into N (D486N);
(n) a mutation of the amino acid residue E on position 487 into Q, N or I (E487Q/N/I); and
(o) a mutation of the amino acid residue K on position 508 into E (K508E).

It is again noted that for the positions of the amino acid residues, reference is made to SEQ ID NO:1. A skilled person will be able to determine the corresponding amino acid residues in F proteins of other RSV strains.

In certain embodiments, the pre-fusion RSV F polypeptides comprise at least two mutations (as compared to a wild-type RSV F protein). In preferred embodiments, the at least two mutations are a mutation of the amino acid N or T on position 67 into I (N/T67I) and a mutation of the amino acid S on position 215 into P (S215P).

In certain embodiments, the pre-fusion RSV F polypeptides comprise at least one further mutation, selected from the group consisting of:
(a) a mutation of the amino acid residue S on position 46 into G;
(b) a mutation of the amino acid residue K on position 77 into E;
(c) a mutation of the amino acid residue K on position 80 into E;
(d) a mutation of the amino acid residue E on position 92 into D;
(e) a mutation of the amino acid residue N on position 175 into P;
(f) a mutation of the amino acid residue G on position 184 into N;
(g) a mutation of the amino acid residue V on position 185 into N;
(h) a mutation of the amino acid residue K on position 201 into Q;
(i) a mutation of the amino acid residue K on position 209 into Q;
(j) a mutation of the amino acid residue K on position 421 into N;
(k) a mutation of the amino acid residue N on position 426 into S;
(l) a mutation of the amino acid residue K on position 465 into E or Q;
(m) a mutation of the amino acid residue D on position 486 into N;
(n) a mutation of the amino acid residue E on position 487 into Q, N or I; and
(o) a mutation of the amino acid residue K or R on position 508 into E.

In certain embodiments, the polypeptides comprise at least three mutations.

In certain embodiments, the heterologous trimerization domain comprises the amino acid sequence EKKIEAIEKKIEAIEKKIEA (SEQ ID NO:3). In certain other embodiments, the heterologous trimerization domain comprises the amino acid sequence GYIPEAPRDGQAYVRKDGEWVLLSTFL (SEQ ID NO:4).

As described above, in certain embodiments the polypeptides of the disclosure comprise a truncated F1 domain. As used herein, a "truncated" F1 domain refers to an F1 domain that is not a full-length F1 domain, i.e., wherein, either N-terminally or C-terminally, one or more amino acid residues have been deleted. According to the disclosure, at least the transmembrane domain and cytoplasmic tail have been deleted to permit expression as a soluble ectodomain.

In certain other embodiments, the F1 domain is truncated after amino acid residue 495 of the RSV F protein (referring to SEQ ID NO:1), i.e., the C-terminal part of the F1 domain starting from amino acid residue 496 (referring to SEQ ID NO:1) has been deleted. In certain other embodiments, the F1 domain is truncated after amino acid residue 513 of the RSV F protein. In certain embodiments, the F1 domain is truncated after amino acid residue 486, 487, 488, 489, 490, 491, 492, 493, 494, 495, 496, 497, 498, 499, 500, 501, 502, 503, 504, 505, 506, 507, 508, 509, 510, 512, 513, 514, 515, 516, 517, 518, 519, 520, 521, 522, 523, 524 or 525.

In certain embodiments, the trimerization domain is linked to amino acid residue 495 of the RSV F1 domain. In certain embodiments, the trimerization domain comprises SEQ ID NO:4 and is linked to amino acid residue 495 of the RSV F1 domain.

In certain other embodiments, the trimerization domain is linked to amino acid residue 513 of the RSV F1 domain. In certain embodiments, the trimerization domain comprises SEQ ID NO:3 and is linked to amino acid residue 513 of the RSV F1 domain.

In certain embodiments, the F1 domain, which is optionally truncated, and the F2 domain are linked by a linking sequence, linking the C-terminal amino acid of the F2 domain to the N-terminal amino acid of the (optionally truncated) F1 domain. In certain embodiments, the linking sequence (or linker) comprises from 1-10 amino acid residues, preferable from 2-9 amino acid residues, preferably from 3-8 amino acid residues, preferably from 4-7 amino acid residues, more preferably, the linker comprises 5 or 6 amino acid residues. Numerous conformationally neutral linkers are known in the art that can be used according to the disclosure without disrupting the conformation of the pre-fusion RSV F polypeptides. In preferred embodiments, the linker comprises the amino acid sequence GSGSG (SEQ ID NO:5).

In certain embodiments, the F1 domain and/or the F2 domain are from an RSV A strain. In certain embodiments, the F1 and/or F2 domain are from the RSV A2 strain of SEQ ID NO:1.

In certain embodiments, the F1 domain and/or the F2 domain are from an RSV A strain, such as from the RSV A strain of SEQ ID NO:69.

In certain embodiments, the F1 domain and/or the F2 domain are from an RSV B strain. In certain embodiments, the F1 and/or F2 domain are from the RSV B strain of SEQ ID NO:2.

In certain embodiments, the F1 and F2 domain are from the same RSV strain. In certain embodiments, the pre-fusion RSV F polypeptides are chimeric polypeptides, i.e., comprising F1 and F2 domains that are from different RSV strains.

In certain embodiments, the level of expression of the pre-fusion RSV F polypeptides of the disclosure is increased, as compared to a wild-type RSV F polypeptide ectodomain (i.e., without the transmembrane and cytoplasmic region) without the mutation(s). In certain embodiments, the level of expression is increased at least five-fold, preferably up to ten-fold. In certain embodiments, the level of expression is increased more than ten-fold.

The pre-fusion RSV F polypeptides according to the disclosure are stable, i.e., do not readily change into the post-fusion conformation upon processing of the polypeptides, such as, e.g., purification, freeze-thaw cycles, and/or storage, etc.

In certain embodiments, the pre-fusion RSV F polypeptides according to the disclosure have an increased stability upon storage at 4° C., as compared to an RSV F polypeptide without the mutation(s). In certain embodiments, the polypeptides are stable upon storage at 4° C. for at least 30 days, preferably at least 60 days, preferably at least 6 months, even more preferably at least 1 year. With "stable upon storage," it is meant that the polypeptides still display the at least one epitope specific for the pre-fusion specific antibody (e.g., CR9501) upon storage of the polypeptide in solution (e.g., culture medium) at 4° C. for at least 30 days, e.g., as determined using a method as described in Example 7 or 9. In certain embodiments, the polypeptides display the at least one pre-fusion-specific epitope for at least 6 months, preferably for at least 1 year upon storage of the pre-fusion RSV F polypeptides at 4° C.

In certain embodiments, the pre-fusion RSV F polypeptides according to the disclosure have an increased stability when subjected to heat, as compared to RSV F polypeptides without the mutation(s). In certain embodiments, the pre-fusion RSV F polypeptides are heat stable for at least 30 minutes at a temperature of 55° C., preferably at 58° C., more preferably at 60° C. With "heat stable" it is meant that the polypeptides still display the at least one pre-fusion-specific epitope after having been subjected for at least 30 minutes to an increased temperature (i.e., a temperature of 55° C. or above), e.g., as determined using a method as described in Example 6.

In certain embodiments, the polypeptides display the at least one pre-fusion-specific epitope after being subjected to 1 to 6 freeze-thaw cycles in an appropriate formulation buffer.

In certain preferred embodiments, the pre-fusion RSV F polypeptide of the disclosure comprises an amino acid sequence selected from the group consisting of SEQ ID NOS:21-52 and 71-89. In certain embodiments, the pre-fusion RSV F polypeptide of the disclosure consists of an amino acid sequence selected from the group consisting of SEQ ID NOS:21-52 and 71-89.

As used throughout this disclosure, nucleotide sequences are provided from 5' to 3' direction, and amino acid sequences from N-terminus to C-terminus, as customary in the art.

In certain embodiments, the encoded polypeptides according to the disclosure further comprise a leader sequence, also referred to as "signal sequence" or "signal peptide," corresponding to amino acids 1-26 of SEQ ID NO:1, SEQ ID NO:2 or SEQ ID NO:69. This is a short (typically 5-30 amino acids long) peptide present at the N-terminus of the majority of newly synthesized proteins that are destined toward the secretory pathway. In certain embodiments, the polypeptides according to the disclosure do not comprise a leader sequence.

In certain embodiments, the polypeptides comprise a HIS-Tag. A His-Tag or polyhistidine-tag is an amino acid motif in proteins that consists of at least five histidine (H) residues, often at the N- or C-terminus of the protein, which is generally used for purification purposes.

In certain embodiments, the polypeptides do not comprise a HIS-Tag. According to the disclosure, it has surprisingly been shown that when the HIS-tag is deleted, the level of expression and the stability are increased as compared to polypeptides with a HIS-tag.

This disclosure further provides nucleic acid molecules encoding the RSV F polypeptides according to the disclosure.

In preferred embodiments, the nucleic acid molecules encoding the polypeptides according to the disclosure are codon-optimized for expression in mammalian cells, preferably human cells. Methods of codon-optimization are known and have been described previously (e.g., WO 96/09378). A sequence is considered codon-optimized if at least one non-preferred codon as compared to a wild-type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as on the World Wide Web at kazusa.or.jp/codon. Preferably, more than one non-preferred codon, preferably most or all non-preferred codons, are replaced by codons that are more preferred. Preferably, the most frequently used codons in an organism are used in a codon-optimized sequence. Replacement by preferred codons generally leads to higher expression.

It will be understood by a skilled person that numerous different polynucleotides and nucleic acid molecules can encode the same polypeptide as a result of the degeneracy of the genetic code. It is also understood that skilled persons may, using routine techniques, make nucleotide substitutions that do not affect the polypeptide sequence encoded by the nucleic acid molecules to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may or may not include introns.

Nucleic acid sequences can be cloned using routine molecular biology techniques, or generated de novo by DNA synthesis, which can be performed using routine procedures by service companies having business in the field of DNA synthesis and/or molecular cloning (e.g., GENEART®, GenScript®, INVITROGEN®, and EUROFINS®).

The disclosure also provides vectors comprising a nucleic acid molecule as described above. In certain embodiments, a nucleic acid molecule according to the disclosure thus is part of a vector. Such vectors can easily be manipulated by methods well known to the person skilled in the art, and can, for instance, be designed for being capable of replication in prokaryotic and/or eukaryotic cells. In addition, many vectors can be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. Suitable vectors according to the disclosure are, e.g., adenovectors, such as, e.g., Ad26 or Ad35, alphavirus, paramyxovirus, vaccinia virus, herpes virus, retroviral vectors, etc. The person skilled in the art is capable of choosing suitable expression vectors, and inserting the nucleic acid sequences of the disclosure in a functional manner.

Host cells comprising the nucleic acid molecules encoding the pre-fusion RSV F polypeptides also form part of the disclosure. The pre-fusion RSV F polypeptides may be produced through recombinant DNA technology involving expression of the molecules in host cells, e.g., Chinese hamster ovary (CHO) cells, tumor cell lines, BHK cells, human cell lines such as HEK293 cells, PER.C6® cells, or yeast, fungi, insect cells, and the like, or transgenic animals or plants. In certain embodiments, the cells are from a multicellular organism; in certain embodiments, they are of vertebrate or invertebrate origin. In certain embodiments, the cells are mammalian cells. In certain embodiments, the cells are human cells. In general, the production of recombinant proteins in a host cell, such as the pre-fusion RSV F polypeptides of the disclosure, comprises the introduction of a heterologous nucleic acid molecule encoding the polypeptide in expressible format into the host cell, culturing the cells under conditions conducive to expression of the nucleic acid molecule and allowing expression of the polypeptide in the cell. The nucleic acid molecule encoding a protein in expressible format may be in the form of an expression cassette, and usually requires sequences capable of bringing about expression of the nucleic acid, such as enhancer(s), promoter, polyadenylation signal, and the like. The person skilled in the art is aware that various promoters can be used to obtain expression of a gene in host cells. Promoters can be constitutive or regulated, and can be obtained from various sources, including viruses, prokaryotic, or eukaryotic sources, or artificially designed.

Cell culture media are available from various vendors, and a suitable medium can be routinely chosen for a host cell to express the protein of interest, here, the pre-fusion RSV F polypeptides. The suitable medium may or may not contain serum.

A "heterologous nucleic acid molecule" (also referred to herein as "transgene") is a nucleic acid molecule that is not naturally present in the host cell. It is introduced into, for instance, a vector by standard molecular biology techniques. A transgene is generally operably linked to expression control sequences. This can, for instance, be done by placing the nucleic acid encoding the transgene(s) under the control of a promoter. Further regulatory sequences may be added. Many promoters can be used for expression of a transgene(s), and are known to the skilled person, e.g., these may comprise viral, mammalian, synthetic promoters, and the like. A non-limiting example of a suitable promoter for obtaining expression in eukaryotic cells is a CMV-promoter (U.S. Pat. No. 5,385,839), e.g., the CMV immediate early promoter, for instance, comprising nt. −735 to +95 from the CMV immediate early gene enhancer/promoter. A polyadenylation signal, for example, the bovine growth hormone polyA signal (U.S. Pat. No. 5,122,458), may be present behind the transgene(s). Alternatively, several widely used expression vectors are available in the art and from commercial sources, e.g., the pcDNA and pEF vector series of INVITROGEN®, pMSCV and pTK-Hyg from BD Sciences, pCMV-Script from STRATAGENE™, etc., which can be used to recombinantly express the protein of interest, or to obtain suitable promoters and/or transcription terminator sequences, polyA sequences, and the like.

The cell culture can be any type of cell culture, including adherent cell culture, e.g., cells attached to the surface of a culture vessel or to microcarriers, as well as suspension culture. Most large-scale suspension cultures are operated as batch or fed-batch processes because they are the most straightforward to operate and scale up. Nowadays, continuous processes based on perfusion principles are becoming more common and are also suitable. Suitable culture media are also well known to the skilled person and can generally be obtained from commercial sources in large quantities, or custom-made according to standard protocols. Culturing can be done, for instance, in dishes, roller bottles or in bioreactors, using batch, fed-batch, continuous systems, and the like. Suitable conditions for culturing cells are known (see, e.g., Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9)).

The disclosure further provides compositions comprising a pre-fusion RSV F polypeptide and/or a nucleic acid molecule, and/or a vector, as described above. The disclosure thus provides compositions comprising a pre-fusion RSV F polypeptide that displays an epitope that is present in a pre-fusion conformation of the RSV F protein but is absent in the post-fusion conformation. The disclosure also provides compositions comprising a nucleic acid molecule and/or a vector, encoding such pre-fusion RSV F polypeptide. The disclosure further provides immunogenic compositions comprising a pre-fusion RSV F polypeptide, and/or a nucleic acid molecule, and/or a vector, as described above. The disclosure also provides the use of a stabilized pre-fusion RSV F polypeptide, a nucleic acid molecule, and/or a vector, according to the disclosure, for inducing an immune response against RSV F protein in a subject. Further provided are methods for inducing an immune response against RSV F protein in a subject, comprising administering to the subject a pre-fusion RSV F polypeptide, and/or a nucleic acid molecule, and/or a vector, according to the disclosure. Also provided are pre-fusion RSV F polypeptides, nucleic acid molecules, and/or vectors, according to the disclosure for use in inducing an immune response against RSV F protein in a subject. Further provided is the use of the pre-fusion RSV F polypeptides, and/or nucleic acid molecules, and/or vectors according to the disclosure for the manufacture of a medicament for use in inducing an immune response against RSV F protein in a subject.

The pre-fusion RSV F polypeptides, nucleic acid molecules, or vectors of the disclosure may be used for prevention (prophylaxis) and/or treatment of RSV infections. In certain embodiments, the prevention and/or treatment may be targeted at patient groups that are susceptible to RSV infection. Such patient groups include, but are not limited to, e.g., the elderly (e.g., ≥50 years old, ≥60 years old, and preferably ≥65 years old), the young (e.g., ≤5 years old and ≤1 year old), hospitalized patients and patients who have been treated with an antiviral compound but have shown an inadequate antiviral response.

The pre-fusion RSV F polypeptides, nucleic acid molecules and/or vectors according to the disclosure may be used, e.g., in stand-alone treatment and/or prophylaxis of a disease or condition caused by RSV, or in combination with other prophylactic and/or therapeutic treatments, such as (existing or future) vaccines, antiviral agents and/or monoclonal antibodies.

The disclosure further provides methods for preventing and/or treating RSV infection in a subject utilizing the pre-fusion RSV F polypeptides, nucleic acid molecules and/or vectors according to the disclosure. In a specific embodiment, a method for preventing and/or treating RSV infection in a subject comprises administering to a subject in need thereof an effective amount of a pre-fusion RSV F polypeptide, nucleic acid molecule and/or a vector, as described above. A therapeutically effective amount refers to an amount of a polypeptide, nucleic acid molecule or vector that is effective for preventing, ameliorating and/or treating a disease or condition resulting from infection by RSV. Prevention encompasses inhibiting or reducing the spread of RSV or inhibiting or reducing the onset, development or progression of one or more of the symptoms associated with infection by RSV. "Amelioration" as used in herein may refer to the reduction of visible or perceptible disease symptoms, viremia, or any other measurable manifestation of influenza infection.

For administering to subjects, such as humans, the disclosure may employ pharmaceutical compositions comprising a pre-fusion RSV F polypeptide, a nucleic acid molecule and/or a vector as described herein, and a pharmaceutically acceptable carrier or excipient. In the present context, the term "pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The RSV F polypeptides, or nucleic acid molecules, preferably are formulated and administered as a sterile solution, although it may also be possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g., pH 5.0 to 7.5. The RSV F polypeptides typically are in a solution having a suitable pharmaceutically acceptable buffer, and the composition may also contain a salt. Optionally, stabilizing agent may be present, such as albumin. In certain embodiments, detergent is added. In certain embodiments, the RSV F polypeptides may be formulated into an injectable preparation.

In certain embodiments, a composition according to the disclosure further comprises one or more adjuvants. Adjuvants are known in the art to further increase the immune response to an applied antigenic determinant. The terms "adjuvant" and "immune stimulant" are used interchangeably herein, and are defined as one or more substances that cause stimulation of the immune system. In this context, an adjuvant is used to enhance an immune response to the RSV F polypeptides of the disclosure. Examples of suitable adjuvants include aluminium salts such as aluminium hydroxide and/or aluminium phosphate; oil-emulsion compositions (or oil-in-water compositions), including squalene-water emulsions, such as MF59 (see, e.g., WO 90/14837); saponin formulations, such as, for example, QS21 and Immunostimulating Complexes (ISCOMS) (see, e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli, heat labile enterotoxin LT, cholera toxin CT, and the like; eukaryotic proteins (e.g., antibodies or fragments thereof (e.g., directed against the antigen itself or CD1a, CD3, CD7, or CD80) and ligands to receptors (e.g., CD40L, GMCSF, GCSF, etc.), which stimulate immune response upon interaction with recipient cells. In certain embodiments, the compositions of the disclosure comprise aluminium as an adjuvant, e.g., in the form of aluminium hydroxide, aluminium phosphate, aluminium potassium phosphate, or combinations thereof, in concentrations of 0.05-5 mg, e.g., from 0.075-1.0 mg, of aluminium content per dose.

The pre-fusion RSV F polypeptides may also be administered in combination with or conjugated to nanoparticles, such as, e.g., polymers, liposomes, virosomes, and virus-like particles. The pre-fusion F polypeptides may be combined with, encapsidated in, or conjugated to the nanoparticles with or without adjuvant. Encapsulation within liposomes is described, e.g., in U.S. Pat. No. 4,235,877. Conjugation to macromolecules is disclosed, for example, in U.S. Pat. No. 4,372,945 or 4,474,757.

In other embodiments, the compositions do not comprise adjuvants.

In certain embodiments, the disclosure provides methods for making a vaccine against respiratory syncytial virus (RSV), comprising providing a composition according to the disclosure and formulating it into a pharmaceutically acceptable composition. The term "vaccine" refers to an agent or composition containing an active component effective to induce a certain degree of immunity in a subject against a certain pathogen or disease, which will result in at least a decrease (up to complete absence) of the severity, duration or other manifestation of symptoms associated with infection by the pathogen or the disease. In this disclosure, the vaccine comprises an effective amount of a pre-fusion RSV F polypeptide and/or a nucleic acid molecule encoding a pre-fusion RSV F polypeptide, and/or a vector comprising the nucleic acid molecule, which results in an immune response against the F protein of RSV. This provides a method of preventing serious lower respiratory tract disease leading to hospitalization and the decrease in frequency of complications such as pneumonia and bronchiolitis due to RSV infection and replication in a subject. The term "vaccine" according to the disclosure implies that it is a pharmaceutical composition and, thus, typically includes a pharmaceutically acceptable diluent, carrier or excipient. It may or may not comprise further active ingredients. In certain embodiments, it may be a combination vaccine that further comprises other components that induce an immune response, e.g., against other proteins of RSV and/or against other infectious agents. The administration of further active components may, for instance, be done by separate administration or by administering combination products of the vaccines of the disclosure and the further active components.

Compositions may be administered to a subject, e.g., a human subject. The total dose of the RSV F polypeptides in a composition for a single administration can, for instance, be about 0.01 µg to about 10 mg, e.g., 1 µg-1 mg, e.g., 10 µg-100 µg. Determining the recommended dose will be carried out by experimentation and is routine for those skilled in the art.

Administration of the compositions according to the disclosure can be performed using standard routes of administration. Non-limiting embodiments include parenteral administration, such as intradermal, intramuscular, subcutaneous, transcutaneous, or mucosal administration, e.g., intranasal, oral, and the like. In one embodiment, a composition is administered by intramuscular injection. The skilled person knows the various possibilities to administer a composition, e.g., a vaccine, in order to induce an immune response to the antigen(s) in the vaccine.

A "subject" as used herein, is preferably a mammal, for instance, a rodent, e.g., a mouse, a cotton rat, or a non-human-primate, or a human. Preferably, the subject is a human subject.

The polypeptides, nucleic acid molecules, vectors, and/or compositions may also be administered, either as prime, or as boost, in a homologous or heterologous prime-boost regimen. Typically, if a boosting vaccination is performed, such a boosting vaccination will be administered to the same subject at a time between one week and one year, preferably between two weeks and four months, after administering the composition to the subject for the first time (which is in such cases referred to as "priming vaccination"). In certain embodiments, the administration comprises a prime and at least one booster administration.

In addition, the polypeptides of the disclosure may be used as diagnostic tools, for example, to test the immune status of an individual by establishing whether there are antibodies in the serum of such individual capable of binding to the polypeptide of the disclosure. Thus, the disclosure also relates to an in vitro diagnostic method for detecting the presence of an RSV infection in a patient, the method comprising the steps of a) contacting a biological sample obtained from the patient with a polypeptide according to the disclosure; and b) detecting the presence of antibody-polypeptide complexes.

The disclosure further provides a method for stabilizing the pre-fusion conformation of an RSV F polypeptide, comprising introducing one or more mutations in an RSV F1 and/or F2 domain, as compared to the wild-type RSV F1 and/or F2 domain, wherein the one or more mutations are selected from the group consisting of:
  (a) a stabilizing mutation that locks the HRA domain from hinging in a region adjacent to the conserved 69-212 disulfide bridge, the region comprising the amino acid residues 66-68 and 214-216,
  (b) a mutation in the helix (at the C-terminus of the F2 domain) comprising the amino acid residues 76-98 at the C-terminus of the F2 domain;
  (c) a mutation that reduces the negative charge repulsion between the top of the HRB stem region (N-terminal end of HRB) comprising amino acids 486, 487 and 489; and
  (d) a stabilizing mutation in the HRA region.

In certain embodiments, the mutation in the HRA hinge region is at position 67.

In certain embodiments, the mutation in the HRA hinge region is at position 215.

In certain embodiments, the mutation in the HRA hinge region is at position 66 or 68, and/or at position 214 or 216.

In certain embodiments, the mutation in the helix is at position 77.

In certain embodiments, the mutation in the helix is at position 80.

In certain embodiments, the amino acid residue at position 77 and/or 80 is changed into a negatively charged amino acid.

In certain embodiments, the mutation is at position 92.

In certain embodiments, the mutation that reduces the negative charge repulsion between the top of the HRB stem region comprises amino acids 486, 487, and 489.

In certain embodiments, the mutation is at position 489.

In certain embodiments, the mutation is at position 486.

In certain embodiments, the mutation stabilizes the beta-turns between the amino acid residues 175-193.

In certain embodiments, the mutation is stabilizing the turn at position 175.

In certain embodiments, the mutation is stabilizing the turn at position 184 and 185.

Stabilized pre-fusion RSV F polypeptides obtainable and/or obtained by such method also form part of the disclosure, as well as the uses thereof as described above.

The disclosure is further explained in the examples below. The examples do not limit the disclosure in any way; they merely serve to clarify the disclosure.

EXAMPLES

Example 1: Preparation of Stable Pre-Fusion RSV F Polypeptides—Linkers and Trimerization Domains In the research that led to this disclosure, stabilized variants of soluble pre-fusion F protein (sF) were designed by stabilizing the two main regions that initiate refolding. The first strategy was to arrest the fusion peptide in its position and prevent it from getting released from the head region by fixing and joining the F1-F2 domains by a short loop. Release of the fusion peptide can be prevented by re-establishing a covalent connection of the N-terminus of F1 to the C-terminus of F2. As shown in this example, several different linkers have been tried. The insertion of a five-amino acid loop between F1 and F2, in particular, comprising the amino acid sequence GSGSG (SEQ ID NO:5), was most successful. This linker was designed based on the distances measured in a 3D homology model that was generated for RSV-F type A2 based on the sequence alignment with the F sequence of parainfluenza type 5 for which a three-dimensional structure is published (Yin et. al., 2006).

```
SEQ ID NO: 90 (first line)
SEQ ID NO: 91 (second line)
SEQ ID NO: 92 (third line)

AAA47881PIV5          -------------MGTIIQFLVVSCLLAGAGSLDPAALMQIGVIPTNVRQLMYYTEASSA
FUS_HRSV1B            ------MELLIHRSSAIFLTLAVNALYLTSSQNITEEFYQSTCSAVSRGYFSALRTGWYT
ACO83301HRSVA2ref     ------MELLILKANAITTILTAVTFCFASGQNITEEFYQSTCSAVSKGYLSALRTGWYT
                          .:*   *..   :  :..  . :*    ...  :    . :
```

-continued

```
AAA47881PIV5         FIVVKLMPTIDSPISGCNI--TSISSYNATVTKLLQPIGENLETIRNQLIP--TRRRRR-
FUS_HRSV1B           SVITIELSNIKET--KCNGTDTKVKLIKQELDKYKNAVTELQLLMQNTPAANNRARREAP
ACO83301HRSVA2ref    SVITIELSNIKKN--KCNGTDAKIKLIKQELDKYKNAVTELQLLMQSTPATNNRARRELP
                     ::. :...*..    **   :.:. :   * :.: *    :::    .    **.

AAA47881PIV5         -----------------FAGVVIGLAALGVATAAQVTAAVALVKANENAAAILNLKNAIQ
FUS_HRSV1B           QYMNYTINTTKNLNVSISKKRKRRFLGFLLGVGSAIASGIAVSKVLHLEGEVNKIKNALL
ACO83301HRSVA2ref    RFMNYTLNNAKKTNVTLSKKRKRRFLGFLLGVGSAIASGVAVSKVLHLEGEVNKIKSALL
                                     : .: :....:  :::.:*: *.  .  . :  ::*.*:

AAA47881PIV5         KTNAAVADVVQATQSLGTAVQAVQDHINSVVSPAITAANCKAQDAIIGSILNLYLTELTT
FUS_HRSV1B           STNKAVVSLSNGVSVLTSKVLDLKNYINNRLLPIVNQSCRISNIETVTEFQQMNSRLLE
ACO83301HRSVA2ref    STNKAVVSLSNGVSVLTSKVLDLKNYIDKQLLPIVNKQSCSISN1ETVIEFQQKNNRLLE
                     .** **..:  :... * : *   :::*::. : *  .*  .:      ::   ..*

AAA47881PIV5         IFHNQITNP-ALSPITIQALRILLGSTLPTVVEKSFNTQISAAELLSSGLLTGQIVGLDL
FUS_HRSV1B           ITREFSVNAGVTTPLSTYMLTNSELLSLINDMPITNDQKKLMSSNVQIVRQQSYSIMSII
ACO83301HRSVA2ref    ITREFSVNAGVTTPVSTYMLTNSELLSLINDMPITNDQKKLMSNNVQIVRQQSYSIMSII
                     * ::  .*..  :*::       *    :*  .  :  ::  :. :.       :   :

AAA47881PIV5         TYMQMVIKIELPTLTVQPATQIIDLATISAFI--NNQEVMAQL--PTRVMVTG--SLTQA
FUS_HRSV1B           KEEVLAYVVQLPIYGVIDTPCWKLHTSPLCTTNIKEGSNICLTRTDRGWYCDNAGSVSFF
ACO83301HRSVA2ref    KEEVLAYVVQLPLYGVIDTPCWKLHTSPLCTTNTKEGSNICLTRTDRGWYCDNAGSVSFF
                      .:. ::** * :.      ::   :::: . :.     . *:

AAA47881PIV5         YPASQCTITPNTVYCRYNDAQVLSDDTMACLQGN---LTRCTFSPVVGSFLTRFVLFDGI
FUS_HRSV1B           PQADTCKVQSNRVFCDTMNSLTLPSEVSLCNTDIFNSKYDCKIMTSKTDISSSVITSLG-
ACO83301HRSVA2ref    PQAETCKVQSNRVFCDTMNSLTLPSEVNLCNVDIFNPKYDCKIMTSKTDVSSSVITSLG-
                      *. *.: .* *:*    ::  .*...:.  *  .     *.:  .    .. : .:   *

AAA47881PIV5         VYANCRS-MLCKCMQPAAVILQPSSSPVTVIDMYKCVSLQLDNLRFTITQLANVTYNSTI
FUS_HRSV1B           AIVSCYGKTKCTASNKNRGIIKTFSNGCDYVSNKGVDTVSVGNTLYYVNKLEGKNLYVKG
ACO83301HRSVA2ref    AIVSCYGKTKCTASNKNRGIIKTFSNGCDYVSNKGVDTVSVGNTLYYVNKQEGKSLYVKG
                       ...*   . *...   :   *::. *.  :.     ::::.*   : :.:  .  .

AAA47881PIV5         KLESS--QILSIDPLDISQNLAAVNKSLSDALQHLAQSDTYLSAITSATTTS--VLSIIA
FUS_HRSV1B           EPIINYYDPLVFPSDEFDASISQVNEKINQSLAFIRRSDELLHNVNTGKSTTNIMITTII
ACO83301HRSVA2ref    EPIINFYDPLVFPSDEFDASISQVNEKINQSLAFIRKSDELLHNVNAVKSTTNIMITTII
                     :       . : *  :. .:: **:.::..:* .: :**  *  .:  ..*:   ::: *

AAA47881PIV5         ICLGSLGLILIILLSVVVWKLLTIVVANRNRMENFVYHK--------------------
FUS_HRSV1B           IVIIVVLLSLIAIGLLLYCKAKNTPVTLSKDQLSGINNIAFSK-----------------
ACO83301HRSVA2ref    IVIIVILLSLIAVGLLLYCKARSTPVTLSKDQLSGINNIAFSN-----------------
                     * :   : * ** :   ::   *   . *:  :    . :   :
```

Alignment Between F Sequence of HRSV Type A and B with PIV-5 (Top Sequence) that was Used to Construct the Homology Model of Pre-Fusion RSV-F The other unstable region is the second heptad repeat (HRB) region that forms the trimeric helical stem region in pre-fusion F protein. Deletion of the transmembrane domain (TM) in the soluble F protein further destabilizes this region, which was compensated by the addition of different heterologous trimerization domains. The fully processed mature RSV-F ectodomain was fused C-terminally to different trimerization domains and at different positions (i.e., the F1 domain was truncated at different amino acid residues).

Several constructs were made based on either RSV A2 or B1 strains. Different trimerization domains were linked to the RSV F1 domain, which was truncated at different positions. Trimerization domains that were tested included the Fibritin motif (comprising the amino acid sequence: GYIPEAPRDGQAYVRKDGEWVLLSTFL (SEQ ID NO:4), and the "Fibritin long" motif, a longer, N-terminal extended Fibritin domain, which includes its natural helical regions (comprising the amino acid sequence: SSLQGDVQALQEAGYIPEAPRDGQAY-VRKDGEWVLLSTFL (SEQ ID NO:6), that were added to the RSV F1 domain in frame (in register) with the presumed heptad repeat of the HRB region.

Further constructs that were made comprised heptad ideal helical trimeric coiled coils, or Isoleucine Zipper domains (IZ) (Suzuki et al., Protein Engineering 11:1051-1055 (1998)), comprising the amino acid sequence: IEAIEKK (SEQ ID NO:7). According to the disclosure, different IZ domains were used, referred to as Isoleucine Zipper (L), comprising the amino acid sequence: (I)EKKIEAIEK-KIEAIEKKIEAIEAIEKKIEA (SEQ ID NO:8) and Isoleucine Zipper (S), comprising the amino acid sequence EKKIEAIEKKIEAIEKKIEA (SEQ ID NO:3).

These IZ domains are comparable in structure to GCN4, however, the IZ domains are not natural sequences but designed to be optimal trimerization domains and, therefore, more stable.

Further constructs were made with other known trimerization domains:

```
GCN4II
                                                        (SEQ ID NO: 9)
EDKIEEILSKIYHIENEIARIKKLIGEA

Optimized GCN4II
                                                        (SEQ ID NO: 10)
EDKVEELLSKIYHIENRIARIEKLVGEA
```

-continued

Matrilin-1 (long version)
(SEQ ID NO: 11)
EEDPCECKSIVKFQTKVEELINTLQQKLEAVAKRIEALENKII Matrillin-1 short version that only contains zipper domain:
(SEQ ID NO: 12)
EELINTLQQKLEAVAKRIEALENKII The following constructs were made:

Construct F18 comprised the Fibritin trimerization domain (SEQ ID NO:4) linked to amino acid residue 513 of the F1 domain.

Construct F19 comprised the Fibritin trimerization domain (SEQ ID NO:4) linked to amino acid residue 499 of the F1 domain.

Construct F20 comprised the Isoleucine Zipper (L) domain (SEQ ID NO:8) linked to amino acid residue 516 of the F1 domain and comprising additional modifications in HRB to optimize the hydrophobic nature of the heptad positions and facilitate in-frame fusion with the IZ domain.

Construct F21 also comprised Isoleucine Zipper (L) domain (SEQ ID NO:8), but linked to amino acid residue 501 of the F1 domain and without additional modifications in the HRB region.

Construct F22 comprised the Isoleucine Zipper (L) domain (SEQ ID NO:8) linked to amino acid residue 495 of the F1 domain and comprising additional modifications in HRB.

Construct F23 comprised the Isoleucine Zipper (S) domain (SEQ ID NO:3) linked to amino acid residue 495.

Construct F46 also comprised the Isoleucine Zipper (S) domain (SEQ ID NO:3) but linked to a longer RSV-F ectodomain, i.e., the F1 domain was truncated after amino acid residue 513.

All constructs comprised a HIS-tag.

The constructs were tested for expression levels, storage stability and antibody binding with the antibody CR9501. The amino acid sequences of the heavy and light chain variable regions, and of the heavy and light chain CDRs of this antibody are given below. CR9501 comprises the binding regions of the antibodies referred to as 58C5 in WO2012/006596.

The constructs were synthesized and codon-optimized at Gene Art (Life Technologies, Carlsbad, Calif.). The constructs were cloned into pCDNA2004 or generated by standard methods widely known within the field involving site-directed mutagenesis and PCR and sequenced. The expression platform used was the 293Freestyle cells (Life Technologies). The cells were transiently transfected using 293Fectin (Life Technologies) according to the manufacturer's instructions and cultured for 5 days at 37° C. and 10% $CO_2$. The culture supernatant was harvested and spun for 5 minutes at 300 g to remove cells and cellular debris. The spun supernatant was subsequently sterile filtered using a 0.22 µm vacuum filter and stored at 4° C. until use.

Supernatants from day 5 were evaluated for F protein expression by Western blot using the monoclonal antibody CR9503, which comprises the heavy and light chain variable regions of the RSV F antibody Motavizumab (referred to as CR9503). The approximate expression levels of the pre-fusion RSV F protein constructs were assessed using CR9503, an anti-human IR-dye conjugated secondary antibody (Li-Cor, Lincoln, Nebr.) or an HRP-conjugated mouse anti-human IgG (Jackson ImmunoResearch, West Grove, Pa.). The protein quantities were then estimated using a dilution series of purified RSV standard protein, either by eye or by using the Odyssey CLx infrared imaging system. Alternatively, Quantitative OCTET® (BioLayer Interferometry) was used for measuring protein concentration in the supernatants. To evaluate construct stability and to identify positive or negative stabilizing effects of introduced trimerization motifs, the constructs capable of binding CR9501 were treated at a range of temperatures from 45-65° C. for 30 minutes to test the stability of the CR9501 epitope. This procedure is described in detail in Example 8. The results are summarized in Table 1.

TABLE 1

Expression and stability of RSV F constructs with different trimerization motifs

| RSV Protein | Trimerization motif | Modifications | Termination point | Expression (µg/ml) | Stability* |
|---|---|---|---|---|---|
| F18 | Fibritin | None | 513 | 2 | unstable |
| F19 | Fibritin | None | 499 | 0 | ND |
| F20 | Isoleucine zipper (L) | 502 509 516 Ile | 516 | 0 | ND |
| F21 | Isoleucine zipper (L) | None | 501 | 0 | ND |
| F22 | Isoleucine zipper (L) | K483E + E488K | 495 | 0 | ND |
| F23 | Isoleucine zipper (S) | None | 495 | 0.3[1] | stable |
| F46 | Isoleucine zipper (S) | None | 513 | Did not express | ND |

*Stability is defined as described in Example 7;
ND: Not determined.
[1]Expression level determined by Western Blot as described in Example 1.

As can be seen in Table 1, the only constructs that were expressed were the Fibritin variant (F18) and F23. Although F18 was trimeric and showed expression, it was unstable upon storage at 4° C. In contrast, F23 was stable at 4° C., binds to the pre-fusion-specific antibodies, but appeared to be monomeric. Therefore, both variants F18 and F23 were used to optimize for both stability and trimerization.

Next, several constructs were made in which the fusion peptide at the N-terminus of F1 was fixed by fusion to the C-terminus of the F2 domain. All constructs comprised a His-tag.

Several constructs were made including constructs in which both furin cleavage sites were mutated resulting in a soluble F protein that still contained the p27 peptide (i.e., F12, F15.1, and F17). In other constructs, the 27-residue region (P27 loop) that is cleaved from the precursor F0 was replaced by an alternative closed loop or linking sequence: either by replacing the region of RSV-F by the "homologous" region of PIV-5 F, the pre-fusion F protein that had been produced and crystallized successfully (F25), or by replacing the region by a minimal (GS)n loop that would bridge the termini of F2 and F1 (F24), or by replacing the region by the central conserved region of RSV-G (F26). Homology modeling of RSV-F based on PIV-5 and in silico measurements resulted in the choice of a minimal loop of five amino acid residues between residues 108 and 136. As a linker, Gly (G) and Ser (S) residues were chosen, which are flexible and polar and have a high chance to be accommodated (F24). Additionally, F137 was mutated to S because the local modifications caused by the loop could displace the hydrophobic F and cause instabilities. This is shown below.

Also, the R106 is mutated to Q and 27 residues (109-135) are replaced by GSGSG (SEQ ID NO:5).

PAANNRARREAPQYMNYTINTTKNLNVSISKKRKRR₁₃₆FLGFLLGVG (SEQ ID NO: 2)

PAANNQAR GSGSGR₁₃₆SLGFLLGVG (SEQ ID NO: 17)

As shown in Table 2, all variants showed no or very low expression except for the variant with the short GSGSG loop (F24), which showed a much higher expression (44 μg/ml) compared to wild-type RSV F construct, i.e., a similar construct, without the linker (F11). F24, which was trimeric, however, was unstable upon storage like all the other variants with a C-terminal Fibritin trimerization motif. All variants contained a HIS-tag.

TABLE 2

Expression and stability of RSV F constructs with different F1-F2 linkers

| RSV Protein | Variant | Trimerization motif | F1, F2 linker | Modifications | Termination point | Expr. (μg/ml) | Stability* |
|---|---|---|---|---|---|---|---|
| F11 | B1 | None | None | None | 513 | 2.5 | stable |
| F18 | B1 | Fibritin | None | None | 513 | 2 | unstable |
| F12 | B1 | Fibritin | p27 | Furin site KO | 513 | 0.1 | unstable |
| F15.1 | B1 | None | p27 | Furin site KO | 525 | 0.5 | ND |
| F17 | A2 | Fibritin | p27 | Furin site KO | 513 | 0 | ND |
| F24 | B1 | Fibritin | Q_GSGSG_S | None | 513 | 44 | unstable |
| F25 | B1 | Fibritin | PIV | None | 513 | 0 | ND |
| F26 | B1 | Fibritin | G CR | None | 513 | 0 | ND |

Stability is defined as described in Example 7.
Expression level determined as described in Example 1.

Next, the most favorable modifications were combined to find the optimal pre-fusion F polypeptides. Combinations were made of variants with the GSGSG loop, C-terminal truncation of F1, and the addition of either fibritin (SEQ ID NO:4) or the Isoleucin Zipper (S) motif (SEQ ID NO:3) (see Table 3).

TABLE 3

Expression and stability of RSV F constructs with combinations of optimizations according to Tables 1 and 2.

| RSV Protein | Variant | Termination point | Trimerization motif | F1, F2 linker | (μg/ml) | Stability CR9501 epitope) Heat (° C.) | Storage |
|---|---|---|---|---|---|---|---|
| F11 | B1 | 513 | None | None | 2.5 | 48 | Stable |
| F23 | B1 | 495 | Isoleucine zipper (S) | None | 0.3 | ND | Stable |
| F24 | B1 | 513 | Fibritin | Q_GSGSG_S | 44 | 51 | Unstable |
| F45 | B1 | 495 | Fibritin | None | 0 | ND | ND |
| F44 | B1 | 495 | Fibritin | Q_GSGSG_S | 0 | ND | ND |
| F49 | B1 | 495 | None | None | 2 | ND | Stable |
| F50 | A2 | 495 | None | None | 2 | ND | Stable |
| F43 | B1 | 495 | Isoleucine zipper (S) | Q_GSGSG_S | 0.4 | 53 | Stable |
| F47 | A2 | 495 | Isoleucine zipper (S) | Q_GSGSG_S | 5 | 52 | Stable |
| F56 | B1 | 513 | Isoleucine zipper (S) | Q_GSGSG_S | 0.4 | ND | Stable |

TABLE 3-continued

Expression and stability of RSV F constructs with combinations of optimizations according to Tables 1 and 2.

| RSV Protein | Variant | Termination point | Trimerization motif | F1, F2 linker | (µg/ml) | Heat (° C.) | Stability CR9501 epitope) Storage |
|---|---|---|---|---|---|---|---|
| F46 | B1 | 513 | Isoleucine zipper (S) | None | 0 | ND | unstable |
| F42 | B1 | 513 | None | Q__GSGSG_S | 20 | 54 | Stable |
| F57 | A2 | 513 | None | Q__GSGSG_S | 2-10 | 54 | Stable |

ND is not determined
*Storage stability as determined in Example 7.
*Heat stability as determined in Example 8.
Expression level as determined by Western blotting (described in Example 1)

Addition of the GSGSG-loop always increased the expression of functional constructs as well as the heat stability of the protein. Combination of the GSGSG-loop with the truncated F and isoleucine zipper (S) motif (F43, F47) showed good expression, heat stability and good stability upon storage at 4° C. However, these variants were still monomeric. The isoleucine zipper (S) trimerization motif showed higher expression with an F variant that was C-terminally truncated F at position 495 (compare F43 with F56 and F23 with F46). In contrast, for variants with the Fibritin trimerization domain, a truncation at position 513 showed high expression compared to truncation at position 495, which showed no expression (compare F24 with F44).

Because the HIS-tag could interfere with the native folding of the trimers, variants were made without the HIS-tag for the Fibritin and the isoleucine zipper (S) variant (Table 4).

TABLE 4

Expression and stability of RSV F constructs with and without HIS-tag

| RSV Protein | Variant | Trimerization motif | F1, F2 linker | Termination point | Expression µg/ml | Trimerization % | Heat (° C.) | Storage | Tags |
|---|---|---|---|---|---|---|---|---|---|
| F24 | B1 | Fibritin | Q__GSGSG_S | 513 | 44 | Trimeric (SEC) | 51 | unstable | His-tag |
| F24- | B1 | Fibritin | Q__GSGSG_S | 513 | 55 | 100% (Native) | ND | unstable | None |
| F47 | A2 | Isoleucine zipper (S) | Q__GSGSG_S | 495 | 5 | 0% (Odyssey) | 52 | stable | His-tag |
| F47- | A2 | Isoleucine zipper (S) | Q__GSGSG_S | 495 | 10 | 2-5% (Odyssey) | 53 | stable | None |
| A2_F24 | A2 | Fibritin | Q__GSGSG_S | 513 | 5.3 | Trimeric (Native) | 48.75 | unstable | None |

*Storage stability determined as described in Example 7;
Heat stability determined as described in Example 8;
ND: not determined.

Strikingly, deletion of the HIS-tag increased expression in F47. Moreover, for F47, it increased the trimeric content slightly and for F24, it only increased the expression level moderately.

Next, several alternative trimerization domains and truncations were tested in combination with the GSGSG-loop stabilized F variant (F47) (see Table 5). All variants have a GSGSG-loop and contain a HIS-tag.

TABLE 5

Expression and stability of RSV F variants with alternative trimerization domains

| RSV Protein | Variant | Trimerization motif | Modifications | Termination point | Expression (µg/ml) | Trimerization % | Antibody binding CR9501 | Antibody binding CR9503 |
|---|---|---|---|---|---|---|---|---|
| F47 | A2 | Isoleucine zipper (S) | None | 495 | 5 | 0% | + | + |
| P1 | B1 | Isoleucine zipper (S) | S502T | 502 | 3.5 | 0% | + | + |
| Mat1 | A2 | Matrillin long | None | 520 | 12 | tri and hexamers | − | + |
| Mat2 | A2 | Matrillin short | None | 516 | 0 | ND | − | − |
| Mat3 | A2 | Matrillin short | None | 495 | 1.5 | ND | − | − |
| opt GCN | A2 | GCN4II optimized | None | 516 | 0 | ND | − | − |
| opt GCN + L512K | A2 | GCN4II optimized | L512K | 516 | 1 | ND | + | − |

Antibody binding is defined as binding on the day of harvest (as described in Example 7);
+ indicates binding;
− indicates no binding.
Expression level is determined as described in Example 1.
ND: not determined Only the matrillin 1 domain (Dames-S A et. al., Nat. Struc. Biol., 5(8), 1998) that contains both the N-terminal zipper domain and the C-terminal part with the cysteine residues that can potentially form inter-trimeric disulfide bridges was found to enable higher expression levels than F47 (Table 5, Matrillin long). Moreover, the variant with the Matrillin long trimerization motif shows trimeric F proteins. However, the product did not bind to the pre-fusion-specific Mab CR9501 and also showed hexameric species, which makes the Matrillin 1 trimerization domain not suitable for production of trimeric native F protein. None of the matrillin-based or the GCN4II-based zipper motifs showed increased expression or stability relative to F47 (Table 5, Matrillin short, GCN4II optimized). Again, truncation at 495 results in higher expression levels. Addition of a GCN4 motif, which contained an optimized trigger sequence, showed no expression.

GCN4II is a trimerization domain that is used successfully for stabilizing the pre-fusion trimer of parainfluenza type 5 (Yin et al., Nature 439:38-44, 2006) and has also been tried by others to stabilize RSV pre-fusion F (as disclosed in, e.g., WO2010/149743, WO2010/14975, WO2009/079796, and WO2010/158613). The GCN4II trimerization domain was evaluated and compared with the constructs that contain the Isoleucine Zipper (S) domain (SEQ ID NO:3) or the Fibritin (SEQ ID NO:4) domain (results shown in Table 6). These variants were also compared with other modifications, i.e., a short linker based on a single Lysine and the L512K mutation. All variants contained a HIS-tag.

TABLE 6

Expression and stability of RSV F variants with GCN4II, L512K and p27 replacement (single amino acid linker (K) between F1 and F2)

| RSV Protein | Variant | Trimerization motif | F1, F2 linker | Modifications | Termination point | Expr. (µg/ml) | Stability Heat (° C.) | Stability Storage* |
|---|---|---|---|---|---|---|---|---|
| F18 | B1 | Fibritin | None | None | 513 | 2 | ND | unstable |
| F24 | B1 | Fibritin | Q_GSGSG_S | None | 513 | 44 | 51 | unstable |
| F43 | B1 | Isoleucine zipper (S) | Q_GSGSG_S | None | 495 | 0.4 | 53 | stable |
| P1 | B1 | Isoleucine zipper (S) | Q_GSGSG_S | S502T | 502 | 3.5 | 54 | ND |
| F42 | B1 | None | Q_GSGSG_S | None | 513 | 16.1 | 54 | stable |
| P2 | B1 | None | K | None | 513 | 14.3 | 54 | stable |

TABLE 6-continued

Expression and stability of RSV F variants with GCN4II, L512K and p27 replacement (single amino acid linker (K) between F1 and F2)

| RSV Protein | Variant | Trimerization motif | F1, F2 linker | Modifications | Termination point | Expr. (μg/ml) | Heat (° C.) | Storage* |
|---|---|---|---|---|---|---|---|---|
| P3 | B1 | GCN4II | None | L512K | 516 | 0 | ND | ND |
| P4 | B1 | GCN4II | K | L512K | 516 | 0 | ND | ND |
| P5 | B1 | GCN4II | K | L512K | 516 | 0 | ND | ND |
| P6 | A2 | GCN4II | K | L512K | 516 | 0 | ND | ND |
| P7 | A2 | GCN4II | K | L512K | 516 | 0 | ND | ND |

Storage stability determined as described in Example 7;
Expression levels determined as described in Example 1;
Heat stability determined as described in Example 8;
ND: not determined.

The short linkage between F1 and F2 appears to be comparable to the GSGSG loop. Addition of the GCN4II motif does not result in any F protein expression in any of the constructs (i.e., the RSV A2 F sequence described in WO2010/149743 or WO2010/149745, the RSV A2 F sequence used according to the disclosure, nor the RSV B1 F sequence).

It was shown according to the disclosure that the introduction of these two types of modifications, i.e., introduction of a linking sequence and the heterologous trimerization domain, was not enough to enable the expression of stable trimeric pre-fusion F protein. Apart from the two main regions of instability that were stabilized, i.e., the HRB and the fusion peptide, as described above, other regions in the pre-fusion F protein also contribute and/or accommodate the dramatic refolding to post-fusion F, and more positions in the sequence can be optimized to stop the pre-fusion F protein from refolding. Therefore, different amino acid residues in the HRA and HRB domain and in all domains that contact these regions in pre-fusion F were mutated to increase the pre-fusion structure stability, as described in the following Examples.

Example 2: Preparation of Stable Pre-Fusion RSV F Polypeptides—Stabilizing Mutations Because the trimeric content (for construct F47) and storage stability (for construct F24) was not optimal, further variants were made that contained point mutations to increase expression levels, stability and native trimeric structure. The results are shown in Tables 7 and 8.

TABLE 7

Expression and stability of F47- variants

| RSV Protein | Expression (ug/ml) | Trimerization % | Heat (° C.) |
|---|---|---|---|
| F47- | 10 | 2-5% | 53 |
| F47- + K465E | 6 | 2.4% | ND |
| F47- + D479K | 5 | 29% | 50.77 |
| F47- + K176M | 13 | 5% | ND |
| F47- + K209Q | 9 | 3% | 52.9 |
| F47- + S46G | 38 | 11% | 59.38 |

TABLE 7-continued

Expression and stability of F47- variants

| RSV Protein | Expression (ug/ml) | Trimerization % | Heat (° C.) |
|---|---|---|---|
| F47- + S215P | 8 | 1-2% | 57.21 |
| F47- + N67I | 15 | 2% | 59.84 |
| F47- + K465Q | 18 | 2% | 54.3 |
| F47- S46G + N67I | 31 | 6% | >60 |
| F47- S46G + S215P | 38 | 6% | >60 |
| F47- K465Q + K209Q | 12 | 1% | 53.3 |
| F47- K465Q + S46G | 28 | 7% | 57.7 |
| F47- K465Q + N67I | 17 | 2% | 59 |
| F47- K209Q + N67I | 15 | 4% | >60 |
| F47- K209Q + S215P | 15 | 2% | 56.7 |

ND: not determined;
Expression level determined as described in Example 1.
Heat stability determined as described in Example 8.

Nomenclature of mutations based on wt sequence (SEQ ID NO:1).

All constructs are variants of F47-: type A2, Isoleucine Zipper (S) motif (SEQ ID NO:3), GSGSG linker; termination point 495, no HIS-tag (SEQ ID NO:16). As shown in Table 7, many mutations increased the expression of F47-, but only the variant F47_S46G also showed a higher level of trimers besides the high expression.

Table 8 shows the results of the expression and stability of F24 variants. All variants were of RSV type A2, with fibritin motif, GSGSG linker; termination point 513, no HIS-tag.

TABLE 8

Expression and stability of A2_F24- (SEQ ID NO: 19) variants

| RSV Protein | Expression (μg/ml) | Storage Endpoint | Association phase |
|---|---|---|---|
| A2_F24 | 5.3 | 69 | ND |
| A2_F24 K508E | 5.3 | 64 | ND |
| A2_F24 K498E | 1.7 | ND | ND |
| A2_F24 E487I | 25.0 | 10 | ND |
| A2_F24 E487K | 7.1 | ND | ND |
| A2_F24 E487N | 42.4 | 22 | ND |

TABLE 8-continued

Expression and stability of A2_F24- (SEQ ID NO: 19) variants

| RSV Protein | Expression (μg/ml) | Storage Endpoint | Association phase |
|---|---|---|---|
| A2_F24 E487P | 12.8 | 46 | ND |
| A2_F24 E487Q* | 14.8 | 50 | ND |
| A2_F24 E487R | 8.7 | 59 | ND |
| A2_F24 E487S | 6.7 | 46 | ND |
| A2_F24 E487Y | 10.5 | 36 | ND |
| A2_F24 D486N | 31.2 | 19 | ND |
| A2_F24 D479N | 5.2 | ND | ND |
| A2_F24 D479K | 1.5 | 62 | ND |
| A2_F24 E472Q | 1.9 | ND | ND |
| A2_F24 E472K | 0.9 | ND | ND |
| A2_F24 K465E | 14.8 | 76 | ND |
| A2_F24 K465Q* | 13.6 | 92 | Not stable |
| A2_F24 E463K | 3.1 | ND | ND |
| A2_F24 E463Q | 6.0 | ND | ND |
| A2_F24 G430S | 4.8 | ND | ND |
| A2_F24 N428R | 5.2 | 35 | ND |
| A2_F24 N426S | 18.6 | 71 | ND |
| A2_F24 K421N | 9.2 | 75 | ND |
| A2_F24 E328K | 9.5 | 21 | ND |
| A2_F24 T311S | 3.5 | 70 | ND |
| A2_F24 I309V | 11.3 | 69 | ND |
| A2_F24 D269V | 0.0 | ND | ND |
| A2_F24 S215P* | 18.7 | 99 | Stable |
| A2_F24 K209Q | 31.4 | 63 | ND |
| A2_F24 V207P | 3.3 | 79 | ND |
| A2_F24 I206P | 5.4 | 55 | ND |
| A2_F24 L204P | 5.9 | ND | ND |
| A2_F24 L203P | 0.8 | ND | ND |
| A2_F24 Q202P | 4.4 | ND | ND |
| A2_F24 K201Q | 21.3 | 62 | ND |
| A2_F24 D194P | 1.9 | ND | ND |
| A2_F24 L193P | 6.5 | 42 | ND |
| A2_F24 V192P | 0.6 | 32 | ND |
| A2_F24 V185N | 50.2 | 38 | ND |
| A2_F24 GV184EG | 3.5 | ND | ND |
| A2_F24 G184N | 59.8 | 37 | ND |
| A2_F24 V178P | 14.8 | 23 | ND |
| A2_F24 A177P | 2.0 | ND | ND |
| A2_F24 K176M | 14.7 | 58 | ND |
| A2_F24 K176E | 0.7 | ND | ND |
| A2_F24 N175P | 34.3 | 55 | ND |
| A2_F24 S169P | 0.5 | ND | ND |
| A2_F24 K168P | 0.1 | ND | ND |
| A2_F24 K166P | 12.3 | 45 | ND |
| A2_F24 V157P | 0.2 | ND | ND |
| A2_F24 E92D | 47.4 | 94 | Not stable |
| A2_F24 K85E | 1.1 | ND | ND |
| A2_F24 K80E | 51.9 | 60 | ND |
| A2_F24 K77E | 22.4 | ND | ND |
| A2_F24 N67I* | 89.8 | 101 | Stable |
| A2_F24 I57V | | ND | ND |
| A2_F24 VI56IV | 16.5 | 54 | ND |
| A2_F24 S46G* | 40.7 | 96 | Not stable |

The *marked constructs were tested for trimerization and were all found to be trimeric
Expression level determined as described in Example 1.
Endpoint stability is shown here as the percentage of pre-fusion antibody binding (CR9501) after 5 days of storage at 4° C. relative to day 1;
Association phase stability is determined as described in Example 9.

Many mutations increased the expression of A2_F24–. For most mutations, there was an apparent correlation between improved expression in F47– background (Table 7) and A2_F24– background (Table 8). N67I had more positive impact on F expression in A2_F24– background. The most significant increase in expression was obtained with the single point mutations: S46G, S215P, N67I, K80E, E92D, D486N, G184N, V185N, E487N, N175P, K209Q, E487I, E487Q, K77E, K201Q, N426S and K465Q. In the initial screening using the endpoint stability assay (Example 7), the variants with the highest expression showed the best stability upon storage as well (E92D, K465Q, K465E, N426S, S46G, S215P and N67I). To evaluate if these mutations indeed were stabilizing the pre-fusion conformation, culture supernatants were diluted to 5 and 10 μg/ml based on quantitative Western results and these were stored up to 33 days at 4° C. As single point mutants, only N67I and S215P were completely stable over time (see Example 9).

Subsequently, several mutations that showed high expression and good stability of the pre-fusion conformation were combined to evaluate whether the stabilizations were additive or had a possible synergistic effect (Table 9).

TABLE 9

Expression and stability of variants of A2_F24 with two additional mutations.

| RSV Protein | Expression (μg/ml) | stability* |
|---|---|---|
| A2_F24 K465Q + S46G | 21.8 | Not stable |
| A2_F24 K465Q + N67I | 122.3 | Stable |
| A2_F24 K465Q + E92D | 10.5 | Stable |
| A2_F24 K465Q + S215P | 59.8 | Stable |
| A2_F24 S46G + N67I | 115.5 | Stable |
| A2_F24 S46G + E92D | 14.3 | Not stable |
| A2_F24 N67I + E92D | 134.2 | Stable |
| A2_F24 N67I + S215P | 152.1 | Stable |
| A2_F24 E92D + S215P | 49.1 | Stable |
| A2_F24 K465Q + S215P | 53.3 | Stable |
| A2_F24 S46G + S215P | 43.8 | Stable |

Storage stability refers to the association phase analysis illustrated in Example 9.
Expression level was determined as described in Example 1.

All variants are variants of F24–: type A2, fibritin motif, GSGSG linker; termination point 513, binding to all Mabs, no HIS-tag (SEQ ID NO:19).

When the previously identified point mutations were combined, very interesting synergistic effects could be observed, especially in terms of expression levels with the combinations involving N67I as the most potent. All produced double mutants where either N67I or S215P was included and were stable after more than 30 days storage at 4° C. (Example 9). Strikingly, the mutation N67I was found to have the strongest effect on expression levels of pre-fusion F when included in the double mutants. Next, combinations with the S215P mutations resulted in a reasonable expression. Combination of N67I with S215P was selected since it led to a very high expression level, and because both point mutations were stable upon storage. Additionally, it was observed that both N67I and S215P had the ability to stabilize some of the mutants that, as single mutations, were unstable, indicating that the region where these two mutations are found is central for the conformation changes the protein undergoes during the transition to the post-fusion conformation.

According to the disclosure, it thus has been shown that at least some mutations resulted in increased expression levels and increased stabilization of the pre-fusion RSV protein. It is expected that these phenomena are linked. The mutations described in this example all resulted in increased production of pre-fusion F polypeptides. Only a selection of these polypeptides remained stable upon long storage (see Example 9). The stability assay that was used is based on the loss of the pre-fusion-specific CR9501 epitope in the top of the pre-fusion F protein in a binding assay and it may not be sensitive enough to measure all contributions to stability of the whole protein. The mutations for which only increased expression is observed and are, therefore, (very likely stabilizing) potential mutations that can be combined with other stabilizing mutations to obtain a pre-fusion F construct with high stability and high expression levels.

Next, it was verified whether the N67I-S215P double mutation, like the single mutations, was able to stabilize point mutations that as single mutants were deemed unstable based on the criteria used. Extra mutations were selected based on the favorable expression levels and stability according to Table 8. Triple mutant RSV-F variants were constructed and tested for expression levels and stability (Table 10).

TABLE 10

Expression and stability of variants of F24_N67I + S215P with one additional mutation.

| RSV Protein | Expression (μg/ml) | stability* |
|---|---|---|
| A2_F24 N67I + S215P + K507E | 344.6 | ++ |
| A2_F24 N67I + S215P + E487I | 239.4 | +++ |
| A2_F24 N67I + S215P + E487N | 285.2 | +++ |
| A2_F24 N67I + S215P + E487Q | 360.7 | +++ |
| A2_F24 N67I + S215P + E487R | 130.9 | +++ |
| A2_F24 N67I + S215P + D486N | 292.6 | +++ |
| A2_F24 N67I + S215P + D479N | 97.1 | +++ |
| A2_F24 N67I + S215P + K465Q | 283.3 | +++ |
| A2_F24 N67I + S215P + N426S | 316.3 | +++ |
| A2_F24 N67I + S215P + K421N | 288.4 | +++ |
| A2_F24 N67I + S215P + K209Q | 245.0 | +++ |
| A2_F24 N67I + S215P + K201Q | 231.9 | +++ |
| A2_F24 N67I + S215P + V185N | 445.1 | +++ |
| A2_F24 N67I + S215P + G184N | 326.7 | +++ |
| A2_F24 N67I + S215P + E92D | 308.8 | + |
| A2_F24 N67I + S215P + K80E | 210.6 | + |
| A2_F24 N67I + S215P + S46G | 199.4 | +++ |

All variants are variants of A2_F24_N67I + S215P type A2, fibritin motif, GSGSG linker; termination point 513, binding to all Mabs, no HIS-tag (SEQ ID NO: 21).
*stability refers to the association phase analysis illustrated in Example 9.
+ means <10% loss of CR9501 binding after 5 days;
++ means <5% loss of CR9501 binding after 5 days;
+++ means 0% loss of CR9501 binding after 5 days.

Again, an additive effect on the expression levels was observed. As expected D479N and E487R triple mutants express at somewhat lower levels because the single mutants were also among the lowest of the selected mutations (Table 8). Because of the stabilizing effect of the N67I+S215P mutation, additional mutations that are unstable as single mutants resulted in stable pre-fusion F variants when they were added to the A2_F24 N67I+S215P background. Some very illustrative examples are the triple mutants with the additional V185N, G184N or E487N, which showed high expression but low stability as single mutants (Table 8) but showed even higher expression and were highly stable when added to the A2_F24 N67I+S215P background.

Stabilizing Mutations Also Stabilize RSV-F Protein from Other Strains and Also in Processed F Variant.

Several mutations that showed high expression and good stability of the pre-fusion conformation were applied to RSV F proteins of other strains (SEQ ID NOS:69 and 70) and were applied to an RSV A2 F variant without furin cleavage site mutations (F18: SEQ ID NO:71) to evaluate whether the modifications are a universal solution to stabilize RSV pre-fusion F (Table 11).

TABLE 11

Expression and stability of variants of A2_F18 with additional mutations and F from strain B1 (SEQ ID NO: 2) and type A CL57-v224 (SEQ ID NO: 69).

| RSV protein | Seq ID | Relative* expression (CR9503) | Stability** after day 5, % |
|---|---|---|---|
| A2_F18 | 71 | 0.018 | 0.0 |
| A2_F18 N67I | | 0.449 | 73.2 |
| A2_F18 S215P | | 0.129 | 9.1 |
| A2_F18 E487Q | | 0.006 | NA |
| A2_F18 N67I, S215P | 72 | 0.484 | 103.4 |
| A2_F18 N67I, E487Q | | 0.340 | 92.1 |
| A2_F18 N67I, S215P, E487Q | 76 | 0.355 | 92.7 |
| A2_F18 N67I, S215P, E92D | 78 | 0.318 | 96.0 |
| A2_F18 N67I, S215P, D486N | 79 | 0.522 | 101.3 |
| A2_F18 N67I, S215P, K201N | 77 | 0.643 | 102.7 |
| A2_F18 N67I, S215P, K66E | | 0.800 | 103.0 |
| A2_F18 N67I, S215P, S46G, K66E | | 0.820 | 103.5 |
| A2_F18 N67I, S215P, E487Q, K66E | | 0.704 | 99.5 |
| A2_F18 N67I, S215P, E92D, K66E | | 0.905 | 98.8 |
| A2_F18 N67I, S215P, D486N, K66E | | 0.863 | 96.6 |
| A2_F18 N67I, S215P, K201N, K66E | | 1.021 | 105.5 |
| A2_F18 N67I, S215P, D486N, K66E, I76V | | 0.594 | 95.0 |
| B1_N67I, S215P | 73 | 0.434 | 90.9 |
| B1_N67I, S215P loop | 22 | 0.552 | 108.2 |
| CL57v224_N67I, S215P | 74 | 0.698 | 94.9 |
| CL57v224_N67I, S215P loop | 75 | 0.615 | 98.4 |

Protein expression (concentration in the supernatant of transiently transfected cells) was measured by Quantitative OCTET ® method.
*Relative expression is normalized to expression of A2_F24_N67I, S215P, E487Q (seq ID NO: 33)
**Stability - is expressed as % protein concentration measured after storage at 4° C. for 5 days, relative to the day of harvest. The concentrations were measured by Quantitative OCTET ® method using CR9501 antibody.
NA—data not available: no CR9501 binding was detected.

When the previously identified point mutations were introduced in A2_F18 (SEQ ID NO:71), the stability and expression levels were very similar compared with the single chain F24 (SEQ ID NO:21) variant that contained a short loop between F1 and F2. Again, synergism was observed showing higher expression and stability when mutations were added to variants that contained the N67I or the double mutation N67I, S215P. The double-point mutation N67I, S215P did not only stabilize the pre-fusion F of the A2 strain but also pre-fusion of the B1 and CL57-v224 strains (Table 11).

Stabilizing Mutations Also Stabilize Full-Length RSV-F Protein.

Several mutations that showed high expression and good stability of the pre-fusion conformation in the soluble version of RSV-F corresponding to the ectodomain were applied to the full-length RSV-F protein. The mutations were introduced in full-length RSV-F with or without furin cleavage site mutations. No trimerization domain was fused to these variants (Table 12)

TABLE 12

Expression and stability of variants of full-length versions of A2_F18 and A2_F24 with additional mutations.

| RSV F protein variant* | | | Attributes | |
|---|---|---|---|---|
| Amino acid substitutions | SEQ ID No | F1, F2 linker | Expression, fold increase** | Heat-stability*** |
| None (F A2 wildtype, full length) | 1 | none | 1 | - |
| N67I | | none | 1.4 | N.D. |
| S215P | | none | 1.4 | N.D. |
| E92D | | none | 1.4 | N.D. |
| N67I, K465Q | | none | 1.4 | N.D. |
| N67I, S46G | | none | 0.2 | N.D. |
| N67I, E92D | | none | 1.4 | N.D. |
| N67I, K80E | | none | 2.3 | N.D. |
| N67I, G184N | | none | 1.5 | N.D. |
| N67I, V185N | | none | 1.4 | N.D. |
| N67I, E487Q | | none | 2.5 | N.D. |
| N67I, S215P, V185N | | none | 2.7 | N.D. |
| N67I. S215P, K508E | | none | 3.0 | N.D. |
| N67I, S215P, K80E | | none | 3.1 | N.D. |
| N67I, S215P, K465Q | | none | 2.9 | N.D. |
| N67I, S215P | 80 | none | 2.4 | ++ |
| N67I, S215P, G184N | | none | 7.6 | ++ |
| N67I, S215P, E92D | 82 | none | 6.8 | N.D. |
| N67I, S215P, S46G | 88 | none | 6.8 | + |
| N67I, S215P, D486N | 86 | none | 5.9 | +++ |
| N67I, S215P, E487Q | 84 | none | 6.2 | N.D. |
| N67I, S215P, S46G, K66E | | none | 12.1 | +++ |
| N67I, S215P, D486N, K66E | | none | 9.2 | +++ |
| N67I, S215P, S46G, E92D, K66E | | none | 11.8 | +++ |
| N67I, S215P, S46G, E487Q, K66E | | none | 11.0 | +++ |
| N67I, S215P, S46G, D486N, K66E | | none | 10.5 | +++ |
| N67I, S215P, D486N, K66E, I76V | | none | 7.2 | +++ |
| N67I, S215P, S46G, K66E, I76V | | none | 9.7 | +++ |
| N67I, S215P, S46G, K80E | | none | 4.5 | N.D. |
| N67I + S215P + G184N + K80E + E92D + E487Q + S46G | | none | 9.1 | N.D. |
| None | | Q__GSGSG_S | 3.8 | - |
| N67I, S215P | 81 | Q__GSGSG_S | 6.2 | N.D. |
| N67I, S215P, G184N | | Q__GSGSG_S | 7.2 | ++ |
| N67I, S215P, E92D | 83 | Q__GSGSG_S | 5.9 | N.D. |
| N67I, S215P, S46G | 89 | Q__GSGSG_S | 5.3 | ++ |

TABLE 12-continued

Expression and stability of variants of full-length versions of A2_F18 and A2_F24 with additional mutations.

| Amino acid substitutions | RSV F protein variant* SEQ ID No | F1, F2 linker | Attributes Expression, fold increase** | Heat-stability*** |
|---|---|---|---|---|
| N67I, S215P, D486N | 87 | Q__GSGSG_S | 5.2 | +++ |
| N67I, S215P, E487Q | 85 | Q__GSGSG_S | 4.6 | N.D. |
| N67I, S215P, S46G, K66E | | Q__GSGSG_S | 11.7 | +++ |
| N67I, S215P, D486N, K66E | | Q__GSGSG_S | 13.8 | +++ |
| N67I, S215P, D486N, K66E, I76V | | Q__GSGSG_S | 6.8 | +++ |
| N67I + S215P + G184N + K80E + E92D + E487Q + S46G | | Q__GSGSG_S | 3.6 | N.D. |

Expression level determined using FACS.
N.D.- not determined.
*all variants are based on RSV A2 F protein sequence.
**comparing to wild-type protein, fold increase of MFI on 9503.
Stability was assessed by heat treatment of the HEK293T cells for 5-10 minutes at 46, 55.3, 60° C.
***legend for the stability readout
- decrease in binding to pre fusion-specific Mab CR9501 binding after 46° C. (e.g., wild-type)
+ slight decrease of CR9501 binding after 46° C., but not to same strong extent as wild-type
++ no change in CR9501 binding up to 60° C.; at 60° C., some decrease in CR9501 binding
+++ no change in CR9501 binding at 60° C.

The previously identified stabilizing point mutations were also stabilizing in the full-length F protein. The increase in expression level was less pronounced but showed the same trend. This may be caused by the different background the mutations were introduced in but may also be caused by the different quantification method (FACS versus Western blot) and a biological maximum of expression due to recycling of surface proteins. Introduction of the linking sequence (or short loop) increased expression and stability and the point mutations did so too. The point mutations were not or hardly synergistic with the short loop (similar as to what was found for the soluble protein (Tables 9-11).

Because the point mutation at position 67 had such a positive effect on expression level and stability, all amino acid substitutions were tested for this position to study whether the most optimal were chosen or whether these positions can be improved (Table 13).

TABLE 13

Full substitution analysis of expression and stability for position 67 in the A2_F24 background.

| Amino acid substitution | Relative Expression* | Stability** after day 4, % | Stability** after day 10, % |
|---|---|---|---|
| N67A | 1.696 | 0.0 | 0.0 |
| N67C | 1.759 | 16.7 | 0.0 |
| N67D | 1.702 | 0.0 | 0.0 |
| N67E | 1.357 | 0.0 | 0.0 |
| N67F | 2.565 | 102.2 | 108.1 |
| N67G | 0.853 | NA | NA |
| N67H | 1.509 | 0.0 | 0.0 |
| N67I | 3.773 | 98.2 | 102.7 |
| N67K | 0.487 | NA | NA |
| N67L | 3.609 | 107.5 | 96.4 |
| N67M | 2.579 | 87.3 | 78.7 |
| N67P | 2.414 | 14.3 | 0.0 |
| N67Q | 0.955 | NA | NA |

TABLE 13-continued

Full substitution analysis of expression and stability for position 67 in the A2_F24 background.

| Amino acid substitution | Relative Expression* | Stability** after day 4, % | Stability** after day 10, % |
|---|---|---|---|
| N67R | 0.523 | NA | NA |
| N67S | 1.277 | 0.0 | 0.0 |
| N67T | 1.577 | 0.0 | 0.0 |
| N67V | 2.457 | 84.2 | 77.0 |
| N67W | 1.794 | 99.9 | 104.3 |
| N67Y | 1.830 | 61.3 | 45.8 |

*Relative expression - protein concentration was measured by Quantitative OCTET® method using CR9503 antibody and expressed relative to concentration of A2_F24 (SEQ ID NO: 19)
**Stability - is expressed as % protein concentration measured after storage at 4° C. for 5 and 10 days, relative to the day of harvest. The concentrations were measured by Quantitative OCTET® method using CR9501 antibody.
NA—data not available: no CR9501 binding was detected.

As shown in Table 13, primarily hydrophobic residues and, particularly, Ile, Leu and Met at position 67, were able to increase expression and stability. Ile is the residue that increased expression and stability most. Residues Glu and Gln, the smallest residue Gly, and the positively charged residues Arg and Lys, had the most destabilizing effect at position 67 on the pre-fusion conformation.

According to the disclosure, the amino acid mutations that stabilize the pre-fusion conformation of the RSV F protein can be grouped into different categories that stabilize the conformation in different manners. The strategies for pre-fusion F stabilization are based on the homology model of RSV-F that was based on the PIV-5 crystal structure (Yin et. al., 2006) and the alignment on page 27.

Amino Acid Residues 67 and 215:

The amino acid residues at positions 67 and 215 are very close in the three-dimensional structure of both the pre-fusion model and the post-fusion crystal structure. The residues are close to the conserved disulfide bridge in the top of the DIII region that forms the hinge along which the HRA region refolds into the long-elongated coiled coil-extended helical trimer. Mutations in this region will influence the hinge function and, therefore, the mutations that were introduced stabilize the pre-fusion conformation by obstruction of the hinge function.

Amino Acid Residues 77, 80

The amino acid residues at positions 77 and 80 are located within the long helix (residues 76-98) at the C-terminus of F2 that is in close contact to the ensemble of secondary structures in DIII at the N-terminus of F1 that refold into the long-coiled coil structure of the post-fusion conformation. Since these two regions have to be separated during the refolding from pre- to post-fusion, amino acids in this region that prevent this separation would stabilize the pre-fusion conformation. Because these two regions should part during refolding, some of the residues can be optimized to strengthen the interaction. An example of a repulsion that was observed was between the positively charged Lys80. Mutation of Lys80 to the negatively charged Glu residue increased the expression of pre-fusion F. Due to the sequential transition to the post-fusion conformation, these mutations can be combined with other stabilizing mutations like N67I and S215P to get the full benefit of this stabilization, as shown in Table 10.

Amino Acid Residue 92

The amino acid residue at position 92 is also located within the long helix (residues 76-98) at the C-terminus of F2 that is in close contact to the ensemble of secondary structures in DIII at the N-terminus of F1 that refold into the long-coiled coil structure of the post-fusion conformation. When this helix is separated from the HRA region, it is pulled to the DIII region that contains the Synagis epitope (epitope II) (Arbiza et al., J. Gen. Virol. 73:2225-2234, 1992) and the negatively charged Glu92 moves very close to the positively charged Arg282 in the post-fusion conformation. Mutations that reduce this pull will stabilize the pre-fusion conformation. Mutation of Glu92 to a conserved Asp residue will reduce the pull because it is not able to reach Arg282.

Amino Acid Residues 486, 487

The amino acid residues 486, 487 and 489 at the top of HRB in the pre-fusion conformation form a negatively charged patch mutation of Glu487 to Asn or Ile increased pre-fusion F expression. Mutations of Asp486 into Asn or Gln and/or Glu489 into Asn, Ile or Gln will have the same effect. Due to the sequential transition to post-fusion, these mutations can be combined with other stabilizing mutations like N67I and S215P to get the full benefit of this stabilization, as shown in Table 10 for, e.g., D486N.

Amino Acid Residues 175, 184, 185

In order to refold from the pre-fusion to the post-fusion conformation, the region between residue 175 and 193 has to transform from a loop—beta hairpin to a helix.

This region demonstrates the most dramatic structural transition. Part of this region actually has the highest alpha-helix prediction. The actual helical structures in the pre-fusion model are shown below underlined. This whole region is transformed into one large helix when it refolds to the post-fusion conformation. In the bottom sequence, the residues are underlined with the highest helix prediction based on Agadir (http://agadir.crg.es/). It is clear from this comparison that the C-terminal part that is maintained in a beta-hairpin in the pre-fusion conformation (residues 187-202) has a high tendency to form an alpha-helix.

```
         150       160       170       180       190       200       210
                                                                  (SEQ ID NO: 1)
         SGVAVSKVLHLEGEVNKIKSALLSTNKAVVSLSNGVSVLTSKVLDLKNYIDKQLLPIVNKQSC hhhhhh    hhhhhhh   hhhhh    sssssss   sssssss  hhhhhhhh (SEQ ID NO: 1)
         SGVAVSKVLHLEGEVNKIKSALLSTNKAVVSLSNGVSVLTSKVLDLKNYIDKQLLPIVNKQSC
```

The sequence of residues 150-212 of RSV-F (SEQ ID NO:1) is shown above. On the second line, the secondary structures of the top line are indicated by h (for helix) and s (for strands) based on the PIV-5 3D homology model. Helices are underlined. The bottom line is the same sequence in which the helices are underlined based on the helix propensity of the sequence.

Therefore, a Proline was introduced at position 175 to stabilize this turn and to prevent refolding into a helix, which, as a single mutation, increased the expression level, indicating that it stabilizes the pre-fusion conformation and enables better processing of the protein. For the turn in the hairpin (residues 184, 185), the Brookhaven database was searched for a structurally homologous hairpin from a stable protein that does not refold. A high structural homology was discovered with a hairpin loop in Protein Kinase A (pdb code 3FHI). According to the alignment shown below, residues 184Gly or 185Val were replaced by Asn in order to stabilize this turn and prevent it from refolding.

```
                                        (SEQ ID NO: 1)
         VVSLSNGVSVLTSKV     HRAb1b2 178-192

(SEQ ID NO: 97)
         EMDVYVNNEWATSVG     3fhi:B 179-193
```

These mutations can be combined with other stabilizing mutations like N67I and S215P to get the full benefit of this stabilization as shown in Table 10.

Amino Acid Residues 421, 426 and 46

The amino acid residues at positions 421 and 426 are in a loop in the DII region. Residue S46 is on a strand that crosses from DI to DIII. The amino acid residue at position 426 was mutated into serine and the amino acid residue at position 46 was mutated into glycine. These mutations increased stability and pre-fusion expression levels.

Amino Acid Residue 465

The amino acid residue Lys465 is located in another region that goes through a large conformational change. Lys465 is located on a cross-over loop that connects the top of the DII region to HRB. Because the HRB region moves up from the bottom to the top and complexes with HRA to make the six-helix bundle, the cross-over loop also relocates from bottom to top. This loop must, therefore, be metastable in order to allow detachment of DII and reposition in another environment. Lys465 on the cross-over loop is close to Lys445 on the DII region. Mutation of Lys465 to either Gln or Glu neutralizes the repulsion and increased stability and pre-fusion F expression levels.

Example 3: Expression of Pre-Fusion F Protein

Figure 4A:
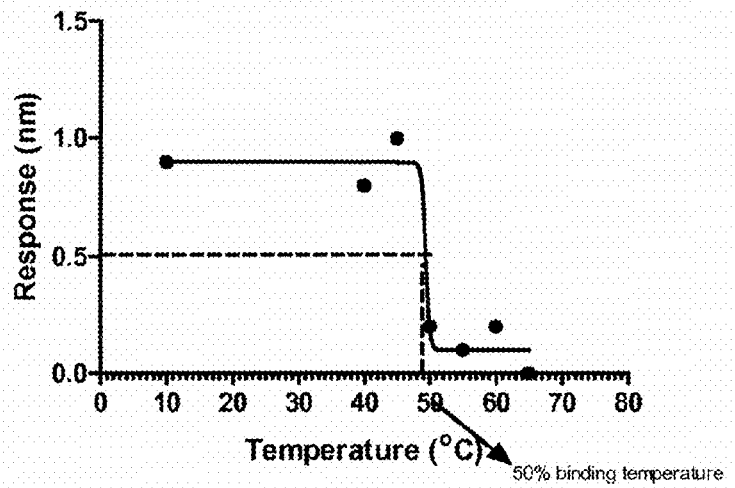
FIGS. 4A and 4B: shows the results of the method described in Example 6.
Figure 4B:
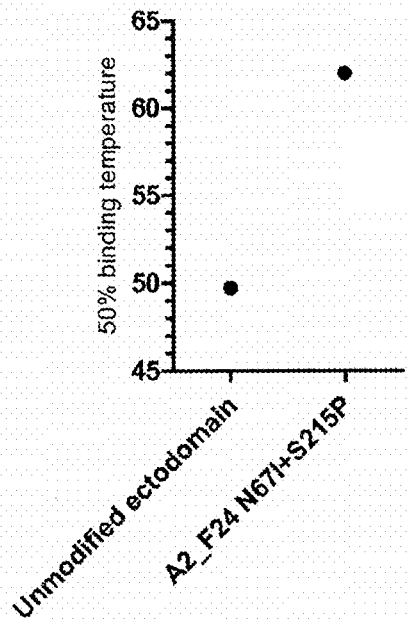
Figure 5A:
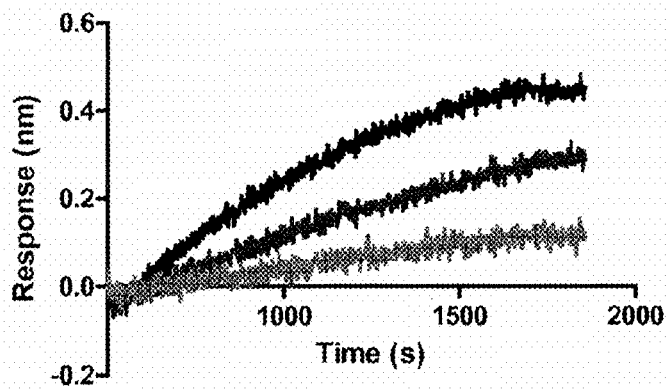
FIGS. 5A-5E: OCTET® measurements showing the storage-time-dependent loss of binding of the pre-fusion-specific antibody CR9501 to the pre-fusion constructs.
Figure 5B:
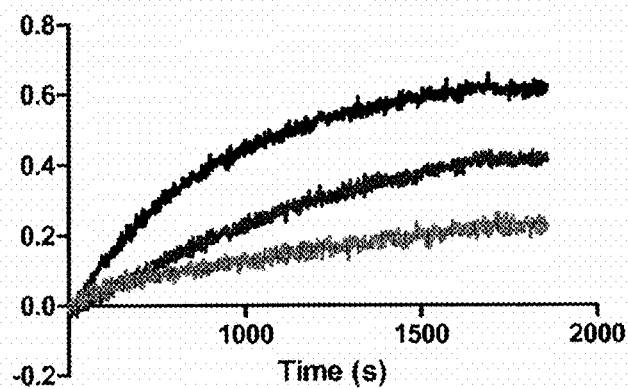
Figure 5C:
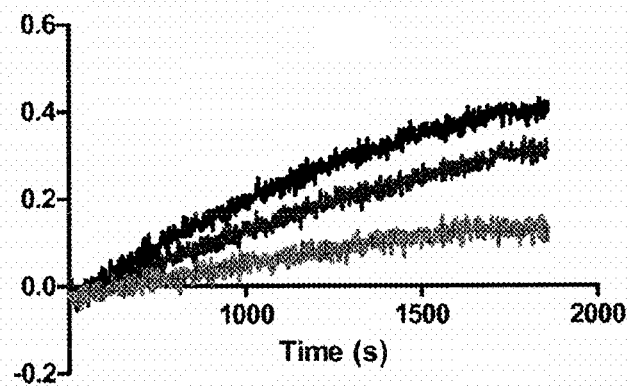
Figure 5D:
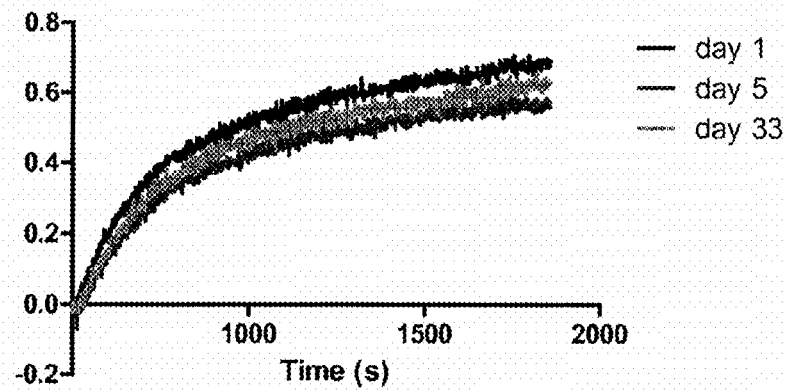
Figure 5E:
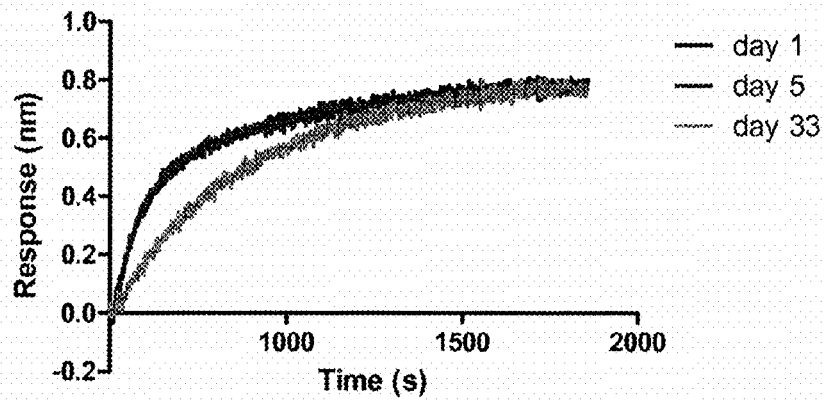
Figure 6A:
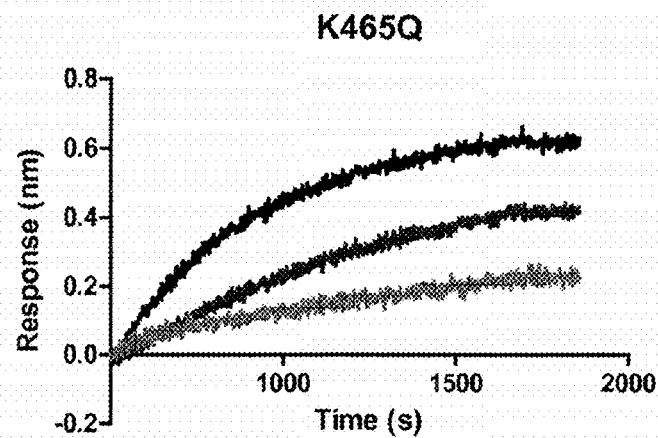
FIGS. 6A-6I: OCTET® measurements showing the storage-time-dependent loss of binding of the pre-fusion-specific monoclonal antibody CR9501 to the pre-fusion constructs.
Figure 6B:
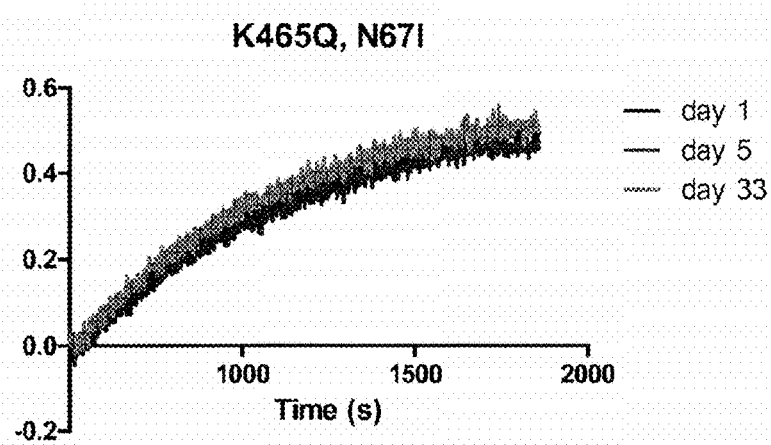
Figure 6C:
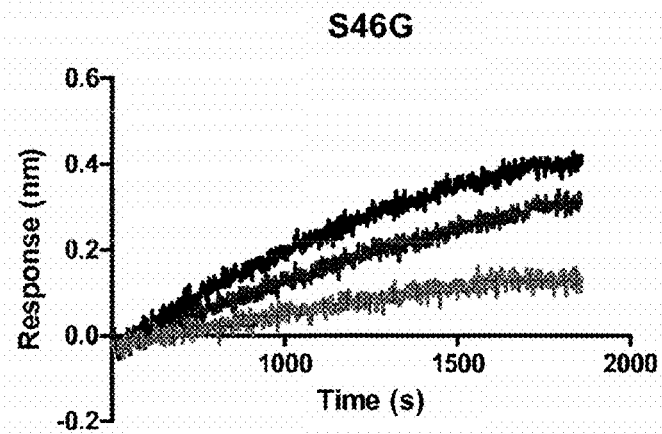
Figure 6D:
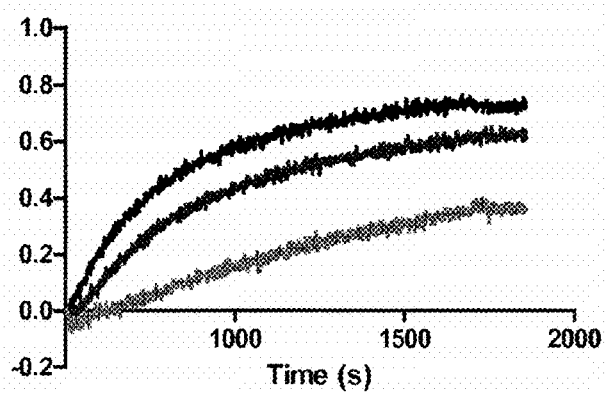
Figure 6E:
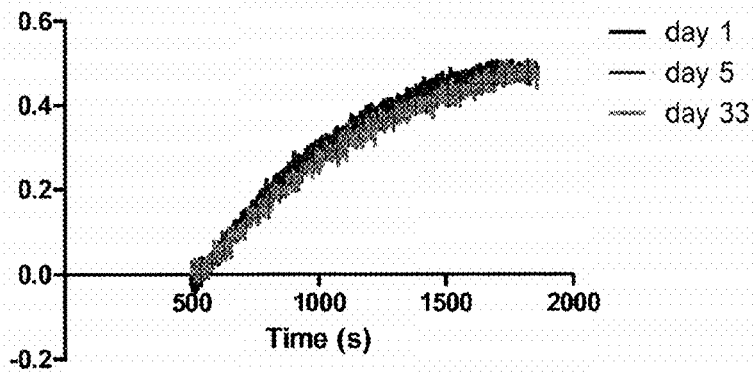
Figure 6F:
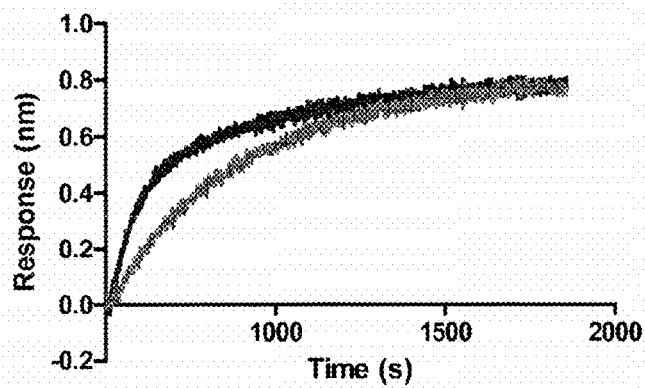
Figure 6G:
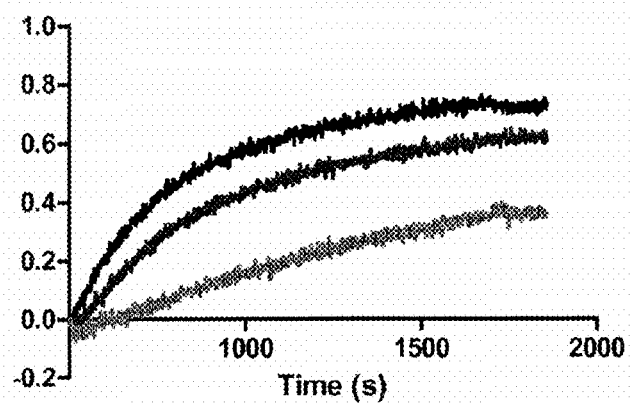
Figure 6H:
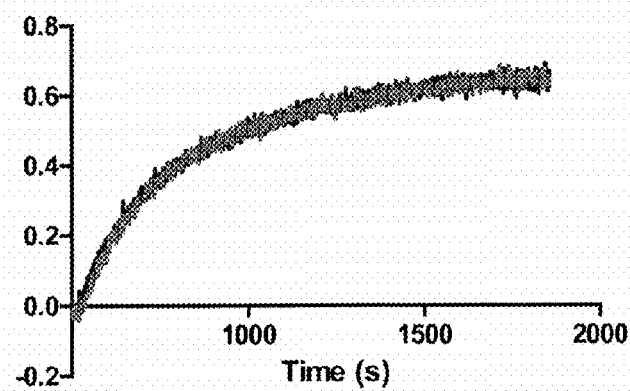
Figure 6I:
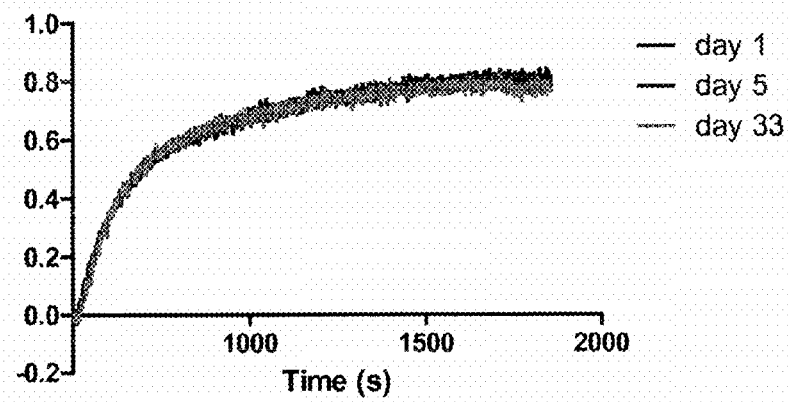

Expression plasmids encoding the recombinant pre-fusion RSV F protein were generated by standard methods widely known within the art, involving site-directed mutagenesis and PCR. The expression platform used was the 293Freestyle cells (Life Technologies, Renfreshire, UK). The cells were transiently transfected using 293Fectin (Life Technologies) according to the manufacturer's instructions and cultured in a shaking incubator for 5 days at 37° C. and 10% $CO_2$. The culture supernatant was harvested and spun for 5 minutes at 300 g to remove cells and cellular debris. The spun supernatant was subsequently sterile filtered using a 0.22 μm vacuum filter and stored at 4° C. until use.

Example 4: Purification of Pre-Fusion RSV F Protein

The recombinant polypeptides were purified by a two-step purification protocol applying a cat-ion exchange column for the initial purification and subsequently a SUPERDEX® 200 column for the polishing step to remove residual contaminants. For the initial ion-exchange step, the culture supernatant was diluted with 2 volumes of 50 mM NaOAc pH 5.0 and passed over a 5 ml HiTrap Capto S column at 5 ml per minute. Subsequently, the column was washed with 10 column volumes (CV) of 20 mM NaOAc, 50 mM NaCl, 0.01% (v/v) TWEEN® 20, pH 5 and eluted 2 CV of 20 mM NaOAc, 1 M NaCl, 0.01% (v/v) TWEEN® 20, pH 5. The eluate was concentrated using a spin concentrator and the protein was further purified using a SUPERDEX® 200 column using 40 mM Tris, 500 mM NaCl, 0.01% (v/v) TWEEN® 20, pH 7.4 as running buffer. In FIG. 1A, the chromatogram from the gel filtration column is shown and the dominant peak contains the pre-fusion RSV F protein. The fractions containing this peak were again pooled and the protein concentration was determined using OD 280 and stored at 4° C. until use. In FIG. 1B, a reduced SDS-PAGE analysis of the final protein preparation is shown and, as can be seen, the purity was >95%. The identity of the band was verified using Western blotting and protein F specific antibodies (not shown).

Example 5: NativePAGE

For initial determination of the multimeric state of the pre-fusion F polypeptides according to the disclosure, culture supernatants from transiently transfected cells were analyzed in a NativePAGE Bis-Tris gel system (Life Technologies). Subsequently, the gels were blotted using the iBlot technology according to the manufacturer's instructions (Life Technologies). An RSV F protein-specific antibody CR9503 (sequences given below in Table 17) was used as primary probe for the detection of pre-fusion RSV F protein and followed by an HRP-conjugated mouse anti-human IgG (Jackson ImmunoResearch, West Grove, Pa.) or an IRDye800CW-conjugated affinity-purified anti-human IgG (rabbit) (Rockland Immunochemicals, Gilbertsville, Pa.). The blots were developed with either standard film (KODAK®) or using the ODYSSEY® CLx infrared imaging system. FIG. 2 shows the NativePAGE analysis of supernatants from monomeric F47– (lane 1), post-fusion and primarily trimeric RSV F protein (lane 2) and purified pre-fusion RSV F protein (lane 3), showing that after purification, only trimeric species are present in the pre-fusion RSV F protein preparation since it migrates similarly to the post-fusion trimer band. This is supported by the elution volume from the gel filtration column as well (FIG. 1A).

Example 6: Quantitative Western Blotting

For quantification of the pre-fusion RSV F protein constructs, quantitative Western blotting was used. Dilutions of culture supernatants were run reduced on 4-12% (w/v) Bis-Tris NuPAGE® gels (Life Technology) and blotted using the IBLOT® technology (Life Technology). The blots were probed with CR9503 (as described above) and developed with either a conjugated mouse anti-human IgG (Jackson ImmunoResearch, West Grove, Pa.) or an IRDye800CW-conjugated affinity-purified anti-human IgG (rabbit) (Rockland Immunochemicals, Gilbertsville, Pa.). The protein quantities were then estimated using a dilution series of purified RSV standard protein and either the ODYSSEY® CLx infrared imaging system or by eye. In FIG. 3, the effects relative to the A2_F24 (SEQ ID NO:19) construct in terms of overall expression levels can be seen. It was shown that single mutations increased the expression level up to five-fold. If double mutants of some of these mutations were generated, synergistic effects could be observed and, in some cases, a further increased expression up to eleven-fold over the A2_F24 was observed.

Example 7: Endpoint Stability Assay

The verification of the pre-fusion conformation of the expressed polypeptides according to the disclosure was done using the BioLayer Interferometry (OCTET®) technology using the pre-fusion-specific antibodies CR9501 or CR9502, or the non-conformation-specific antibody CR9503, which comprises the heavy and light chain variable regions of Motavizumab. The antibodies were biotinylated by standard protocols and immobilized on Streptavidin biosensors (ForteBio, Portsmouth, UK). The procedure was as follows. After equilibration of the sensors in kinetic buffer (FORTEBIO®) for 60 seconds, the Tipss were transferred to PBS with 5 μg/ml of the desired antibody. The loading was carried out for 250 seconds. Subsequently, another equilibration step was included for 200 seconds in kinetic buffer. Lastly, the tipss were transferred to the expression culture supernatant containing the pre-fusion RSV F polypeptides and binding response (nm) after 1200 seconds was recorded. This phase is also referred to as the "association phase." This was done immediately after harvest (day 1) as well as 5 days later (day 5) and the difference in the CR9501 binding was used as a screening tool to identify mutations capable of stabilizing the pre-fusion conformation. A construct was deemed stable if less than 20% loss of binding was observed at day 5 and if more than 20% loss of binding was observed, it was deemed unstable. Stable constructs could then undergo a more stringent stability test if needed. The data analysis was done using the FORTEBIO® Data Analysis 6.4 software (ForteBio).

Example 8: Heat Stability Assay

The stabilizing potential of introduced features into the RSV F polypeptides was estimated by heat stress. For that purpose, culture supernatant from transiently transfected cells or purified protein was heated using a range of temperatures. The samples were subsequently cooled on ice to prevent further heat-induced conformational changes and probed using the CR9501 antibody on the OCTET® technology platform as described in Example 7. The responses obtained at the end of the association phase at the different temperatures were plotted as a function of the temperature and fitted by non-linear regression using the Prism software. This resulted in an estimation of the temperature where the antibody binding level is 50% of the maximum and this value could be used to compare different constructs in terms of pre-fusion heat stability. In FIGS. 4A and 4B, the unmodified ectodomain (SEQ ID NO:13) and the A2_F24 N67I+S215P construct (SEQ ID NO:21) are compared. It can be observed that temperature-induced stress has less effect on the A2_F24 N67I+S215P construct (SEQ ID NO:21) as compared to the unmodified ectodomain. Therefore, it can be concluded that the stabilizing motifs introduced in the polypeptides according to the disclosure, i.e., the trimerization site, the F1-F2-linker and the two-point mutations, lead to a more stable pre-fusion F protein.

Example 9: Association Phase Stability Assay

Figure 7:
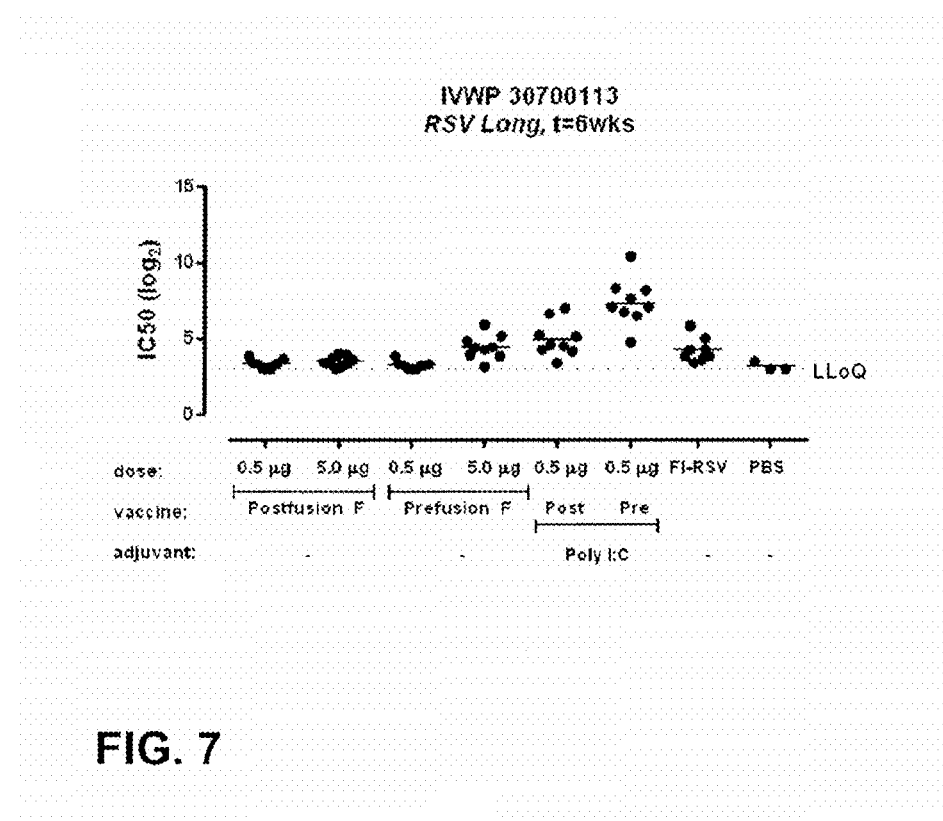
FIG. 7: VNA titers of mice at week 6 after a prime boost at week 0 and 4 with immunogens and doses according to Table 14.

To assess the stability of various point mutations, the OCTET® binding assay, a variation of the previ Example 12: Preclinical Evaluation of Pre-Fusion F Immunogenicity To evaluate the immunogenicity of a stabilized pre-fusion RSV F (A2F24, N67I, S215P) (SEQ ID NO:21), mice were immunized according to Table 14 with 0.5 or 5 μg in a prime—boost regimen at week 0 and week 4. As shown in FIG. 7, mice immunized with pre-fusion F showed higher VNA titers than mice immunized with post-fusion RSV F.

TABLE 14

Immunization scheme

| Group | Preparation | Dose | Adjuvant | N |
|---|---|---|---|---|
| 1 | Post-fusion F | 0.5 μg | — | 9 |
| 2 | Post-fusion F | 5 μg | — | 9 |
| 3 | Pre-fusion F | 0.5 μg | — | 9 |
| 4 | Pre-fusion F | 5 μg | — | 9 |
| 5 | Post-fusion F | 0.5 μg | Poly(I:C) | 9 |
| 6 | Pre-fusion F | 0.5 μg | Poly(I:C) | 9 |
| 8 | FI-RSV | 1/75 | — | 8 |
| 9 | PBS | — | — | 3 |

Figure 8:
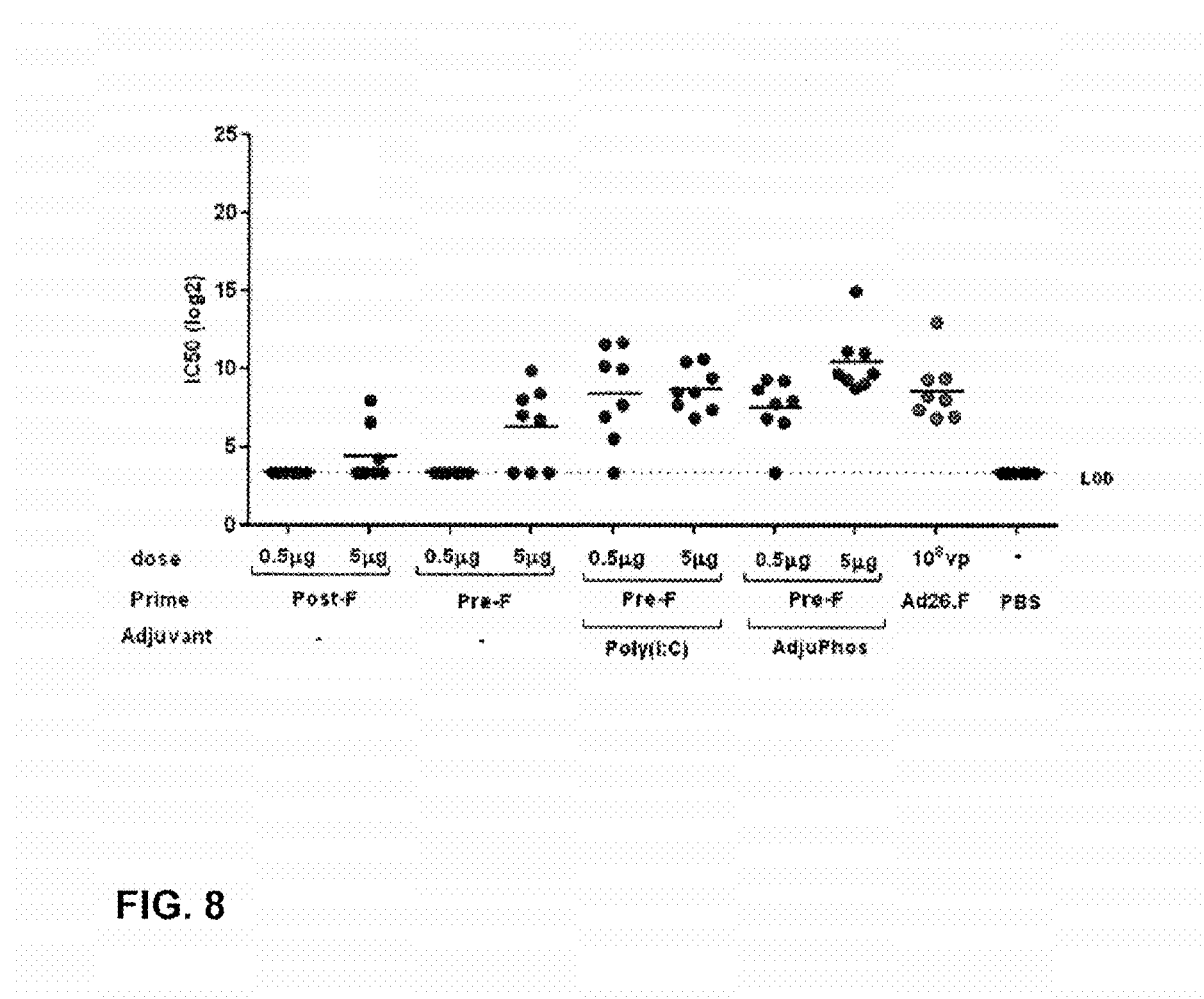
FIG. 8: VNA titers of cotton rats at week 7 after a prime boost at week 0 and 4 with immunogens and doses according to Table 15.

Next, cotton rats were immunized with two different doses of RSV-F in either the post-fusion or the pre-fusion conformation (Table 15). Animals were immunized i.m. at week 0 and week 4. FIG. 8 demonstrates high neutralizing antibody titers at the day of challenge (week 7).

TABLE 15

Groups, immunogen and dose for immunogenicity evaluation and efficacy in cotton rats

| Group | Preparation | Dose | Adjuvant |
|---|---|---|---|
| 1 | Post-fusion F | 0.5 μg | — |
| 2 | Post-fusion F | 5 μg | — |
| 3 | Pre-fusion F | 0.5 μg | — |
| 4 | Pre-fusion F | 5 μg | — |
| 9 | Pre-fusion F | 0.5 μg | Poly IC |
| 10 | Pre-fusion F | 5 μg | Poly IC |
| 11 | Pre-fusion F | 0.5 μg | Adju Phos |
| 12 | Pre-fusion F | 5 μg | Adju Phos |
| 13 | Ad26.RSV.F$_{A2}$ | 10^8 | — |
| 14 | PBS | — | — |

Figure 9:
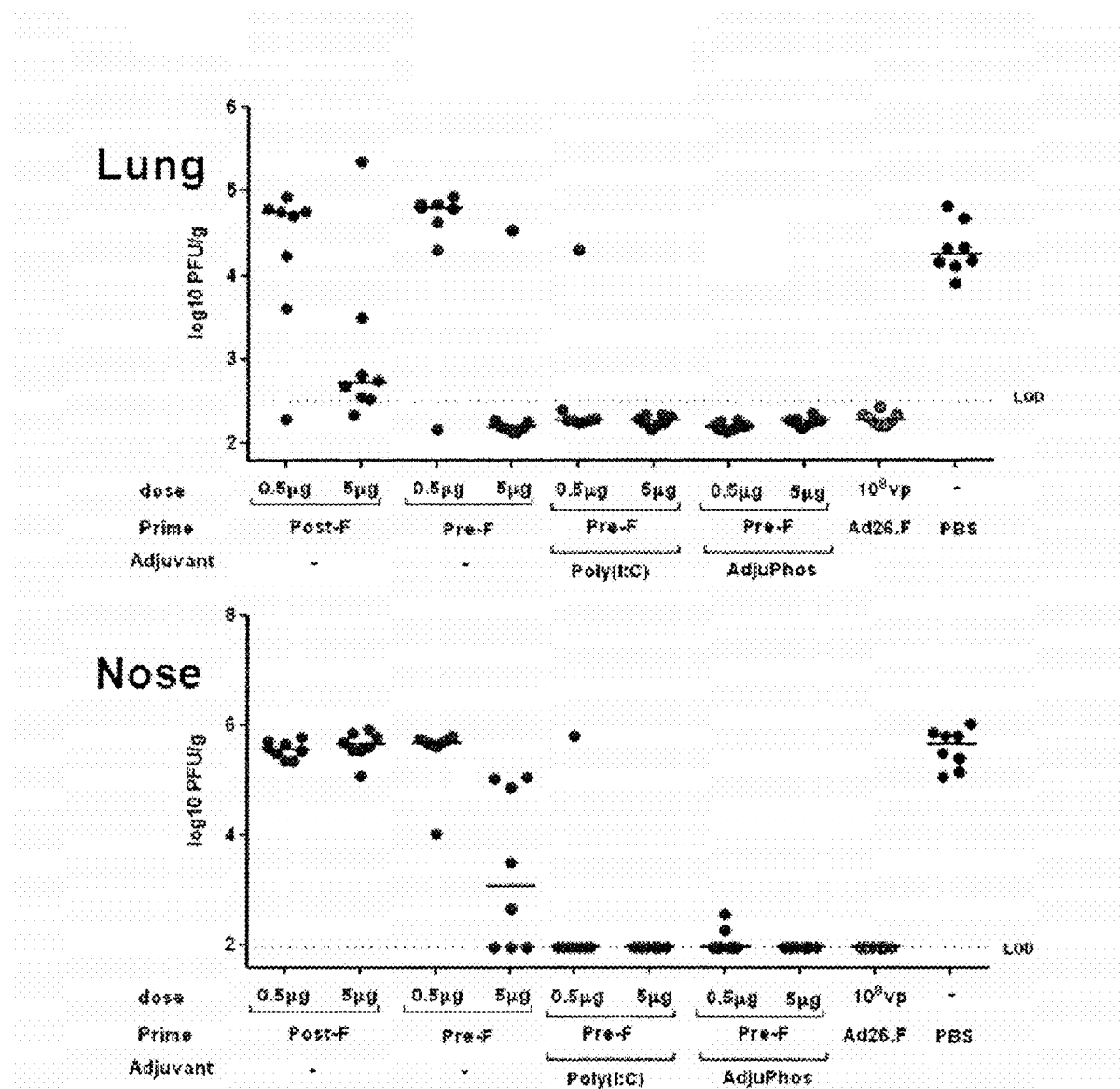
FIG. 9: Lung and nose viral load at 5 days after i.n. RSV challenge.

Five days after challenge, the lung and nose viral load was measured (see FIG. 9).

As shown, the pre-fusion F polypeptides according to the disclosure are able to induce a strong protective immune response that reduced viral load in the lung and even in the nose.

TABLE 16

Standard amino acids, abbreviations and properties

| Amino Acid | 3-Letter | 1-Letter | Side chain polarity | Side chain charge (pH 7.4) |
|---|---|---|---|---|
| alanine | Ala | A | non-polar | Neutral |
| arginine | Arg | R | polar | Positive |
| asparagine | Asn | N | polar | Neutral |
| aspartic acid | Asp | D | polar | Negative |
| cysteine | Cys | C | non-polar | Neutral |
| glutamic acid | Glu | E | polar | Negative |
| glutamine | Gln | Q | polar | Neutral |
| glycine | Gly | G | non-polar | Neutral |
| histidine | His | H | polar | positive (10%) neutral (90%) |
| isoleucine | Ile | I | non-polar | Neutral |
| leucine | Leu | L | non-polar | Neutral |
| lysine | Lys | K | polar | Positive |
| methionine | Met | M | non-polar | Neutral |
| phenylalanine | Phe | F | non-polar | Neutral |
| proline | Pro | P | non-polar | Neutral |
| serine | Ser | S | polar | Neutral |
| threonine | Thr | T | polar | Neutral |
| tryptophan | Trp | W | non-polar | Neutral |
| tyrosine | Tyr | Y | polar | Neutral |
| valine | Val | V | non-polar | Neutral |

TABLE 17

Antibody sequences

| Ab | VH domain | VH CDR1 | VH CDR2 | VH CDR3 |
|---|---|---|---|---|
| CR9501 | Amino acids 1-125 of SEQ ID NO: 53 | GASINSDNYYWT (SEQ ID NO: 54) | HISYTGNTYYTPSLKS (SEQ ID NO: 55) | CGAYVLISNCGWFDS (SEQ ID NO: 56) |
| CR9502 | Amino acids 1-121 of SEQ ID NO: 57 | GFTFSGHTIA (SEQ ID NO: 58) | WVSTNNGNTEYAQKIQG (SEQ ID NO: 59) | EWLVMGGFAFDH (SEQ ID NO: 60) |

| Ab | VL domain | VL CDR1 | VL CDR2 | VL CDR3 |
|---|---|---|---|---|
| CR9501 | Amino acids 1-107 of SEQ ID NO: 61 | QASQDISTYLN (SEQ ID NO: 62) | GASNLET (SEQ ID NO: 63) | QQYQYLPYT (SEQ ID NO: 64) |
| CR9502 | Amino acids 1-110 of SEQ ID NO: 65 | GANNIGSQNVH (SEQ ID NO: 66) | DDDRDRPS (SEQ ID NO: 67) | QVWDSSRDQAVI (SEQ ID NO: 68) |

The amino acid sequence of several of the pre-fusion RSV F constructs is given below. It is noted that the amino acid numbering in the different constructs described herein is based on the wild-type sequence (SEQ ID NO:1), which means that all amino acids from position 1 to and including position 108 of the pre-fusion constructs correspond to the amino acid positions 1-108 of the wild-type sequence, whereas the numbering of the amino acids from position 138 to the end is shifted 22 amino acids, i.e., L138 in the wild-type sequence (SEQ ID NO:1) corresponds to L116 in all the pre-fusion constructs. This is due to the fact that a deletion has been made in the pre-fusion constructs, i.e., the insertion of the GSGSG linker the actual numbering in F1 is not the same between constructs. Thus, the numbering used with respect to the specific mutations according to the disclosure, e.g., S215P, refers to the position of the amino acid in the wild-type sequence.

| Sequences |
| --- |

RSV F protein A2 full length sequence
(SEQ ID NO: 1)
MELLILKANAITTILTAVTFCFASGQNITEEFYQSTCSAVSKGYLSALRTGWYTSVITIELSNI

KKNKCNGTDAKIKLIKQELDKYKNAVTELQLLMQSTPATNNRARRELPRFMNYTLNNAKKTNVT

LSKKRKRRFLGELLGVGSAIASGVAVSKVLHLEGEVNKIKSALLSTNKAVVSLSNGVSVLTSKV

LDLKNYIDKQLLPIVNKQSCSISNIETVIEFQQKNNRLLEITREFSVNAGVTTPVSTYMLTNSE

LLSLINDMPITNDQKKLMSNNVQIVRQQSYSIMSIIKEEVLAYVVQLPLYGVIDTPCWKLHTSP

LCTTNTKEGSNICLTRTDRGWYCDNAGSVSFFPQAETCKVQSNRVECDTMNSLTLPSEVNLCNV

DIENPKYDCKIMTSKTDVSSSVITSLGAIVSCYGKTKCTASNKNRGIIKTESNGCDYVSNKGVD

TVSVGNTLYYVNKQEGKSLYVKGEPIINFYDPLVFPSDEFDASISQVNEKINQSLAFIRKSDEL

LHNVNAVKSTTNIMITTIIIVIIVILLSLIAVGLLLYCKARSTPVTLSKDQLSGINNIAFSN

RSV F protein B1 full length sequence
(SEQ ID NO: 2)
MELLIHRLSAIFLTLAINALYLTSSQNITEEFYQSTCSAVSRGYFSALRTGWYTSVITIELSNI

KETKCNGTDTKVKLIKQELDKYKNAVTELQLLMQNTPAANNRARREAPQYMNYTINTTKNLNVS

ISKKRKRRFLGELLGVGSAIASGIAVSKVLHLEGEVNKIKNALLSTNKAVVSLSNGVSVLTSKV

LDLKNYINNQLLPIVNQQSCRISNIETVIEFQQKNSRLLEINREFSVNAGVTTPLSTYMLTNSE

LLSLINDMPITNDQKKLMSSNVQIVRQQSYSIMSIIKEEVLAYVVQLPIYGVIDTPCWKLHTSP

LCTTNIKEGSNICLTRTDRGWYCDNAGSVSFFPQADICKVQSNRVECDTMNSLTLPSEVSLCNT

DIFNSKYDCKIMTSKTDISSSVITSLGAIVSCYGKTKCTASNKNRGIIKTFSNGCDYVSNKGVD

TVSVGNTLYYVNKLEGKNLYVKGEPIINYYDPLVFPSDEFDASISQVNEKINQSLAFIRRSDEL

LHNVNTGKSTTNIMITTIIIVIIVVLLSLIAIGLLLYCKAKNTPVTLSKDQLSGINNIAFSK

SEQ ID NO: 3
EKKIEAIEKKIEAIEKKIEA

SEQ ID NO: 4
GYIPEAPRDGQAYVRKDGEWVLLSTFL

SEQ ID NO: 5
GSGSG

F8: RSV A2, wt ectodomain
(SEQ ID NO: 13)
MELLILKANAITTILTAVTFCFASGQNITEEFYQSTCSAVSKGYLSALRTGWYTSVITIELSNI

KKNKCNGTDAKIKLIKQELDKYKNAVTELQLLMQSTPATNNRARRELPRFMNYTLNNAKKTNVT

LSKKRKRRELGFLLGVGSAIASGVAVSKVLHLEGEVNKIKSALLSTNKAVVSLSNGVSVLTSKV

LDLKNYIDKQLLPIVNKQSCSISNIETVIEFQQKNNRLLEITREFSVNAGVTTPVSTYMLTNSE

LLSLINDMPITNDQKKLMSNNVQIVRQQSYSIMSIIKEEVLAYVVQLPLYGVIDTPCWKLHTSP

LCTTNTKEGSNICLTRTDRGWYCDNAGSVSFFPQAETCKVQSNRVFCDTMNSLTLPSEVNLCNV

-continued

| Sequences |
|---|
| DIFNPKYDCKIMTSKTDVSSSVITSLGAIVSCYGKTKCTASNKNRGIIKTFSNGCDYVSNKGVD |
| TVSVGNTLYYVNKQEGKSLYVKGEPIINFYDPLVFPSDEFDASISQVNEKINQSLAFIRKSDEL |
| LHHHHHHHH |
| F11: RSV B1, wt ectodomain (SEQ ID NO: 14) |
| MELLIHRLSAIFLTLAINALYLTSSQNITEEFYQSTCSAVSRGYFSALRTGWYTSVITIELSNI |
| KETKCNGTDTKVKLIKQELDKYKNAVTELQLLMQNTPAANNRARREAPQYMNYTINTTKNLNVS |
| ISKKRKRRFLGELLGVGSAIASGIAVSKVLHLEGEVNKIKNALLSTNKAVVSLSNGVSVLTSKV |
| LDLKNYINNQLLPIVNQQSCRISNIETVIEFQQKNSRLLEINREFSVNAGVTTPLSTYMLTNSE |
| LLSLINDMPITNDQKKLMSSNVQIVRQQSYSIMSIIKEEVLAYVVQLPIYGVIDTPCWKLHTSP |
| LCTTNIKEGSNICLTRTDRGWYCDNAGSVSFFPQADTCKVQSNRVFCDTMNSLTLPSEVSLCNT |
| DIENSKYDCKIMTSKTDISSSVITSLGAIVSCYGKTKCTASNKNRGIIKTFSNGCDYVSNKGVD |
| TVSVGNTLYYVNKLEGKNLYVKGEPIINYYDPLVFPSDEFDASISQVNEKINQSLAFIRRSDEL |
| LHHHHHHHH |
| F47: RSV A2, linker stabilized, IZ(S) (SEQ ID NO: 15) |
| MELLILKANAITTILTAVTFCFASGQNITEEFYQSTCSAVSKGYLSALRTGWYTSVITIELSNI |
| KKNKCNGTDAKIKLIKQELDKYKNAVTELQLLMQSTPATNNQARGSGSGRSLGFLLGVGSAIAS |
| GVAVSKVLHLEGEVNKIKSALLSTNKAVVSLSNGVSVLTSKVLDLKNYIDKQLLPIVNKQSCSI |
| SNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |
| ITSLGAIVSCYGKTKCTASNKNRGIIKTFSNGCDYVSNKGVDTVSVGNTLYYVNKQEGKSLYVK |
| GEPIINFYDPLVFPSDEFDASISQVEKKIEAIEKKIEAIEKKIEAGGIEGRHHHHHHHH |
| F47-: RSV A2, linker stabilized, IZ(S) (SEQ ID NO: 16) |
| MELLILKANAITTILTAVTFCFASGQNITEEFYQSTCSAVSKGYLSALRTGWYTSVITIELSNI |
| KKNKCNGTDAKIKLIKQELDKYKNAVTELQLLMQSTPATNNQARGSGSGRSLGFLLGVGSAIAS |
| GVAVSKVLHLEGEVNKIKSALLSTNKAVVSLSNGVSVLTSKVLDLKNYIDKQLLPIVNKQSCSI |
| SNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |
| ITSLGAIVSCYGKTKCTASNKNRGIIKTFSNGCDYVSNKGVDTVSVGNTLYYVNKQEGKSLYVK |
| GEPIINFYDPLVFPSDEFDASISQVEKKIEAIEKKIEAIEKKIEAGG |
| F43: RSV B1, linker stabilized, IZ(S) (SEQ ID NO: 17) |
| MELLIHRLSAIFLTLAINALYLTSSQNITEEFYQSTCSAVSRGYFSALRTGWYTSVITIELSNI |
| KETKCNGTDTKVKLIKQELDKYKNAVTELQLLMQNTPAANNQARGSGSGRSLGFLLGVGSAIAS |
| GIAVSKVLHLEGEVNKIKNALLSTNKAVVSLSNGVSVLTSKVLDLKNYINNQLLPIVNQQSCRI |
| SNIETVIEFQQKNSRLLEINREFSVNAGVTTPLSTYMLTNSELLSLINDMPITNDQKKLMSSNV |
| QIVRQQSYSIMSIIKEEVLAYVVQLPIYGVIDTPCWKLHTSPLCTTNIKEGSNICLTRTDRGWY |

| Sequences |
|---|
| CDNAGSVSFFPQADICKVQSNRVECDTMNSLTLPSEVSLCNTDIENSKYDCKIMTSKTDISSSV |
| ITSLGAIVSCYGKTKCTASNKNRGIIKTFSNGCDYVSNKGVDTVSVGNTLYYVNKLEGKNLYVK |
| GEPIINYYDPLVFPSDEFDASISQVEKKIEAIEKKIEAIEKKIEAGGIEGRHHHHHH |
| F24: RSV B1, linker stabilized, fibritin |
| (SEQ ID NO: 18) |
| MELLIHRLSAIFLTLAINALYLTSSQNITEEFYQSTCSAVSRGYFSALRTGWYTSVITIELSNI |
| KETKCNGTDTKVKLIKQELDKYKNAVTELQLLMQNTPAANNQARGSGSGRSLGFLLGVGSAIAS |
| GIAVSKVLHLEGEVNKIKNALLSTNKAVVSLSNGVSVLTSKVLDLKNYINNQLLPIVNQQSCRI |
| SNIETVIEFQQKNSRLLEINREFSVNAGVTTPLSTYMLTNSELLSLINDMPITNDQKKLMSSNV |
| QIVRQQSYSIMSIIKEEVLAYVVQLPIYGVIDTPCWKLHTSPLCTTNIKEGSNICLTRTDRGWY |
| CDNAGSVSFFPQADTCKVQSNRVFCDTMNSLTLPSEVSLCNTDIFNSKYDCKIMTSKTDISSSV |
| ITSLGAIVSCYGKTKCTASNKNRGIIKTFSNGCDYVSNKGVDTVSVGNTLYYVNKLEGKNLYVK |
| GEPIINYYDPLVFPSDEFDASISQVNEKINQSLAFIRRSDELLSAIGGYIPEAPRDGQAYVRKD |
| GEWVLLSTFLGGIEGRHHHHHH |
| A2_F24: RSV A2, linker stabilized, fibritin |
| (SEQ ID NO: 19) |
| MELLILKANAITTILTAVTFCFASGQNITEEFYQSTCSAVSKGYLSALRTGWYTSVITIELSNI |
| KKNKCNGTDAKIKLIKQELDKYKNAVTELQLLMQSTPATNNQARGSGSGRSLGFLLGVGSAIAS |
| GVAVSKVLHLEGEVNKIKSALLSTNKAVVSLSNGVSVLTSKVLDLKNYIDKQLLPIVNKQSCSI |
| SNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |
| ITSLGAIVSCYGKTKCTASNKNRGIIKTFSNGCDYVSNKGVDTVSVGNTLYYVNKQEGKSLYVK |
| GEPIINFYDPLVFPSDEFDASISQVNEKINQSLAFIRKSDELLSAIGGYIPEAPRDGQAYVRKD |
| GEWVLLSTFLGGIEGR |
| F24-: RSV B1, linker stabilized, fibritin |
| (SEQ ID NO: 20) |
| NELLIHRLSAIFLTLAINALYLTSSQNITEEFYQSTCSAVSRGYFSALRTGWYTSVITIELSNI |
| KETKCNGTDTKVKLIKQELDKYKNAVTELQLLMQNTPAANNQARGSGSGRSLGFLLGVGSAIAS |
| GIAVSKVLHLEGEVNKIKNALLSTNKAVVSLSNGVSVLTSKVLDLKNYINNQLLPIVNQQSCRI |
| SNIETVIEFQQKNSRLLEINREFSVNAGVTTPLSTYMLTNSELLSLINDMPITNDQKKLMSSNV |
| QIVRQQSYSIMSIIKEEVLAYVVQLPIYGVIDTPCWKLHTSPLCTTNIKEGSNICLTRTDRGWY |
| CDNAGSVSFFPQADTCKVQSNRVECDTMNSLTLPSEVSLCNTDIFNSKYDCKIMTSKTDISSSV |
| ITSLGAIVSCYGKTKCTASNKNRGIIKTFSNGCDYVSNKGVDTVSVGNTLYYVNKLEGKNLYVK |
| GEPIINYYDPLVFPSDEFDASISQVNEKINQSLAFIRRSDELLSAIGGYIPEAPRDGQAYVRKD |
| GEWVLLSTFLGGIEGR |
| A2_F24 N67I + S215P: A2, linker stabilized, fibritin |
| (SEQ ID NO: 21) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGFLLGVGSAIAS |
| GVAVSKVLHLEGEVNKIKSALLSTNKAVVSLSNGVSVLTSKVLDLKNYIDKQLLPIVNKQSCSI |
| PNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |

| Sequences |
| --- |

CDNAGSVSFFPQAETCKVQSNRVFCDTMNSLTLPSEVNLCNVDIFNPKYDCKIMTSKTDVSSSV

ITSLGAIVSCYGKTKCTASNKNRGIIKTFSNGCDYVSNKGVDTVSVGNTLYYVNKQEGKSLYVK

GEPIINFYDPLVFPSDEFDASISQVNEKINQSLAFIRKSDELLSAIGGYIPEAPRDGQAYVRKD

GEWVLLSTFLGGIEGR

F24-N67I + S215P: RSV B1, linker stabilized, fibritin
(SEQ ID NO: 22)
MELLIHRLSAIFLTLAINALYLTSSQNITEEFYQSTCSAVSRGYFSALRTGWYTSVITIELSNI

KEIKCNGTDTKVKLIKQELDKYKNAVTELQLLMQNTPAANNQARGSGSGRSLGELLGVGSAIAS

GIAVSKVLHLEGEVNKIKNALLSTNKAVVSLSNGVSVLISKVLDLKNYINNQLLPIVNQQSCRI

PNIETVIEFQQKNSRLLEINREFSVNAGVTTPLSTYMLTNSELLSLINDMPITNDQKKLMSSNV

QIVRQQSYSIMSIIKEEVLAYVVQLPIYGVIDTPCWKLHTSPLCTTNIKEGSNICLTRTDRGWY

CDNAGSVSFFPQADTCKVQSNRVFCDTMNSLTLPSEVSLCNTDIFNSKYDCKIMTSKTDISSSV

ITSLGAIVSCYGKTKCTASNKNRGIIKTFSNGCDYVSNKGVDTVSVGNTLYYVNKLEGKNLYVK

GEPIINYYDPLVFPSDEFDASISQVNEKINQSLAFIRRSDELLSAIGGYIPEAPRDGQAYVRKD

GEWVLLSTFLGGIEGR

A2_F24 N67I + E92D: RSV A2, linker stabilized, fibritin
(SEQ ID NO: 23)
NELLILKANAITTILTAVTFCFASGQNITEEFYQSTCSAVSKGYLSALRTGWYTSVITIELSNI

KKIKCNGTDAKIKLIKQELDKYKNAVTDLQLLMQSTPATNNQARGSGSGRSLGELLGVGSAIAS

GVAVSKVLHLEGEVNKIKSALLSTNKAVVSLSNGVSVLTSKVLDLKNYIDKQLLPIVNKQSCSI

SNIETVIEFQQKNNRLLEITREFSVNAGVTTPVSTYMLTNSELLSLINDMPITNDQKKLMSNNV

QIVRQQSYSIMSIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSKTDVSSSV

ITSLGAIVSCYGKTKCTASNKNRGIIKTFSNGCDYVSNKGVDTVSVGNTLYYVNKQEGKSLYVK

GEPIINFYDPLVFPSDEFDASISQVNEKINQSLAFIRKSDELLSAIGGYIPEAPRDGQAYVRKD

GEWVLLSTFLGGIEGR

F24- N67I + E92D RSV B1, linker stabilized, fibritin
(SEQ ID NO: 24)
MELLIHRLSAIFLTLAINALYLTSSQNITEEFYQSTCSAVSRGYFSALRTGWYTSVITIELSNI

KEIKCNGTDTKVKLIKQELDKYKNAVTDLQLLMQNTPAANNQARGSGSGRSLGFLLGVGSAIAS

GIAVSKVLHLEGEVNKIKNALLSTNKAVVSLSNGVSVLTSKVLDLKNYINNQLLPIVNQQSCRI

SNIETVIEFQQKNSRLLEINREFSVNAGVTTPLSTYMLTNSELLSLINDMPITNDQKKLMSSNV

QIVRQQSYSIMSIIKEEVLAYVVQLPIYGVIDTPCWKLHTSPLCTTNIKEGSNICLTRTDRGWY

CDNAGSVSFFPQADTCKVQSNRVFCDTMNSLTLPSEVSLCNTDIFNSKYDCKIMTSKTDISSSV

ITSLGAIVSCYGKTKCTASNKNRGIIKTFSNGCDYVSNKGVDTVSVGNTLYYVNKLEGKNLYVK

GEPIINYYDPLVFPSDEFDASISQVNEKINQSLAFIRRSDELLSAIGGYIPEAPRDGQAYVRKD

GEWVLLSTFLGGIEGR

A2_F24 N67I + K465Q RSV A2, linker stabilized, fibritin
(SEQ ID NO: 25)
MELLILKANAITTILTAVTFCFASGQNITEEFYQSTCSAVSKGYLSALRTGWYTSVITIELSNI

KKIKCNGTDAKIKLIKQELDKYKNAVTELQLLMQSTPATNNQARGSGSGRSLGELLGVGSAIAS

GVAVSKVLHLEGEVNKIKSALLSTNKAVVSLSNGVSVLTSKVLDLKNYIDKQLLPIVNKQSCSI

-continued

| Sequences |
|---|
| PNIETVIEFQQKNNRLLEITREFSVNAGVITPVSTYMLTNSELLSLINDMPITNDQKKLMSNNV |
| QIVRQQSYSIMSIIKEEVLAYVVQLPLYGVIDIPCWKLHTSPLCTINTKEGSNICLTRTDRGWY |
| CDNAGSVSEEPQAETCKVQSNRVFCDTMNSLTLPSEVNLCNVDIFNPKYDCKIMTSKTDVSSSV |
| ITSLGAIVSCYGKTKCTASNKNRGIIKTESNGCDYVSNKGVDTVSVGNTLYYVNKQEGQSLYVK |
| GEPIINFYDPLVEPSDEEDASISQVNEKINQSLAFIRKSDELLSAIGGYIPEAPRDGQAYVRKD |
| GEWVLLSTFLGGIEGR |

F24- N67I + K465Q RSV B1, linker stabilized, fibritin
(SEQ ID NO: 26)
MELLIHRLSAIFLTLAINALYLTSSQNITEEFYQSTCSAVSRGYFSALRTGWYTSVITIELSNI
KEIKCNGTDTKVKLIKQELDKYKNAVTELQLLMQNTPAANNQARGSGSGRSLGELLGVGSAIAS
GIAVSKVLHLEGEVNKIKNALLSTNKAVVSLSNGVSVLTSKVLDLKNYINNQLLPIVNQQSCRI
PNIETVIEFQQKNSRLLEINREFSVNAGVTTPLSTYMLTNSELLSLINDMPITNDQKKLMSSNV
QIVRQQSYSIMSIIKEEVLAYVVQLPIYGVIDTPCWKLHTSPLCTTNIKEGSNICLTRTDRGWY
CDNAGSVSFFPQADTCKVQSNRVECDTMNSLTLPSEVSLCNTDIENSKYDCKIMTSKTDISSSV
ITSLGAIVSCYGKTKCTASNKNRGIIKTFSNGCDYVSNKGVDTVSVGNTLYYVNKLEGQNLYVK
GEPIINYYDPLVEPSDEFDASISQVNEKINQSLAFIRRSDELLSAIGGYIPEAPRDGQAYVRKD
GEWVLLSTFLGGIEGR A2_F24 N67I + S46G RSV A2, linker stabilized, fibritin
(SEQ ID NO: 27)
MELLILKANAITTILTAVTFCFASGQNITEEFYQSTCSAVSKGYLGALRTGWYTSVITIELSNI
KKIKCNGTDAKIKLIKQELDKYKNAVTDLQLLMQSTPATNNQARGSGSGRSLGELLGVGSAIAS
GVAVSKVLHLEGEVNKIKSALLSTNKAVVSLSNGVSVLTSKVLDLKNYIDKQLLPIVNKQSCSI
SNIETVIEFQQKNNRLLEITREFSVNAGVTTPVSTYMLTNSELLSLINDMPITNDQKKLMSNNV
QIVRQQSYSIMSIIKEEVLAYVVQLPLYGVIDTPCWKLHTSPLCTTNTKEGSNICLTRTDRGWY
CDNAGSVSFFPQAETCKVQSNRVECDTMNSLTLPSEVNLCNVDIENPKYDCKIMTSKTDVSSSV
ITSLGAIVSCYGKTKCTASNKNRGIIKTESNGCDYVSNKGVDTVSVGNTLYYVNKQEGKSLYVK
GEPIINFYDPLVEPSDEFDASISQVNEKINQSLAFIRKSDELLSAIGGYIPEAPRDGQAYVRKD
GEWVLLSTFLGGIEGR F24- N67I + S46G RSV B1, linker stabilized, fibritin
(SEQ ID NO: 28)
MELLIHRLSAIFLTLAINALYLTSSQNITEEFYQSTCSAVSRGYFGALRTGWYTSVITIELSNI
KEIKCNGTDTKVKLIKQELDKYKNAVTDLQLLMQNTPAANNQARGSGSGRSLGFLLGVGSAIAS
GIAVSKVLHLEGEVNKIKNALLSTNKAVVSLSNGVSVLTSKVLDLKNYINNQLLPIVNQQSCRI
SNIETVIEFQQKNSRLLEINREFSVNAGVTTPLSTYMLTNSELLSLINDMPITNDQKKLMSSNV
QIVRQQSYSIMSIIKEEVLAYVVQLPIYGVIDTPCWKLHTSPLCTTNIKEGSNICLTRTDRGWY
CDNAGSVSFFPQADTCKVQSNRVFCDTMNSLTLPSEVSLCNTDIFNSKYDCKIMTSKTDISSSV
ITSLGAIVSCYGKTKCTASNKNRGIIKTFSNGCDYVSNKGVDTVSVGNTLYYVNKLEGKNLYVK
GEPIINYYDPLVFPSDEFDASISQVNEKINQSLAFIRRSDELLSAIGGYIPEAPRDGQAYVRKD
GEWVLLSTFLGGIEGR A2_F24 E92D + S215P: A2, linker stabilized, fibritin
(SEQ ID NO: 29)
MELLILKANAITTILTAVTFCFASGQNITEEFYQSTCSAVSKGYLSALRTGWYTSVITIELSNI
KKNKCNGTDAKIKLIKQELDKYKNAVTDLQLLMQSTPATNNQARGSGSGRSLGFLLGVGSAIAS -continued Sequences

GVAVSKVLHLEGEVNKIKSALLSTNKAVVSLSNGVSVLTSKVLDLKNYIDKQLLPIVNKQSCSI

PNIETVIEFQQKNNRLLEITREFSVNAGVTTPVSTYMLTNSELLSLINDMPITNDQKKLMSNNV

QIVRQQSYSINSIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSKTDVSSSV

ITSLGAIVSCYGKTKCTASNKNRGIIKTFSNGCDYVSNKGVDTVSVGNTLYYVNKQEGKSLYVK

GEPIINFYDPLVFPSDEFDASISQVNEKINQSLAFIRKSDELLSAIGGYIPEAPRDGQAYVRKD

GEWVLLSTFLGGIEGR

F24-E92D + S215P: RSV B1, linker stabilized, fibritin
(SEQ ID NO: 30)
MELLIHRLSAIFLTLAINALYLTSSQNITEEFYQSTCSAVSRGYFSALRTGWYTSVITIELSNI

KETKCNGTDTKVKLIKQELDKYKNAVTDLQLLMQNTPAANNQARGSGSGRSLGFLLGVGSAIAS

GIAVSKVLHLEGEVNKIKNALLSTNKAVVSLSNGVSVLTSKVLDLKNYINNQLLPIVNQQSCRI

PNIETVIEFQQKNSRLLEMIREFSVNAGVTTPLSTYMLINSELLSLINDMPIINDQKKLMSSNV

QIVRQQSYSIMSIIKEEVLAYVVQLPIYGVIDTPCWKLHTSPLCTTNIKEGSNICLTRTDRGWY

CDNAGSVSFFPQADTCKVQSNRVFCDTMNSLTLPSEVSLCNTDIENSKYDCKIMTSKTDISSSV

ITSLGAIVSCYGKTKCTASNKNRGIIKTFSNGCDYVSNKGVDTVSVGNTLYYVNKLEGKNLYVK

GEPIINYYDPLVFPSDEFDASISQVNEKINQSLAFIRRSDELLSAIGGYIPEAPRDGQAYVRKD

GEWVLLSTFLGGIEGR

A2_F24 N67I + S215P + K508E: A2, linker stabilized, fibritin
(SEQ ID NO: 31)
MELLILKANAITTILTAVTFCFASGQNITEEFYQSTCSAVSKGYLSALRTGWYTSVITIELSNI

KKIKCNGTDAKIKLIKQELDKYKNAVTELQLLMQSTPATNNQARGSGSGRSLGELLGVGSAIAS

GVAVSKVLHLEGEVNKIKSALLSTNKAVVSLSNGVSVLTSKVLDLKNYIDKQLLPIVNKQSCSI

PNIETVIEFQQKNNRLLEITREFSVNAGVTTPVSTYMLTNSELLSLINDMPITNDQKKLMSNNV

QIVRQQSYSIMSIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSKTDVSSSV

ITSLGAIVSCYGKTKCTASNKNRGIIKTFSNGCDYVSNKGVDTVSVGNTLYYVNKQEGKSLYVK

GEPIINFYDPLVEPSDEFDASISQVNEKINQSLAFIRE-SDELLSAIGGYIPEAPRDGQAYVRK

DGEWVLLSTFLGGIEGR

A2_F24 N67I + S215P + E487I: A2, linker stabilized, fibritin
(SEQ ID NO: 32)
MELLILKANAITTILTAVTFCFASGQNITEEFYQSTCSAVSKGYLSALRTGWYTSVITIELSNI

KKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSI

PNIETVIEFQQKNNRLLEITREFSVNAGVTTPVSTYMLTNSELLSLINDMPITNDQKKLMSNNV

QIVRQQSYSIMSIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSKTDVSSSV

ITSLGAIVSCYGKTKCTASNKNRGIIKTFSNGCDYVSNKGVDTVSVGNTLYYVNKQEGKSLYVK

-continued

| Sequences |
| --- |
| GEPIINFYDPLVEPSDIFDASISQVNEKINQSLAFIRKSDELLSAIGGYIPEAPRDGQAYVRKD |
| GEWVLLSTFLGGIEGR |
| A2_F24 N67I + S215P + E487Q: A2, linker stabilized, fibritin (SEQ ID NO: 33) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGELLGVGSAIAS |
| GVAVSKVLHLEGEVNKIKSALLSTNKAVVSLSNGVSVLTSKVLDLKNYIDKQLLPIVNKQSCSI |
| PNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |
| ITSLGAIVSCYGKTKCTASNKNRGIIKTFSNGCDYVSNKGVDTVSVGNTLYYVNKQEGKSLYVK |
| GEPIINFYDPLVFPSDQFDASISQVNEKINQSLAFIRKSDELLSAIGGYIPEAPRDGQAYVRKD |
| GEWVLLSTFLGGIEGR |
| A2_F24 N67I + S215P + E487N: A2, linker stabilized, fibritin (SEQ ID NO: 34) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGFLLGVGSAIAS |
| GVAVSKVLHLEGEVNKIKSALLSTNKAVVSLSNGVSVLTSKVLDLKNYIDKQLLPIVNKQSCSI |
| PNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |
| ITSLGAIVSCYGKTKCTASNKNRGIIKTFSNGCDYVSNKGVDTVSVGNTLYYVNKQEGKSLYVK |
| GEPIINFYDPLVFPSDNFDASISQVNEKINQSLAFIRKSDELLSAIGGYIPEAPRDGQAYVRKD |
| GEWVLLSTFLGGIEGR |
| A2_F24 N67I + S215P + D486N: A2, linker stabilized, fibritin (SEQ ID NO: 35) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGELLGVGSAIAS |
| GVAVSKVLHLEGEVNKIKSALLSTNKAVVSLSNGVSVLTSKVLDLKNYIDKQLLPIVNKQSCSI |
| PNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTINTKEGSNICLTRTDRGWY |
| CDNAGSVSFFPQAETCKVQSNRVFCDTMNSLTLPSEVNLCNVDTFNPKYDCKINTSKTDVSSSV |
| ITSLGAIVSCYGKTKCIASNKNRGIIKTFSNGCDYVSNKGVDTVSVGNTLYYVNKQEGKSLYVK |
| GEPIINFYDPLVEPSNEFDASISQVNEKINQSLAFTRKSDELLSAIGGYIPEAPRDGQAYVRKD |
| GEWVLLSTFLGGIEGR |
| A2_F24 N67I + S215P + K465E: A2, linker stabilized, fibritin (SEQ ID NO: 36) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGELLGVGSAIAS |
| GVAVSKVLHLEGEVNKIKSALLSTNKAVVSLSNGVSVLTSKVLDLKNYIDKQLLPIVNKQSCSI |
| PNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |

| Sequences |
| --- |

ITSLGAIVSCYGKTKCTASNKNRGIIKTFSNGCDYVSNKGVDTVSVGNTLYYVNKQEG<u>E</u>SLYVK

GEPIINFYDPLVFPSDEFDASISQVNEKINQSLAFIRKSDELLSAIGGYIPEAPRDGQAYVRKD

GEWVLLSTFLGGIEGR

A2_F24 N67I + S215P + K465Q: A2, linker stabilized, fibritin
(SEQ ID NO: 37)
MELLILKANAITTILTAVTFCFASGQNITEEFYQSTCSAVSKGYLSALRTGWYTSVITIELSNI KK<u>I</u>KCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSI

<u>P</u>NIETVIEFQQKNNRLLEITREFSVNAGVTTPVSTYMLTNSELLSLINDMPITNDQKKLMSNNV

QIVRQQSYSIMSIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSKTDVSSSV

ITSLGAIVSCYGKTKCTASNKNRGIIKTFSNGCDYVSNKGVDTVSVGNTLYYVNKQEG<u>Q</u>SLYVK

GEPIINFYDPLVFPSDEFDASISQVNEKINQSLAFIRKSDELLSAIGGYIPEAPRDGQAYVRKD

GEWVLLSTFLGGIEGR

A2_F24 N67I + S215P + N426S: A2, linker stabilized, fibritin
(SEQ ID NO: 38)
MELLILKANAITTILTAVTFCFASGQNITEEFYQSTCSAVSKGYLSALRTGWYTSVITIELSNI KK<u>I</u>KCNGTDAKIKLIKQELDKYKNAVTELQLLMQSTPATNNQARGSGSGRSLGELLGVGSAIAS

GVAVSKVLHLEGEVNKIKSALLSTNKAVVSLSNGVSVLTSKVLDLKNYIDKQLLPIVNKQSCSI

<u>P</u>NIETVIEFQQKNNRLLEITREFSVNAGVTTPVSTYMLTNSELLSLINDMPITNDQKKLMSNNV

QIVRQQSYSIMSIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSKTDVSSSV

ITSLGAIVSCYGKTKCTAS<u>S</u>KNRGIIKTFSNGCDYVSNKGVDTVSVGNTLYYVNKQEGKSLYVK

GEPIINFYDPLVFPSDEFDASISQVNEKINQSLAFIRKSDELLSAIGGYIPEAPRDGQAYVRKD

GEWVLLSTFLGGIEGR

A2_F24 N67I + S215P + K421N: A2, linker stabilized, fibritin
(SEQ ID NO: 39)
MELLILKANAITTILTAVTFCFASGQNITEEFYQSTCSAVSKGYLSALRTGWYTSVITIELSNI KK<u>I</u>KCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSI

<u>P</u>NIETVIEFQQKNNRLLEITREFSVNAGVTTPVSTYMLTNSELLSLINDMPITNDQKKLMSNNV

QIVRQQSYSIMSIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSKTDVSSSV

ITSLGAIVSCYGKT<u>N</u>CTASNKNRGIIKTFSNGCDYVSNKGVDTVSVGNTLYYVNKQEGKSLYVK

GEPIINFYDPLVFPSDEFDASISQVNEKINQSLAFIRKSDELLSAIGGYIPEAPRDGQAYVRKD

GEWVLLSTFLGGIEGR

A2_F24 N67I + S215P + K209Q: A2, linker stabilized, fibritin
(SEQ ID NO: 40)
MELLILKANAITTILTAVTFCFASGQNITEEFYQSTCSAVSKGYLSALRTGWYTSVITIELSNI -continued

| Sequences |
|---|
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |
| ITSLGAIVSCYGKTKCTASNKNRGIIKTFSNGCDYVSNKGVDTVSVGNTLYYVNKQEGKSLYVK |
| GEPIINFYDPLVFPSDEFDASISQVNEKINQSLAFIRKSDELLSAIGGYIPEAPRDGQAYVRKD |
| GEWVLLSTFLGGIEGR |
| A2_F24 N67I + S215P + K201Q: A2, linker stabilized, fibritin (SEQ ID NO: 41) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGFLLGVGSAIAS |
| GVAVSKVLHLEGEVNKIKSALLSTNKAVVSLSNGVSVLTSKVLDLKNYIDQQLLPIVNKQSCSI |
| PNIETVIEFQQKNNRLLEITREFSVNAGVTTPVSTYMLINSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |
| ITSLGAIVSCYGKTKCTASNKNRGIIKTFSNGCDYVSNKGVDTVSVGNTLYYVNKQEGKSLYVK |
| GEPIINFYDPLVEPSDEFDASISQVNEKINQSLAFIRKSDELLSAIGGYIPEAPRDGQAYVRKD |
| GEWVLLSTFLGGIEGR |
| A2_F24 N67I + S215P + V185N: A2, linker stabilized, fibritin (SEQ ID NO: 42) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGELLGVGSAIAS |
| GVAVSKVLHLEGEVNKIKSALLSTNKAVVSLSNGNSVLTSKVLDLKNYIDKQLLPIVNKQSCSI |
| PNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |
| ITSLGAIVSCYGKTKCTASNKNRGIIKTFSNGCDYVSNKGVDTVSVGNTLYYVNKQEGKSLYVK |
| GEPIINFYDPLVFPSDEFDASISQVNEKINQSLAFIRKSDELLSAIGGYIPEAPRDGQAYVRKD |
| GEWVLLSTFLGGIEGR |
| A2_F24 N67I + S215P + G184N: A2, linker stabilized, fibritin (SEQ ID NO: 43) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGELLGVGSAIAS |
| GVAVSKVLHLEGEVNKIKSALLSTNKAVVSLSNNVSVLTSKVLDLKNYIDKQLLPIVNKQSCSI |
| PNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVECDTMNSLTLPSEVNLCNVDIENPKYDCKIMTSKTDVSSSV |
| ITSLGAIVSCYGKTKCTASNKNRGIIKTESNGCDYVSNKGVDTVSVGNTLYYVNKQEGKSLYVK |
| GEPIINFYDPLVEPSDEFDASISQVNEKINQSLAFIRKSDELLSAIGGYIPEAPRDGQAYVRKD |
| GEWVLLSTFLGGIEGR |
| A2_F24 N67I + S215P + N175P: A2, linker stabilized, fibritin (SEQ ID NO: 44) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGELLGVGSAIAS |
| GVAVSKVLHLEGEVNKIKSALLSTPKAVVSLSNGVSVLTSKVLDLKNYIDKQLLPIVNKQSCSI |

-continued

Sequences

PNIETVIEFQQKNNRLLEITREFSVNAGVTTPVSTYMLINSELLSLINDMPITNDQKKLMSNNV
QIVRQQSYSIMSIIKEEVLAYVVQLPLYGVIDTPCWKLHTSPLCTTNTKEGSNICLTRTDRGWY
CDNAGSVSFFPQAETCKVQSNRVECDTMNSLTLPSEVNLCNVDIFNPKYDCKINTSKTDVSSSV
ITSLGAIVSCYGKTKCTASNKNRGIIKTFSNGCDYVSNKGVDTVSVGNTLYYVNKQEGKSLYVK
GEPIINFYDPLVEPSDEFDASISQVNEKINQSLAFIRKSDELLSAIGGYIPEAPRDGQAYVRKD
GEWVLLSTFLGGIEGR

A2_F24 N67I + S215P + E92D: A2, linker stabilized, fibritin
(SEQ ID NO: 45)
MELLILKANAITTILTAVTFCFASGQNITEEFYQSTCSAVSKGYLSALRTGWYTSVITIELSNI
KKIKCNGTDAKIKLIKQELDKYKNAVTDLQLLMQSTPATNNQARGSGSGRSLGELLGVGSAIAS
GVAVSKVLHLEGEVNKIKSALLSTNKAVVSLSNGVSVLTSKVLDLKNYIDKQLLPIVNKQSCSI
PNIETVIEFQQKNNRLLEITREFSVNAGVTTPVSTYMLTNSELLSLINDMPITNDQKKLMSNNV
QIVRQQSYSIMSIIKEEVLAYVVQLPLYGVIDTPCWKLHTSPLCTTNTKEGSNICLTRTDRGWY
CDNAGSVSFFPQAETCKVQSNRVFCDTMNSLTLPSEVNLCNVDIFNPKYDCKIMTSKTDVSSSV
ITSLGAIVSCYGKTKCTASNKNRGIIKTFSNGCDYVSNKGVDTVSVGNTLYYVNKQEGKSLYVK
GEPIINFYDPLVEPSDEFDASISQVNEKINQSLAFIRKSDELLSAIGGYIPEAPRDGQAYVRKD
GEWVLLSTFLGGIEGR A2_F24 N67I + S215P + K80E: A2, linker stabilized, fibritin
(SEQ ID NO: 46)
MELLILKANAITTILTAVTFCFASGQNITEEFYQSTCSAVSKGYLSALRTGWYTSVITIELSNI
KKIKCNGTDAKIKLIEQELDKYKNAVTELQLLMQSTPATNNQARGSGSGRSLGFLLGVGSAIAS
GVAVSKVLHLEGEVNKIKSALLSTNKAVVSLSNGVSVLTSKVLDLKNYIDKQLLPIVNKQSCSI
PNIETVIEFQQKNNRLLEITREFSVNAGVTTPVSTYMLTNSELLSLINDMPITNDQKKLMSNNV
QIVRQQSYSIMSIIKEEVLAYVVQLPLYGVIDTPCWKLHTSPLCTTNTKEGSNICLTRTDRGWY
CDNAGSVSFFPQAETCKVQSNRVFCDTMNSLTLPSEVNLCNVDIFNPKYDCKIMTSKTDVSSSV
ITSLGAIVSCYGKTKCTASNKNRGIIKTFSNGCDYVSNKGVDTVSVGNTLYYVNKQEGKSLYVK
GEPIINFYDPLVFPSDEFDASISQVNEKINQSLAFIRKSDELLSAIGGYIPEAPRDGQAYVRKD
GEWVLLSTFLGGIEGR A2_F24 N67I + S215P + K77E: A2, linker stabilized, fibritin
(SEQ ID NO: 47)
MELLILKANAITTILTAVTFCFASGQNITEEFYQSTCSAVSKGYLSALRTGWYTSVITIELSNI
KKIKCNGTDAKIELIKQELDKYKNAVTELQLLMQSTPATNNQARGSGSGRSLGFLLGVGSAIAS
GVAVSKVLHLEGEVNKIKSALLSTNKAVVSLSNGVSVLTSKVLDLKNYIDKQLLPIVNKQSCSI
PNIETVIEFQQKNNRLLEITREFSVNAGVTTPVSTYMLTNSELLSLINDMPITNDQKKLMSNNV
QIVRQQSYSIMSIIKEEVLAYVVQLPLYGVIDTPCWKLHTSPLCTTNTKEGSNICLTRTDRGWY
CDNAGSVSFFPQAETCKVQSNRVFCDTMNSLTLPSEVNLCNVDIFNPKYDCKINTSKTDVSSSV
ITSLGAIVSCYGKTKCTASNKNRGIIKTFSNGCDYVSNKGVDTVSVGNTLYYVNKQEGKSLYVK
GEPIINFYDPLVEPSDEFDASISQVNEKINQSLAFIRKSDELLSAIGGYIPEAPRDGQAYVRKD
GEWVLLSTFLGGIEGR

| Sequences |
|---|
| A2_F24 N67I + S215P + S46G: A2, linker stabilized, fibritin<br>(SEQ ID NO: 48)<br>MELLILKANAITTILTAVTFCFASGQNITEEFYQSTCSAVSKGYL<u>G</u>ALRTGWYTSVITIELSNI<br>KK<u>I</u>KCNGTDAKIKLIKQELDKYKNAVTELQLLMQSTPATNNQARGSGSGRSLGFLLGVGSAIAS<br>GVAVSKVLHLEGEVNKIKSALLSTNKAVVSLSNGVSVLTSKVLDLKNYIDKQLLPIVNKQSCSI<br><u>P</u>NIETVIEFQQKNNRLLEITREFSVNAGVTTPVSTYMLTNSELLSLINDMPITNDQKKLMSNNV<br>QIVRQQSYSIMSIIKEEVLAYVVQLPLYGVIDTPCWKLHTSPLCTTNTKEGSNICLTRTDRGWY<br>CDNAGSVSFFPQAETCKVQSNRVFCDTMNSLTLPSEVNLCNVDIFNPKYDCKIMTSKTDVSSSV<br>ITSLGAIVSCYGKTKCTASNKNRGIIKTFSNGCDYVSNKGVDTVSVGNTLYYVNKQEGKSLYVK<br>GEPIINFYDPLVFPSDEFDASISQVNEKINQSLAFIRKSDELLSAIGGYIPEAPRDGQAYVRKD<br>GEWVLLSTFLGGIEGR |
| A2_F24: RSV S46G A2, linker stabilized, fibritin<br>(SEQ ID NO: 49)<br>MELLILKANAITTILTAVTFCFASGQNITEEFYQSTCSAVSKGYL<u>G</u>ALRTGWYTSVITIELSNI<br>KKNKCNGTDAKIKLIKQELDKYKNAVTELQLLMQSTPATNNQARGSGSGRSLGFLLGVGSAIAS<br>GVAVSKVLHLEGEVNKIKSALLSTNKAVVSLSNGVSVLTSKVLDLKNYIDKQLLPIVNKQSCSI<br>SNIETVIEFQQKNNRLLEITREFSVNAGVTTPVSTYMLTNSELLSLINDMPITNDQKKLMSNNV<br>QIVRQQSYSIMSIIKEEVLAYVVQLPLYGVIDTPCWKLHTSPLCTTNTKEGSNICLTRTDRGWY<br>CDNAGSVSFFPQAETCKVQSNRVFCDTMNSLTLPSEVNLCNVDIFNPKYDCKIMTSKTDVSSSV<br>ITSLGAIVSCYGKTKCTASNKNRGIIKTFSNGCDYVSNKGVDTVSVGNTLYYVNKQEGKSLYVK<br>GEPIINFYDPLVEPSDEFDASISQVNEKINQSLAFIRKSDELLSAIGGYIPEAPRDGQAYVRKD<br>GEWVLLSTFLGGIEGR |
| A2_F24: RSV K465Q A2, linker stabilized, fibritin<br>(SEQ ID NO: 50)<br>MELLILKANAITTILTAVTFCFASGQNITEEFYQSTCSAVSKGYLSALRTGWYTSVITIELSNI<br>KKNKCNGTDAKIKLIKQELDKYKNAVTELQLLMQSTPATNNQARGSGSGRSLGFLLGVGSAIAS<br>GVAVSKVLHLEGEVNKIKSALLSTNKAVVSLSNGVSVLTSKVLDLKNYIDKQLLPIVNKQSCSI<br>SNIETVIEFQQKNNRLLEIIREFSVNAGVTTPVSTYMLTNSELLSLIN'MPITNDQKKLMSNNV<br>QIVRQQSYSIMSIIKEEVLAYVVQLPLYGVIDTPCWKLHTSPLCTTNTKEGSNICLTRTDRGWY<br>CDNAGSVSFFPQAETCKVQSNRVECDTMNSLTLPSEVNLCNVDIFNPKYDCKIMTSKTDVSSSV<br>ITSLGAIVSCYGKTKCTASNKNRGIIKTFSNGCDYVSNKGVDTVSVGNTLYYVNKQEG<u>Q</u>SLYVK<br>GEPIINFYDPLVEPSDEFDASISQVNEKINQSLAFIRKSDELLSAIGGYIPEAPRDGQAYVRKD<br>GEWVLLSTFLGGIEGR |
| A2_F24: RSV N67I A2, linker stabilized, fibritin<br>(SEQ ID NO: 51)<br>MELLILKANAITTILTAVTFCFASGQNITEEFYQSTCSAVSKGYLSALRTGWYTSVITIELSNI<br>KK<u>I</u>KCNGTDAKIKLIKQELDKYKNAVTELQLLMQSTPATNNQARGSGSGRSLGFLLGVGSAIAS<br>GVAVSKVLHLEGEVNKIKSALLSTNKAVVSLSNGVSVLTSKVLDLKNYIDKQLLPIVNKQSCSI<br>SNIETVIEFQQKNNRLLEITREFSVNAGVTTPVSTYMLTNSELLSLINDMPITNDQKKLMSNNV<br>QIVRQQSYSIMSIIKEEVLAYVVQLPLYGVIDTPCWKLHTSPLCTTNTKEGSNICLTRTDRGWY<br>CDNAGSVSFFPQAETCKVQSNRVFCDTMNSLTLPSEVNLCNVDIFNPKYDCKIMTSKTDVSSSV |

| Sequences |
| --- |

ITSLGAIVSCYGKTKCTASNKNRGIIKTFSNGCDYVSNKGVDTVSVGNTLYYVNKQEGKSLYVK
GEPIINFYDPLVEPSDEFDASISQVNEKINQSLAFIRKSDELLSAIGGYIPEAPRDGQAYVRKD
GEWVLLSTFLGGIEGR

A2_F24: RSV E92D A2, linker stabilized, fibritin
(SEQ ID NO: 52)
MELLILKANAITTILTAVTFCFASGQNITEEFYQSTCSAVSKGYLSALRTGWYTSVITIELSNI
KKNKCNGTDAKIKLIKQELDKYKNAVTDLQLLMQSTPATNNQARGSGSGRSLGFLLGVGSAIAS
GVAVSKVLHLEGEVNKIKSALLSTNKAVVSLSNGVSVLTSKVLDLKNYIDKQLLPIVNKQSCSI
SNIETVIEFQQKNNRLLEITREFSVNAGVTTPVSTYMLTNSELLSLINDMPITNDQKKLMSNNV
QIVRQQSYSIMSIIKEEVLAYVVQLPLYGVIDTPCWKLHTSPLCTTNTKEGSNICLTRTDRGWY
CDNAGSVSFFPQAETCKVQSNRVFCDTMNSLTLPSEVNLCNVDIFNPKYDCKIMTSKTDVSSSV
ITSLGAIVSCYGKTKCTASNKNRGIIKTFSNGCDYVSNKGVDTVSVGNTLYYVNKQEGKSLYVK
GEPIINFYDPLVFPSDEFDASISQVNEKINQSLAFIRKSDELLSAIGGYIPEAPRDGQAYVRKD
GEWVLLSTFLGGIEGR RSV F protein CL57-v224 full length sequence
(SEQ ID NO: 69)
MELPILKTNAITTILAAVTLCFASSQNITEEFYQSTCSAVSKGYLSALRTGWYTSVITIELSNI
KENKCNGTDAKVKLIKQELDKYKNAVTELQLLMQSTPAANNRARRELPRFMNYTLNNTKNNNVT
LSKKRKRRELGELLGVGSAIASGIAVSKVLHLEGEVNKIKSALLSTNKAVVSLSNGVSVLTSKV
LDLKNYIDKQLLPIVNKQSCSISNIETVIEFQQKNNRLLEITREFSVNAGVTTPVSTYMLTNSE
LLSLINDMPITNDQKKLMSNNVQIVRQQSYSIMSIIKEEVLAYVVQLPLYGVIDTPCWKLHTSP
LCTTNTKEGSNICLTRTDRGWYCDNAGSVSFFPQAETCKVQSNRVFCDTMNSLTLPSEVNLCNI
DIFNPKYDCKIMTSKTDVSSSVITSLGAIVSCYGKTKCTASNKNRGIIKTFSNGCDYVSNKGVD
TVSVGNTLYYVNKQEGKSLYVKGEPIINFYDPLVEPSDEFDASISQVNEKINQSLAFIRKSDEL
LHNVNVGKSTTNIMITTIIIVIIVILLLLIAVGLFLYCKARSTPVTLSKDQLSGINNIAFSN Ectodomain, RSV CL57-v224
(SEQ ID NO: 70)
MELPILKTNAITTILAAVTLCFASSQNITEEFYQSTCSAVSKGYLSALRTGWYTSVITIELSNI
KENKCNGTDAKVKLIKQELDKYKNAVTELQLLMQSTPAANNRARRELPRFMNYTLNNTKNNNVT
LSKKRKRRFLGFLLGVGSAIASGIAVSKVLHLEGEVNKIKSALLSTNKAVVSLSNGVSVLTSKV
LDLKNYIDKQLLPIVNKQSCSISNIETVIEFQQKNNRLLEITREFSVNAGVTTPVSTYMLTNSE
LLSLINDMPITNDQKKLMSNNVQIVRQQSYSIMSIIKEEVLAYVVQLPLYGVIDTPCWKLHTSP
LCTTNTKEGSNICLTRTDRGWYCDNAGSVSFFPQAETCKVQSNRVFCDTMNSLTLPSEVNLCNI
DIFNPKYDCKIMTSKTDVSSSVITSLGAIVSCYGKTKCTASNKNRGIIKTFSNGCDYVSNKGVD
TVSVGNTLYYVNKQEGKSLYVKGEPIINFYDPLVFPSDEFDASISQVNEKINQSLAFIRKSDEL
L PreF, RSV A2, fibritin
(SEQ ID NO: 71)
MELLILKANAITTILTAVTFCFASGQNITEEFYQSTCSAVSKGYLSALRTGWYTSVITIELSNI
KKNKCNGTDAKIKLIKQELDKYKNAVTELQLLMQSTPATNNRARRELPRFMNYTLNNAKKTNVT
LSKKRKRRFLGELLGVGSAIASGVAVSKVLHLEGEVNKIKSALLSTNKAVVSLSNGVSVLTSKV
LDLKNYIDKQLLPIVNKQSCSISNIETVIEFQQKNNRLLEITREFSVNAGVTTPVSTYMLINSE
LLSLINDMPITNDQKKLMSNNVQIVRQQSYSIMSIIKEEVLAYVVQLPLYGVIDTPCWKLHTSP

LCTINTKEGSNICLTRTDRGWYCDNAGSVSFFPQAETCKVQSNRVECDTMNSLTLPSEVNLCNV

DIFNPKYDCKINTSKTDVSSSVITSLGAIVSCYGKTKCIASNKNRGIIKTFSNGCDYVSNKGVD

TVSVGNTLYYVNKQEGKSLYVKGEPIINFYDPLVFPSDEFDASISQVNEKINQSLAFIRKSDEL

LSAIGGYIPEAPRDGQAYVRKDGEWVLLSTFL

PreF N67I S215P, RSV A2, fibritin
(SEQ ID NO: 72)
MELLILKANAITTILTAVTFCFASGQNITEEFYQSTCSAVSKGYLSALRTGWYTSVITIELSNI

KKIKCNGTDAKIKLIKQELDKYKNAVTELQLLMQSTPATNNRARRELPRFMNYTLNNAKKTNVT

LSKKRKRRELGELLGVGSAIASGVAVSKVLHLEGEVNKIKSALLSTNKAVVSLSNGVSVLTSKV

LDLKNYIDKQLLPIVNKQSCSIPNIETVIEFQQKNNRLLEITREFSVNAGVTTPVSTYMLTNSE

LLSLINDMPITNDQKKLMSNNVQIVRQQSYSIMSIIKEEVLAYVVQLPLYGVIDTPCWKLHTSP

LCTTNTKEGSNICLTRTDRGWYCDNAGSVSFFPQAETCKVQSNRVFCDTMNSLTLPSEVNLCNV

DIFNPKYDCKIMTSKTDVSSSVITSLGAIVSCYGKTKCTASNKNRGIIKTFSNGCDYVSNKGVD

TVSVGNTLYYVNKQEGKSLYVKGEPIINFYDPLVEPSDEFDASISQVNEKINQSLAFIRKSDEL

LSAIGGYIPEAPRDGQAYVRKDGEWVLLSTFL

PreF N67I S215P, RSV B1, fibritin
(SEQ ID NO: 73)
MELLIHRLSAIFLTLAINALYLTSSQNITEEFYQSTCSAVSRGYFSALRTGWYTSVITIELSNI

KEIKCNGTDTKVKLIKQELDKYKNAVTELQLLMQNTPAANNRARREAPQYMNYTINTTKNLNVS

ISKKRKRRFLGFLLGVGSAIASGIAVSKVLHLEGEVNKIKNALLSTNKAVVSLSNGVSVLTSKV

LDLKNYINNQLLPIVNQQSCRIPNIETVIEFQQKNSRLLEINREFSVNAGVTTPLSTYMLTNSE

LLSLINDMPITNDQKKLMSSNVQIVRQQSYSIMSIIKEEVLAYVVQLPIYGVIDTPCWKLHTSP

LCTTNIKEGSNICLTRTDRGWYCDNAGSVSFFPQADTCKVQSNRVFCDTMNSLTLPSEVSLCNT

DIENSKYDCKINTSKTDISSSVITSLGAIVSCYGKTKCTASNKNRGIIKTFSNGCDYVSNKGVD

TVSVGNTLYYVNKLEGKNLYVKGEPIINYYDPLVFPSDEFDASISQVNEKINQSLAFIRRSDEL

LSAIGGYIPEAPRDGQAYVRKDGEWVLLSTFL

RSV N67I S215P, RSV CL57-v224, fibritin
(SEQ ID NO: 74)
MELPILKTNAITTILAAVTLCFASSQNITEEFYQSTCSAVSKGYLSALRTGWYTSVITIELSNI

KEIKCNGTDAKVKLIKQELDKYKNAVTELQLLMQSTPAANNRARRELPRFMNYTLNNTKNNNVT

LSKKRKRRELGELLGVGSAIASGIAVSKVLHLEGEVNKIKSALLSTNKAVVSLSNGVSVLTSKV

LDLKNYIDKQLLPIVNKQSCSIPNIETVIEFQQKNNRLLEITREFSVNAGVTTPVSTYMLTNSE

LLSLINDMPITNDQKKLMSNNVQIVRQQSYSIMSIIKEEVLAYVVQLPLYGVIDTPCWKLHTSP

LCTTNTKEGSNICLTRTDRGWYCDNAGSVSFFPQAETCKVQSNRVFCDTMNSLTLPSEVNLCNI

DIFNPKYDCKIMTSKTDVSSSVITSLGAIVSCYGKTKCTASNKNRGIIKTFSNGCDYVSNKGVD

TVSVGNTLYYVNKQEGKSLYVKGEPIINFYDPLVEPSDEFDASISQVNEKINQSLAFIRKSDEL

LSAIGGYIPEAPRDGQAYVRKDGEWVLLSTFL

PreFL N67I S215P, RSV B1, fibritin, Loop
(SEQ ID NO: 22)
MELLIHRLSAIFLTLAINALYLTSSQNITEEFYQSTCSAVSRGYFSALRTGWYTSVITIELSNI

KEIKCNGTDTKVKLIKQELDKYKNAVTELQLLMQNTPAANNQARGSGSGRSLGELLGVGSAIAS

GIAVSKVLHLEGEVNKIKNALLSTNKAVVSLSNGVSVLTSKVLDLKNYINNQLLPIVNQQSCRI

| Sequences |
|---|
| PNIETVIEFQQKNSRLLEINREFSVNAGVTTPLSTYMLTNSELLSLINDMPITNDQKKLMSSNV
QIVRQQSYSIMSIIKEEVLAYVVQLPIYGVIDTPCWKLHTSPLCTTNIKEGSNICLTRTDRGWY
CDNAGSVSFFPQADTCKVQSNRVFCDTMNSLTLPSEVSLCNTDIFNSKYDCKIMTSKTDISSSV
ITSLGAIVSCYGKTKCTASNKNRGIIKTFSNGCDYVSNKGVDTVSVGNTLYYVNKLEGKNLYVK
GEPIINYYDPLVFPSDEFDASISQVNEKINQSLAFIRRSDELLSAIGGYIPEAPRDGQAYVRKD
GEWVLLSTFL PreFL N67I S215P, RSV CL57-v224, fibritin, Loop
(SEQ ID NO: 75)
MELPILKTNAITTILAAVTLCFASSQNITEEFYQSTCSAVSKGYLSALRTGWYTSVITIELSNI
KEIKCNGTDAKVKLIKQELDKYKNAVTELQLLMQSTPAANNQARGSGSGRSLGELLGVGSAIAS
GIAVSKVLHLEGEVNKIKSALLSTNKAVVSLSNGVSVLTSKVLDLKNYIDKQLLPIVNKQSCSI
PNIETVIEFQQKNNRLLEITREFSVNAGVTTPVSTYMLINSELLSLINDMPITNDQKKLMSNNV
QIVRQQSYSIMSIIKEEVLAYVVQLPLYGVIDTPCWKLHTSPLCTTNTKEGSNICLTRTDRGWY
CDNAGSVSFFPQAETCKVQSNRVFCDTMNSLTLPSEVNLCNIDIFNPKYDCKIMTSKTDVSSSV
ITSLGAIVSCYGKTKCTASNKNRGIIKTFSNGCDYVSNKGVDTVSVGNTLYYVNKQEGKSLYVK
GEPIINFYDPLVFPSDEFDASISQVNEKINQSLAFIRKSDELLSAIGGYIPEAPRDGQAYVRKD
GEWVLLSTFL PreF N67I S215P E487Q, RSV A2, fibritin
(SEQ ID NO: 76)
MELLILKANAITTILTAVTFCFASGQNITEEFYQSTCSAVSKGYLSALRTGWYTSVITIELSNI
KKIKCNGTDAKIKLIKQELDKYKNAVTELQLLMQSTPATNNRARRELPRFMNYTLNNAKKTNVT
LSKKRKRRELGELLGVGSAIASGVAVSKVLHLEGEVNKIKSALLSTNKAVVSLSNGVSVLTSKV
LDLKNYIDKQLLPIVNKQSCSIPNIETVIEFQQKNNRLLEITREFSVNAGVTTPVSTYMLTNSE
LLSLINDMPITNDQKKLMSNNVQIVRQQSYSIMSIIKEEVLAYVVQLPLYGVIDTPCWKLHTSP
LCTTNTKEGSNICLTRTDRGWYCDNAGSVSFFPQAETCKVQSNRVFCDTMNSLTLPSEVNLCNV
DIFNPKYDCKIMTSKTDVSSSVITSLGAIVSCYGKTKCTASNKNRGIIKTFSNGCDYVSNKGVD
TVSVGNTLYYVNKQEGKSLYVKGEPIINFYDPLVEPSDQFDASISQVNEKINQSLAFIRKSDEL
LSAIGGYIPEAPRDGQAYVRKDGEWVLLSTFL PreF N67I S215P K201N, RSV A2, fibritin
(SEQ ID NO: 77)
MELLILKANAITTILTAVTFCFASGQNITEEFYQSTCSAVSKGYLSALRTGWYTSVITIELSNI
KKIKCNGTDAKIKLIKQELDKYKNAVTELQLLMQSTPATNNRARRELPRFMNYTLNNAKKTNVT
LSKKRKRRFLGFLLGVGSAIASGVAVSKVLHLEGEVNKIKSALLSTNKAVVSLSNGVSVLTSKV
LDLKNYIDNQLLPIVNKQSCSIPNIETVIEFQQKNNRLLEITREFSVNAGVTTPVSTYMLTNSE
LLSLINDMPITNDQKKLMSNNVQIVRQQSYSIMSIIKEEVLAYVVQLPLYGVIDTPCWKLHTSP
LCTTNTKEGSNICLTRTDRGWYCDNAGSVSFFPQAETCKVQSNRVFCDTMNSLTLPSEVNLCNV
DIFNPKYDCKIMTSKTDVSSSVITSLGAIVSCYGKTKCTASNKNRGIIKTFSNGCDYVSNKGVD
TVSVGNTLYYVNKQEGKSLYVKGEPIINFYDPLVFPSDEFDASISQVNEKINQSLAFIRKSDEL
LSAIGGYIPEAPRDGQAYVRKDGEWVLLSTFL PreF N67I S215P E92D, RSV A2, fibritin
(SEQ ID NO: 78)
MELLILKANAITTILTAVTFCFASGQNITEEFYQSTCSAVSKGYLSALRTGWYTSVITIELSNI
KKIKCNGTDAKIKLIKQELDKYKNAVTDLQLLMQSTPATNNRARRELPRFMNYTLNNAKKTNVT |

| Sequences |
|---|
| LSKKRKRRELGELLGVGSAIASGVAVSKVLHLEGEVNKIKSALLSTNKAVVSLSNGVSVLTSKV
LDLKNYIDKQLLPIVNKQSCSIPNIETVIEFQQKNNRLLEITREFSVNAGVTTPVSTYMLTNSE
LLSLINDMPITNDQKKLMSNNVQIVRQQSYSIMSIIKEEVLAYVVQLPLYGVIDTPCWKLHTSP
LCTTNTKEGSNICLTRTDRGWYCDNAGSVSFFPQAETCKVQSNRVFCDTMNSLTLPSEVNLCNV
DIFNPKYDCKIMTSKTDVSSSVITSLGAIVSCYGKTKCTASNKNRGIIKTFSNGCDYVSNKGVD
TVSVGNTLYYVNKQEGKSLYVKGEPIINFYDPLVFPSDEFDASISQVNEKINQSLAFIRKSDEL
LSAIGGYIPEAPRDGQAYVRKDGEWVLLSTFL PreF N67I S215P D486N, RSV A2, fibritin
(SEQ ID NO: 79)
MELLILKANAITTILTAVTFCFASGQNITEEFYQSTCSAVSKGYLSALRTGWYTSVITIELSNI
KKIKCNGTDAKIKLIKQELDKYKNAVTELQLLMQSTPATNNRARRELPRFMNYTLNNAKKTNVT
LSKKRKRRELGELLGVGSAIASGVAVSKVLHLEGEVNKIKSALLSTNKAVVSLSNGVSVLTSKV
LDLKNYIDKQLLPIVNKQSCSIPNIETVIEFQQKNNRLLEITREFSVNAGVTTPVSTYMLTNSE
LLSLINDMPITNDQKKLMSNNVQIVRQQSYSIMSIIKEEVLAYVVQLPLYGVIDTPCWKLHTSP
LCTTNTKEGSNICLTRTDRGWYCDNAGSVSFFPQAETCKVQSNRVFCDTMNSLTLPSEVNLCNV
DIFNPKYDCKIMTSKTDVSSSVITSLGAIVSCYGKTKCTASNKNRGIIKTFSNGCDYVSNKGVD
TVSVGNTLYYVNKQEGKSLYVKGEPIINFYDPLVEPSNEFDASISQVNEKINQSLAFIRKSDEL
LSAIGGYIPEAPRDGQAYVRKDGEWVLLSTFL Fwt N67I S215P, membrane-bound RSV F, A2,
(SEQ ID NO: 80)
MELLILKANAITTILTAVTFCFASGQNITEEFYQSTCSAVSKGYLSALRTGWYTSVITIELSNI
KKIKCNGTDAKIKLIKQELDKYKNAVTELQLLMQSTPATNNRARRELPRFMNYTLNNAKKINVT
LSKKRKRRFLGELLGVGSAIASGVAVSKVLHLEGEVNKIKSALLSTNKAVVSLSNGVSVLTSKV
LDLKNYIDKQLLPIVNKQSCSIPNIETVIEFQQKNNRLLEITREFSVNAGVTTPVSTYMLTNSE
LLSLINDMPITNDQKKLMSNNVQIVRQQSYSIMSIIKEEVLAYVVQLPLYGVIDTPCWKLHTSP
LCTTNTKEGSNICLTRTDRGWYCDNAGSVSFFPQAETCKVQSNRVFCDTMNSLTLPSEVNLCNV
DIFNPKYDCKIMTSKTDVSSSVITSLGAIVSCYGKTKCTASNKNRGIIKTFSNGCDYVSNKGVD
TVSVGNTLYYVNKQEGKSLYVKGEPIINFYDPLVEPSDEFDASISQVNEKINQSLAFIRKSDEL
LHNVNAVKSTTNIMITTIIIVIIVILLSLIAVGLLLYCKARSTPVTLSKDQLSGINNIAFSN Fs1 N67I S215P, membrane-bound RSV F, A2,
(SEQ ID NO: 81)
MELLILKANAITTILTAVTFCFASGQNITEEFYQSTCSAVSKGYLSALRTGWYTSVITIELSNI
KKIKCNGTDAKIKLIKQELDKYKNAVTELQLLMQSTPATNNQARGSGSGRSLGFLLGVGSAIAS
GVAVSKVLHLEGEVNKIKSALLSTNKAVVSLSNGVSVLTSKVLDLKNYIDKQLLPIVNKQSCSI
PNIETVIEFQQKNNRLLEITREFSVNAGVTTPVSTYMLTNSELLSLINDMPITNDQKKLMSNNV
QIVRQQSYSIMSIIKEEVLAYVVQLPLYGVIDTPCWKLHTSPLCTTNTKEGSNICLTRTDRGWY
CDNAGSVSFFPQAETCKVQSNRVFCDTMNSLTLPSEVNLCNVDIFNPKYDCKIMTSKTDVSSSV
ITSLGAIVSCYGKTKCTASNKNRGIIKTFSNGCDYVSNKGVDTVSVGNTLYYVNKQEGKSLYVK
GEPIINFYDPLVFPSDEFDASISQVNEKINQSLAFIRKSDELLHNVNAVKSTTNIMITTIIIVI
IVILLSLIAVGLLLYCKARSTPVTLSKDQLSGINNIAFSN |

| Sequences |
|---|
| Fwt N67I S215P E92D, membrane-bound RSV F, A2,<br>(SEQ ID NO: 82)<br>MELLILKANAITTILTAVTFCFASGQNITEEFYQSTCSAVSKGYLSALRTGWYTSVITIELSNI<br>KKIKCNGTDAKIKLIKQELDKYKNAVTDLQLLMQSTPATNNRARRELPRFMNYTLNNAKKTNVT<br>LSKKRKRRFLGFLLGVGSAIASGVAVSKVLHLEGEVNKIKSALLSINKAVVSLSNGVSVLTSKV<br>LDLKNYIDKQLLPIVNKQSCSIPNIETVIEFQQKNNRLLEITREFSVNAGVTTPVSTYMLTNSE<br>LLSLINDMPITNDQKKLMSNNVQIVRQQSYSIMSIIKEEVLAYVVQLPLYGVIDTPCWKLHTSP<br>LCTTNTKEGSNICLTRTDRGWYCDNAGSVSFFPQAETCKVQSNRVFCDTMNSLTLPSEVNLCNV<br>DIFNPKYDCKIMTSKTDVSSSVITSLGAIVSCYGKTKCTASNKNRGIIKTFSNGCDYVSNKGVD<br>TVSVGNTLYYVNKQEGKSLYVKGEPIINFYDPLVFPSDEFDASISQVNEKINQSLAFIRKSDEL<br>LHNVNAVKSTTNIMITTIIIVIIVILLSLIAVGLLLYCKARSTPVTLSKDQLSGINNIAFSN |
| Fsl N67I S215P E92D, membrane-bound RSV F, A2,<br>(SEQ ID NO: 83)<br>MELLILKANAITTILTAVTFCFASGQNITEEFYQSTCSAVSKGYLSALRTGWYTSVITIELSNI<br>KKIKCNGTDAKIKLIKQELDKYKNAVTDLQLLMQSTPATNNQARGSGSGRSLGFLLGVGSAIAS<br>GVAVSKVLHLEGEVNKIKSALLSTNKAVVSLSNGVSVLTSKVLDLKNYIDKQLLPIVNKQSCSI<br>PNIETVIEFQQKNNRLLEITREFSVNAGVTTPVSTYMLTNSELLSLINDMPITNDQKKLMSNNV<br>QIVRQQSYSIMSIIKEEVLAYVVQLPLYGVIDTPCWKLHTSPLCTTNTKEGSNICLTRTDRGWY<br>CDNAGSVSFFPQAETCKVQSNRVFCDTMNSLTLPSEVNLCNVDIFNPKYDCKIMTSKTDVSSSV<br>ITSLGAIVSCYGKTKCTASNKNRGIIKTFSNGCDYVSNKGVDTVSVGNTLYYVNKQEGKSLYVK<br>GEPIINFYDPLVFPSDEFDASISQVNEKINQSLAFIRKSDELLHNVNAVKSTTNIMITTIIIVI<br>IVILLSLIAVGLLLYCKARSTPVTLSKDQLSGINNIAFSN |
| Fwt N67I S215P E487Q, membrane-bound RSV F, A2,<br>(SEQ ID NO: 84)<br>MELLILKANAITTILTAVTFCFASGQNITEEFYQSTCSAVSKGYLSALRTGWYTSVITIELSNI<br>KKIKCNGTDAKIKLIKQELDKYKNAVTELQLLMQSTPATNNRARRELPRFMNYTLNNAKKTNVT<br>LSKKRKRRFLGFLLGVGSAIASGVAVSKVLHLEGEVNKIKSALLSTNKAVVSLSNGVSVLTSKV<br>LDLKNYIDKQLLPIVNKQSCSIPNIETVIEFQQKNNRLLEITREFSVNAGVTTPVQTYMLTNSE<br>LLSLINDMPITNDQKKLMSNNVQIVRQQSYSIMSIIKEEVLAYVVQLPLYGVIDTPCWKLHTSP<br>LCTTNTKEGSNICLTRTDRGWYCDNAGSVSFFPQAETCKVQSNRVFCDTMNSLTLPSEVNLCNV<br>DIFNPKYDCKIMTSKTDVSSSVITSLGAIVSCYGKTKCTASNKNRGIIKTFSNGCDYVSNKGVD<br>TVSVGNTLYYVNKQEGKSLYVKGEPIINFYDPLVFPSDQFDASISQVNEKINQSLAFIRKSDEL<br>LHNVNAVKSTTNIMITTIIIVIIVILLSLIAVGLLLYCKARSTPVTLSKDQLSGINNIAFSN |
| Fsl N67I S215P E487Q, membrane-bound RSV F, A2,<br>(SEQ ID NO: 85)<br>MELLILKANAITTILTAVTFCFASGQNITEEFYQSTCSAVSKGYLSALRTGWYTSVITIELSNI<br>KKIKCNGTDAKIKLIKQELDKYKNAVTELQLLMQSTPATNNQARGSGSGRSLGFLLGVGSAIAS<br>GVAVSKVLHLEGEVNKIKSALLSTNKAVVSLSNGVSVLTSKVLDLKNYIDKQLLPIVNKQSCSI<br>PNIETVIEFQQKNNRLLEITREFSVNAGVTTPVSTYMLTNSELLSLINDMPITNDQKKLMSNNV<br>QIVRQQSYSIMSIIKEEVLAYVVQLPLYGVIDTPCWKLHTSPLCTTNTKEGSNICLTRTDRGWY<br>CDNAGSVSFFPQAETCKVQSNRVFCDTMNSLTLPSEVNLCNVDIFNPKYDCKIMTSKTDVSSSV |

| Sequences |
|---|
| ITSLGAIVSCYGKTKCTASNKNRGIIKTFSNGCDYVSNKGVDTVSVGNTLYYVNKEGKSLYVK |
| GEPIINFYDPLVFPSDQFDASISQVNEKINSLAFIRKSDELLHNVNAVKSTTNIMITTIIIVI |
| IVILLSLIAVGLLLYCKARSTPVTLSKDQLSGINNIAFSN |
| Fwt N67I S215P D486N, membrane-bound RSV F, A2, (SEQ ID NO: 86) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNRARRELPRFMNYTLNNAKKTNVT |
| LSKKRKRRFLGFLLGVGSAIASGVAVSKVLHLEGEVNKIKSALLSTNKAVVSLSNGVSVLTSKV |
| LDLKNYIDKQLLPIVNKQSCSIPNIETVIEFQQKNNRLLEITREFSVNAGVTTPVSTYMLTNSE |
| LLSLINDMPITNDQKKLMSNNVQIVRQQSYSIMSIIKEEVLAYVVQLPLYGVIDTPCWKLHTSP |
| LCTTNTKEGSNICLTRTDRGWYCDNAGSVSFFPQAETCKVQSNRVFCDTMNSLTLPSEVNLCNV |
| DIFNPKYDCKIMTSKTDVSSSVITSLGAIVSCYGKTKCTASNKNRGIIKTFSNGCDYVSNKGVD |
| TVSVGNTLYYVNKEGKSLYVKGEPIINFYDPLVEPSNEFDASISQVNEKINSLAFIRKSDEL |
| LHNVNAVKSTTNIMITTIIIVIIVILLSLIAVGLLLYCKARSTPVTLSKDQLSGINNIAFSN |
| Fsl N67I S215P D486N, membrane-bound RSV F, A2, (SEQ ID NO: 87) |
| MELLILKANAITTILTAVTFCFASGQNITEEFYQSTCSAVSKGYLSALRTGWYTSVITIELSNI |
| KKIKCNGTDAKIKLIKQELDKYKNAVTELQLLMQSTPATNNQARGSGSGRSLGFLLGVGSAIAS |
| GVAVSKVLHLEGEVNKIKSALLSTNKAvvSLSNGVSVLTSKVLDLKNYIDKQLLPIVNKQSCSI |
| PNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |
| CDNAGSVSFFPQAETCKVQSNRVFCDTMNSLTLPSEVNLCNVDIFNPKYDCKIMTSKTDVSSSV |
| ITSLGAIVSCYGKTKCTASNKNRGIIKTFSNGCDYVSNKGVDTVSVGNTLYYVNKEGKSLYVK |
| GEPIINFYDPLVFPSNEFDASISQVNEKINSLAFIRKSDELLHNVNAVKSTTNIMITTIIIVI |
| IVILLSLIAVGLLLYCKARSTPVTLSKDQLSGINNIAFSN |
| Fwt N67I S215P S46G, membrane-bound RSV F, A2, (SEQ ID NO: 88) |
| MELLILKANAITTILTAVTFCFASGQNITEEFYQSTCSAVSKGYLGALRTGWYTSVITIELSNI |
| KKIKCNGTDAKIKLIKQELDKYKNAVTELQLLMQSTPATNNRARRELPRFMNYTLNNAKKTNVT |
| LSKKRKRRFLGELLGVGSAIASGVAVSKVLHLEGEVNKIKSALLSTNKAVVSLSNGVSVLTSKV |
| LDLKNYIDKQLLPIVNKQSCSIPNIETVIEFQQKNNRLLEITREFSVNAGVTTPVSTYMLTNSE |
| LLSLINDMPITNDQKKLMSNNVQIVRQQSYSIMSIIKEEVLAYVVQLPLYGVIDTPCWKLHTSP |
| LCTTNTKEGSNICLTRTDRGWYCDNAGSVSFFPQAETCKVQSNRVFCDTMNSLTLPSEVNLCNV |
| DIFNPKYDCKIMTSKTDVSSSVITSLGAIVSCYGKTKCTASNKNRGIIKTFSNGCDYVSNKGVD |
| TVSVGNTLYYVNKEGKSLYVKGEPIINFYDPLVFPSDEFDASISQVNEKINSLAFIRKSDEL |
| LHNVNAVKSTTNIMITTIIIVIIVILLSLIAVGLLLYCKARSTPVTLSKDQLSGINNIAFSN |
| Fsl N67I S215P S46G, membrane-bound RSV F, A2, (SEQ ID NO: 89) |
| MELLILKANAITTILTAVTFCFASGQNITEEFYQSTCSAVSKGYLGALRTGWYTSVITIELSNI |
| KKIKCNGTDAKIKLIKQELDKYKNAVTELQLLMQSTPATNNQARGSGSGRSLGFLLGVGSAIAS |
| GVAVSKVLHLEGEVNKIKSALLSTNKAVVSLSNGVSVLTSKVLDLKNYIDKQLLPIVNKQSCSI |
| PNIETVIEFQQKNNRLLEITREFSVNAGVTTPVSTYMLTNSELLSLINDMPITNDQKKLMSNNV |
| QIVRQQSYSIMSIIKEEVLAYVVQLPLYGVIDTPCWKLHTSPLCTTNTKEGSNICLTRTDRGWY |

| Sequences |
|---|
| CDNAGSVSFFPQAETCKVQSNRVFCDTMNSLTLPSEVNLCNVDIFNPKYDCKIMTSKTDVSSSV<br>ITSLGAIVSCYGKTKCTASNKNRGIIKTFSNGCDYVSNKGVDTVSVGNTLYYVNKQEGKSLYVK<br>GEPIINFYDPLVEPSDEFDASISQVNEKINQSLAFIRKSDELLHNVNAVKSTTNIMITTIIIVI<br>IVILLSLIAVGLLLYCKARSTPVTLSKDQLSGINNIAFSN<br><br>CR9501 heavy chain (SEQ ID NO: 53):<br>QVQLVQSGPGLVKPSQTLALTCNVSGASINSDNYYWTWIRQRPGGGLEWIGHISYTGNTYYTPS<br>LKSRLSMSLETSQSQFSLRLTSVTAADSAVYFCAACGAYVLISNCGWFDSWGQGTQVTVSSAST<br>KGPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKKVEPKSC<br><br>CR9501 light chain (SEQ ID NO: 61):<br>EIVMTQSPSSLSASIGDRVTITCQASQDISTYLNWYQQKPGQAPRLLIYGASNLETGVPSRFTG<br>SGYGTDFSVTISSLQPEDIATYYCQQYQYLPYTFAPGTKVEIKRTVAAPSVFIFPPSDEQLKSG<br>TASVVCLLNNFYPREAKVQWKVDNALQSGNSQESVTEQDSKDSTYSLSSTLTLSKADYEKHKVY<br>ACEVTHQGLSSPVTKSFNRGEC<br><br>CR9502 heavy chain (SEQ ID NO: 57):<br>EVQLLQSGAELKKPGASVKISCKTSGFTFSGHTIAWVRQAPGQGLEWMGWVSTNNGNTEYAQKI<br>QGRVTMTMDTSTSTVYMELRSLTSDDTAVYFCAREWLVMGGFAFDHWGQGTLLTVSSASTKGPS<br>VFPLAPSSKSTSGGTAALGCLVKDYFPEPVTVSWNSGALTSGVHTFPAVLQSSGLYSLSSVVTV<br>PSSSLGTQTYICNVNHKPSNTKVDKRVEPKSC<br><br>CR9502 light chain (SEQ ID NO: 65):<br>QSVLTQASSVSVAPGQTARITCGANNIGSQNVHWYQQKPGQAPVLVVYDDRDRPSGIPDRFSGS<br>NSGNTATLTISRVEAGDEADYYCQVWDSSRDQAVIFGGGTKLTVLGQPKAAPSVTLFPPSSEEL<br>QANKATLVCLISDPIPGAVTVAWKADSSPVKAGvETTTPSKQSNNKYAASSYLSLTPEQWKSHR<br>SYSCQVTHEGSTVEKTIAPTECS |

The invention claimed is:

1. A recombinant pre-fusion respiratory syncytial virus (RSV) Fusion (F) mutant polypeptide, comprising a mutation of the amino acid residue N/T at position 67 into I and/or a mutation of the amino acid residue S at position 215 into P, wherein the amino acid positions are given in reference to the sequence of RSV F protein from the A2 strain (SEQ ID NO: 1).

2. The pre-fusion RSV F mutant polypeptide according to claim 1, wherein the mutant polypeptide comprises an F1 domain and an F2 domain, and a linking sequence comprising from 1 to 10 amino acid residues, linking said F1 domain to said F2 domain.

3. The pre-fusion RSV F mutant polypeptide of claim 1, comprising a truncated F1 domain and an F2 domain, and a linking sequence comprising 1 to 10 amino acid residues, linking said F1 domain to said F2 domain.

4. The pre-fusion RSV F mutant polypeptide according to claim 3, wherein the mutant polypeptide comprises a heterologous trimerization domain linked to said truncated F1 domain.

5. The pre-fusion RSV F mutant polypeptide of claim 1, wherein the mutant polypeptide comprises at least one further mutation, wherein said mutation is selected from the group consisting of:
(a) a mutation of the amino acid residue on position 46;
(b) a mutation of the amino acid residue on position 77;
(c) a mutation of the amino acid residue on position 80;
(d) a mutation of the amino acid residue on position 92;
(e) a mutation of the amino acid residue on position 175;
(f) a mutation of the amino acid residue on position 184;
(g) a mutation of the amino acid residue on position 185;
(h) a mutation of the amino acid residue on position 201;
(i) a mutation of the amino acid residue on position 209;
(j) a mutation of the amino acid residue on position 421;
(k) a mutation of the amino acid residue on position 426;
(l) a mutation of the amino acid residue on position 465;
(m) a mutation of the amino acid residue on position 486;
(n) a mutation of the amino acid residue on position 487; and
(o) a mutation of the amino acid residue on position 508.

6. The pre-fusion RSV F mutant polypeptide according to claim 5, wherein the at least one further mutation is selected from the group consisting of:
(a) a mutation of the amino acid residue S on position 46 into G;
(b) a mutation of the amino acid residue K on position 77 into E;
(c) a mutation of the amino acid residue K on position 80 into E;
(d) a mutation of the amino acid residue E on position 92 into D;
(e) a mutation of the amino acid residue N on position 175 into P;
(f) a mutation of the amino acid residue G on position 184 into N;
(g) a mutation of the amino acid residue V on position 185 into N;
(h) a mutation of the amino acid residue K on position 201 into Q;
(i) a mutation of the amino acid residue K on position 209 into Q;
(j) a mutation of the amino acid residue K on position 421 into N;
(k) a mutation of the amino acid residue N on position 426 into S;
(l) a mutation of the amino acid residue K on position 465 into E or Q;
(m) a mutation of the amino acid residue D on position 486 into N;
(n) a mutation of the amino acid residue E on position 487 into Q, N or I; and
(o) a mutation of the amino acid residue K on position 508 into E.

7. The pre-fusion RSV F mutant polypeptide according to claim 1, wherein the mutant polypeptide comprises at least two mutations.

8. The pre-fusion RSV F mutant polypeptide of claim 1, wherein the heterologous trimerization domain comprises SEQ ID NO:3.

9. The pre-fusion RSV F mutant polypeptide according to claim 8, wherein the trimerization domain is linked to amino acid residue 495 of the RSV F protein.

10. The pre-fusion RSV F mutant polypeptide of claim 1, wherein the heterologous trimerization domain comprises SEQ ID NO:4.

11. The pre-fusion RSV F mutant polypeptide according to claim 10, wherein the trimerization domain is linked to amino acid residue 513 of the RSV F protein.

12. The pre-fusion RSV F mutant polypeptide of claim 1, wherein the linker between the F1 and the F2 domain comprises 5 amino acid residues.

13. The pre-fusion RSV F mutant polypeptide of claim 12, wherein the linker comprises SEQ ID NO:5.

14. The pre-fusion RSV F mutant polypeptide of claim 1, wherein the F1 domain and/or the F2 domain are from an RSV A strain.

15. The pre-fusion RSV F mutant polypeptide of claim 1, wherein the F1 domain and/or the F2 domain are from an RSV B strain.

16. The pre-fusion RSV F mutant polypeptide of claim 1, wherein the mutant polypeptide comprises a peptide selected from the group consisting of SEQ ID NO: 21-SEQ ID NO: 52 and SEQ ID NOs:71-89.

17. The pre-fusion RSV F mutant polypeptide of claim 1, wherein the mutant polypeptide does not comprise a HIS-Tag.

18. A nucleic acid molecule encoding the pre-fusion RSV F mutant polypeptide of claim 1.

19. The nucleic acid molecule of claim 18, wherein the nucleic acid molecule is codon-optimized for expression in mammalian cells.

20. A vector comprising the nucleic acid molecule of claim 18.

21. A composition comprising:
the pre-fusion RSV F mutant polypeptide of claim 1, and
a pharmaceutically acceptable carrier or excipient.

22. A method of inducing an immune response against RSV F protein in a subject, the method comprising:
administering to the subject the pre-fusion RSV F mutant polypeptide of claim 1 in an amount to induce an immune response against RSV F protein in the subject.

23. A vaccine comprising:
the pre-fusion RSV F mutant polypeptide of claim 1.

24. A method of prophylaxing and/or treating RSV infection in a subject, the method comprising:
administering to the subject the pre-fusion RSV F mutant polypeptide of claim 1, to prophylax against and/or treat the subject for RSV infection.

25. A vector comprising the nucleic acid molecule of claim 19.

26. The pre-fusion RSV F mutant polypeptide according to claim 1, comprising the mutation of the amino acid residue N/T at position 67 into I and the mutation of the amino acid residue S at position 215 into P.

27. The pre-fusion RSV F mutant polypeptide according to claim 26, further comprising a mutation of the amino acid residue K at position 66 into E, a mutation of the amino acid residue I at position 76 into V, and a mutation of the amino acid residue D at position 486 into N.

28. A nucleic acid molecule encoding the pre-fusion RSV F mutant polypeptide of claim 26.

29. A nucleic acid molecule encoding the pre-fusion RSV F mutant polypeptide of claim 27.

30. A vector comprising the nucleic acid molecule of claim 28.

31. A vector comprising the nucleic acid molecule of claim 29.

32. A vaccine comprising the pre-fusion RSV F mutant polypeptide of claim 27 and/or a vector comprising a nucleic acid molecule encoding the same.

33. A method of prophylaxing and/or treating RSV infection in a subject, the method comprising:
administering to the subject the pre-fusion RSV F mutant polypeptide of claim 27 and/or a vector comprising a nucleic acid molecule encoding the same, to prophylax against and/or treat the subject for RSV infection.

34. The pre-fusion RSV F mutant polypeptide according to claim 26, further comprising a mutation of the amino acid residue S at position 46 into G, a mutation of the amino acid residue K at position 66 into E, and a mutation of the amino acid residue I at position 76 into V.

35. A nucleic acid molecule encoding the pre-fusion RSV F mutant polypeptide of claim 34.

36. A vector comprising the nucleic acid molecule of claim 35.

37. A vaccine comprising the pre-fusion RSV F mutant polypeptide of claim 34 and/or a vector comprising a nucleic acid molecule encoding the same.

38. A method of prophylaxing and/or treating RSV infection in a subject, the method comprising:
administering to the subject the pre-fusion RSV F mutant polypeptide of claim 34 and/or a vector comprising a nucleic acid molecule encoding the same, to prophylax against and/or treat the subject for RSV infection.

* * * * *

SEQUENCE LISTING

```
<160> NUMBER OF SEQ ID NOS: 97

<210> SEQ ID NO 1
<211> LENGTH: 574
<212> TYPE: PRT
<213> ORGANISM: Artificial Sequence
<220> FEATURE:
<223> OTHER INFORMATION: RSV F protein A2 full length sequence

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80
```

-continued

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu

```
                    500                 505                 510
Leu His Asn Val Asn Ala Val Lys Ser Thr Thr Asn Ile Met Ile Thr
                515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 2
<211> LENGTH: 574
<212> TYPE: PRT
<213> ORGANISM: Artificial Sequence
<220> FEATURE:
<223> OTHER INFORMATION: RSV F protein B1 full length sequence

<400> SEQUENCE: 2

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
```

-continued

```
                290                 295                 300
Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

<210> SEQ ID NO 3
<211> LENGTH: 20
<212> TYPE: PRT
<213> ORGANISM: Artificial Sequence
<220> FEATURE:
<223> OTHER INFORMATION: Trimerization domain

<400> SEQUENCE: 3

```
Glu Lys Lys Ile Glu Ala Ile Glu Lys Lys Ile Glu Ala Ile Glu Lys
1               5                   10                  15

Lys Ile Glu Ala
            20
```

<210> SEQ ID NO 4
<211> LENGTH: 27
<212> TYPE: PRT
<213> ORGANISM: Artificial Sequence
<220> FEATURE:
<223> OTHER INFORMATION: Trimerization domain

<400> SEQUENCE: 4

```
Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

Gly Ser Gly Ser Gly
1               5

<210> SEQ ID NO 6
<211> LENGTH: 40
<212> TYPE: PRT
<213> ORGANISM: Artificial Sequence
<220> FEATURE:
<223> OTHER INFORMATION: Trimerization domain

<400> SEQUENCE: 6

Ser Ser Leu Gln Gly Asp Val Gln Ala Leu Gln Glu Ala Gly Tyr Ile
1               5                   10                  15

Pro Glu Ala Pro Arg Asp Gly Gln Ala Tyr Val Arg Lys Asp Gly Glu
            20                  25                  30

Trp Val Leu Leu Ser Thr Phe Leu
        35                  40

<210> SEQ ID NO 7
<211> LENGTH: 7
<212> TYPE: PRT
<213> ORGANISM: Artificial Sequence
<220> FEATURE:
<223> OTHER INFORMATION: Isoleucine Zipper domain

<400> SEQUENCE: 7

Ile Glu Ala Ile Glu Lys Lys
1               5

<210> SEQ ID NO 8
<211> LENGTH: 31
<212> TYPE: PRT
<213> ORGANISM: Artificial Sequence
<220> FEATURE:
<223> OTHER INFORMATION: Isoleucine Zipper (L)

<400> SEQUENCE: 8

Ile Glu Lys Lys Ile Glu Ala Ile Glu Lys Lys Ile Glu Ala Ile Glu
1               5                   10                  15

Lys Lys Ile Glu Ala Ile Glu Ala Ile Glu Lys Lys Ile Glu Ala
            20                  25                  30

<210> SEQ ID NO 9
<211> LENGTH: 28
<212> TYPE: PRT
<213> ORGANISM: Artificial Sequence
<220> FEATURE:
<223> OTHER INFORMATION: GCN4II

<400> SEQUENCE: 9

Glu Asp Lys Ile Glu Glu Ile Leu Ser Lys Ile Tyr His Ile Glu Asn
1               5                   10                  15
```

-continued

Glu Ile Ala Arg Ile Lys Lys Leu Ile Gly Glu Ala
              20                  25

<210> SEQ ID NO 10
<211> LENGTH: 28
<212> TYPE: PRT
<213> ORGANISM: Artificial Sequence
<220> FEATURE:
<223> OTHER INFORMATION: Optimized GCN4II

<400> SEQUENCE: 10

Glu Asp Lys Val Glu Glu Leu Leu Ser Lys Ile Tyr His Ile Glu Asn
1               5                   10                  15

Arg Ile Ala Arg Ile Glu Lys Leu Val Gly Glu Ala
              20                  25

<210> SEQ ID NO 11
<211> LENGTH: 43
<212> TYPE: PRT
<213> ORGANISM: Artificial Sequence
<220> FEATURE:
<223> OTHER INFORMATION: Matrilin -1 (long version)

<400> SEQUENCE: 11

Glu Glu Asp Pro Cys Glu Cys Lys Ser Ile Val Lys Phe Gln Thr Lys
1               5                   10                  15

Val Glu Glu Leu Ile Asn Thr Leu Gln Gln Lys Leu Glu Ala Val Ala
              20                  25                  30

Lys Arg Ile Glu Ala Leu Glu Asn Lys Ile Ile
          35                  40

<210> SEQ ID NO 12
<211> LENGTH: 26
<212> TYPE: PRT
<213> ORGANISM: Artificial Sequence
<220> FEATURE:
<223> OTHER INFORMATION: Matrillin- 1 (short version)

<400> SEQUENCE: 12

Glu Glu Leu Ile Asn Thr Leu Gln Gln Lys Leu Glu Ala Val Ala Lys
1               5                   10                  15

Arg Ile Glu Ala Leu Glu Asn Lys Ile Ile
          20                  25

<210> SEQ ID NO 13
<211> LENGTH: 521
<212> TYPE: PRT
<213> ORGANISM: Artificial Sequence
<220> FEATURE:
<223> OTHER INFORMATION: F8: RSV A2, wt ectodomain

<400> SEQUENCE: 13

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
              20                  25                  30

Tyr Gln Ser Thr Cys Ser Ala Val Ser Lys Gly Tyr Leu Ser Ala Leu
          35                  40                  45

Arg Thr Gly Trp Tyr Thr Ser Val Ile Thr Ile Glu Leu Ser Asn Ile
      50                  55                  60

Lys Lys Asn Lys Cys Asn Gly Thr Asp Ala Lys Ile Lys Leu Ile Lys
65                  70                  75                  80

-continued

```
Gln Glu Leu Asp Lys Tyr Lys Asn Ala Val Thr Leu Gln Leu Leu
             85                  90                  95

Met Gln Ser Thr Pro Ala Thr Asn Asn Arg Ala Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495
```

```
Glu Lys Ile Asn Gln Ser Leu Ala Phe Ile Arg Lys Ser Asp Glu Leu
            500                 505                 510
Leu His His His His His His His
        515                 520

<210> SEQ ID NO 14
<211> LENGTH: 521
<212> TYPE: PRT
<213> ORGANISM: Artificial Sequence
<220> FEATURE:
<223> OTHER INFORMATION: F11: RSV B1, wt ectodomain

<400> SEQUENCE: 14

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
                20                  25                  30

Tyr Gln Ser Thr Cys Ser Ala Val Ser Arg Gly Tyr Phe Ser Ala Leu
            35                  40                  45

Arg Thr Gly Trp Tyr Thr Ser Val Ile Thr Ile Glu Leu Ser Asn Ile
        50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335
```

```
Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
            500                 505                 510

Leu His His His His His His His
            515                 520

<210> SEQ ID NO 15
<211> LENGTH: 507
<212> TYPE: PRT
<213> ORGANISM: Artificial Sequence
<220> FEATURE:
<223> OTHER INFORMATION: F47: RSV A2, linker stabilized, IZ(S)

<400> SEQUENCE: 15

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
            50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
            85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
            130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
            165                 170                 175
```

Ile Asp Lys Gln Leu Leu Pro Ile Val Asn Lys Gln Ser Cys Ser Ile
            180                 185                 190

Ser Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Glu Lys Ile Glu Ala Ile
465                 470                 475                 480

Glu Lys Lys Ile Glu Ala Ile Glu Lys Lys Ile Glu Ala Gly Gly Ile
                485                 490                 495

Glu Gly Arg His His His His His His His
            500                 505

<210> SEQ ID NO 16
<211> LENGTH: 495
<212> TYPE: PRT
<213> ORGANISM: Artificial Sequence
<220> FEATURE:
<223> OTHER INFORMATION: F47-: RSV A2, linker stabilized, IZ(S)

<400> SEQUENCE: 16

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

```
Tyr Gln Ser Thr Cys Ser Ala Val Ser Lys Gly Tyr Leu Ser Ala Leu
             35                  40                  45

Arg Thr Gly Trp Tyr Thr Ser Val Ile Thr Ile Glu Leu Ser Asn Ile
 50                  55                  60

Lys Lys Asn Lys Cys Asn Gly Thr Asp Ala Lys Ile Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Gln Ala Arg Gly Ser Gly Ser
                100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
        130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Ser Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
```

```
                    450                 455                 460

Glu Phe Asp Ala Ser Ile Ser Gln Val Glu Lys Lys Ile Glu Ala Ile
465                 470                 475                 480

Glu Lys Lys Ile Glu Ala Ile Glu Lys Lys Ile Glu Ala Gly Gly
                485                 490                 495

<210> SEQ ID NO 17
<211> LENGTH: 505
<212> TYPE: PRT
<213> ORGANISM: Artificial Sequence
<220> FEATURE:
<223> OTHER INFORMATION: F43: RSV B1, linker stabilized, IZ(S)

<400

-continued

```
                    325                 330                 335
Lys Val Gln Ser Asn Arg Val Phe Cys Asp Thr Met Asn Ser Leu Thr
                340                 345                 350
Leu Pro Ser Glu Val Ser Leu Cys Asn Thr Asp Ile Phe Asn Ser Lys
            355                 360                 365
Tyr Asp Cys Lys Ile Met Thr Ser Lys Thr Asp Ile Ser Ser Ser Val
        370                 375                 380
Ile Thr Ser Leu Gly Ala Ile Val Ser Cys Tyr Gly Lys Thr Lys Cys
385                 390                 395                 400
Thr Ala Ser Asn Lys Asn Arg Gly Ile Ile Lys Thr Phe Ser Asn Gly
                405                 410                 415
Cys Asp Tyr Val Ser Asn Lys Gly Val Asp Thr Val Ser Val Gly Asn
            420                 425                 430
Thr Leu Tyr Tyr Val Asn Lys Leu Glu Gly Lys Asn Leu Tyr Val Lys
        435                 440                 445
Gly Glu Pro Ile Ile Asn Tyr Tyr Asp Pro Leu Val Phe Pro Ser Asp
450                 455                 460
Glu Phe Asp Ala Ser Ile Ser Gln Val Glu Lys Lys Ile Glu Ala Ile
465                 470                 475                 480
Glu Lys Lys Ile Glu Ala Ile Glu Lys Lys Ile Glu Ala Gly Gly Ile
                485                 490                 495
Glu Gly Arg His His His His His His
                500                 505

<210> SEQ ID NO 18
<211> LENGTH: 534
<212> TYPE: PRT
<213> ORGANISM: Artificial Sequence
<220> FEATURE:
<223> OTHER INFORMATION: F24: RSV B1, linker stabilized, fibritin

<400> SEQUENCE: 18

Met Glu Leu Leu Ile His Arg Leu Ser Ala Ile Phe Leu Thr Leu Ala
1               5                   10                  15
Ile Asn Ala Leu Tyr Leu Thr Ser Ser Gln Asn Ile Thr Glu Glu Phe
            20                  25                  30
Tyr Gln Ser Thr Cys Ser Ala Val Ser Arg Gly Tyr Phe Ser Ala Leu
        35                  40                  45
Arg Thr Gly Trp Tyr Thr Ser Val Ile Thr Ile Glu Leu Ser Asn Ile
    50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Asn Thr Pro Ala Ala Asn Asn Gln Ala Arg Gly Ser Gly Ser
            100                 105                 110
Gly Arg Ser Leu Gly Phe Leu Leu Gly Val Gly Ser Ala Ile Ala Ser
        115                 120                 125
Gly Ile Ala Val Ser Lys Val Leu His Leu Glu Gly Glu Val Asn Lys
    130                 135                 140
Ile Lys Asn Ala Leu Leu Ser Thr Asn Lys Ala Val Val Ser Leu Ser
145                 150                 155                 160
Asn Gly Val Ser Val Leu Thr Ser Lys Val Leu Asp Leu Lys Asn Tyr
                165                 170                 175
Ile Asn Asn Gln Leu Leu Pro Ile Val Asn Gln Gln Ser Cys Arg Ile
```

```
                    180                 185                 190
Ser Asn Ile Glu Thr Val Ile Glu Phe Gln Gln Lys Asn Ser Arg Leu
            195                 200                 205

Leu Glu Ile Asn Arg Glu Phe Ser Val Asn Ala Gly Val Thr Thr Pro
        210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Ile Tyr Gly Val Ile Asp
        275                 280                 285

Thr Pro Cys Trp Lys Leu His Thr Ser Pro Leu Cys Thr Thr Asn Ile
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
            340                 345                 350

Leu Pro Ser Glu Val Ser Leu Cys Asn Thr Asp Ile Phe Asn Ser Lys
        355                 360                 365

Tyr Asp Cys Lys Ile Met Thr Ser Lys Thr Asp Ile Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Leu Glu Gly Lys Asn Leu Tyr Val Lys
        435                 440                 445

Gly Glu Pro Ile Ile Asn Tyr Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

His His His His His His
    530

<210> SEQ ID NO 19
<211> LENGTH: 528
<212> TYPE: PRT
<213> ORGANISM: Artificial Sequence
<220> FEATURE:
<223> OTHER INFORMATION: A2_F24: RSV A2, linker stabilized, fibritin

<400> SEQUENCE: 19

Met Glu Leu Leu Ile Leu Lys Ala Asn Ala Ile Thr Thr Ile Leu Thr
```

-continued

```
  1               5                    10                   15
Ala Val Thr Phe Cys Phe Ala Ser Gly Gln Asn Ile Thr Glu Glu Phe
             20                   25                  30
Tyr Gln Ser Thr Cys Ser Ala Val Ser Lys Gly Tyr Leu Ser Ala Leu
             35                   40                  45
Arg Thr Gly Trp Tyr Thr Ser Val Ile Thr Ile Glu Leu Ser Asn Ile
 50                       55                  60
Lys Lys Asn Lys Cys Asn Gly Thr Asp Ala Lys Ile Lys Leu Ile Lys
 65                  70                  75                  80
Gln Glu Leu Asp Lys Tyr Lys Asn Ala Val Thr Glu Leu Gln Leu Leu
                  85                  90                  95
Met Gln Ser Thr Pro Ala Thr Asn Asn Gln Ala Arg Gly Ser Gly Ser
             100                  105                 110
Gly Arg Ser Leu Gly Phe Leu Leu Gly Val Gly Ser Ala Ile Ala Ser
             115                  120                 125
Gly Val Ala Val Ser Lys Val Leu His Leu Glu Gly Glu Val Asn Lys
 130                 135                 140
Ile Lys Ser Ala Leu Leu Ser Thr Asn Lys Ala Val Val Ser Leu Ser
145                  150                 155                 160
Asn Gly Val Ser Val Leu Thr Ser Lys Val Leu Asp Leu Lys Asn Tyr
                 165                 170                 175
Ile Asp Lys Gln Leu Leu Pro Ile Val Asn Lys Gln Ser Cys Ser Ile
             180                  185                 190
Ser Asn Ile Glu Thr Val Ile Glu Phe Gln Gln Lys Asn Asn Arg Leu
             195                  200                 205
Leu Glu Ile Thr Arg Glu Phe Ser Val Asn Ala Gly Val Thr Thr Pro
 210                 215                 220
Val Ser Thr Tyr Met Leu Thr Asn Ser Glu Leu Leu Ser Leu Ile Asn
225                  230                 235                 240
Asp Met Pro Ile Thr Asn Asp Gln Lys Lys Leu Met Ser Asn Asn Val
             245                  250                 255
Gln Ile Val Arg Gln Gln Ser Tyr Ser Ile Met Ser Ile Ile Lys Glu
             260                  265                 270
Glu Val Leu Ala Tyr Val Val Gln Leu Pro Leu Tyr Gly Val Ile Asp
             275                  280                 285
Thr Pro Cys Trp Lys Leu His Thr Ser Pro Leu Cys Thr Thr Asn Thr
             290                  295                 300
Lys Glu Gly Ser Asn Ile Cys Leu Thr Arg Thr Asp Arg Gly Trp Tyr
305                  310                 315                 320
Cys Asp Asn Ala Gly Ser Val Ser Phe Phe Pro Gln Ala Glu Thr Cys
                 325                  330                 335
Lys Val Gln Ser Asn Arg Val Phe Cys Asp Thr Met Asn Ser Leu Thr
             340                  345                 350
Leu Pro Ser Glu Val Asn Leu Cys Asn Val Asp Ile Phe Asn Pro Lys
             355                  360                 365
Tyr Asp Cys Lys Ile Met Thr Ser Lys Thr Asp Val Ser Ser Ser Val
 370                 375                 380
Ile Thr Ser Leu Gly Ala Ile Val Ser Cys Tyr Gly Lys Thr Lys Cys
385                  390                 395                 400
Thr Ala Ser Asn Lys Asn Arg Gly Ile Ile Lys Thr Phe Ser Asn Gly
                 405                  410                 415
Cys Asp Tyr Val Ser Asn Lys Gly Val Asp Thr Val Ser Val Gly Asn
             420                  425                 430
```

```
Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525
```

<210> SEQ ID NO 20
<211> LENGTH: 528
<212> TYPE: PRT
<213> ORGANISM: Artificial Sequence
<220> FEATURE:
<223> OTHER INFORMATION: F24-: RSV B1, linker stabilized, fibritin

<400> SEQUENCE: 20

```
Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Ile Ala Val Ser Lys Val Leu His Leu Glu Gly Glu Val Asn Lys
    130                 135                 140

Ile Lys Asn Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
            180                 185                 190

Ser Asn Ile Glu Thr Val Ile Glu Phe Gln Gln Lys Asn Ser Arg Leu
        195                 200                 205

Leu Glu Ile Asn Arg Glu Phe Ser Val Asn Ala Gly Val Thr Thr Pro
    210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
            260                 265                 270
```

-continued

Glu Val Leu Ala Tyr Val Val Gln Leu Pro Ile Tyr Gly Val Ile Asp
         275                 280                 285

Thr Pro Cys Trp Lys Leu His Thr Ser Pro Leu Cys Thr Thr Asn Ile
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
             325                 330                 335

Lys Val Gln Ser Asn Arg Val Phe Cys Asp Thr Met Asn Ser Leu Thr
             340                 345                 350

Leu Pro Ser Glu Val Ser Leu Cys Asn Thr Asp Ile Phe Asn Ser Lys
         355                 360                 365

Tyr Asp Cys Lys Ile Met Thr Ser Lys Thr Asp Ile Ser Ser Ser Val
         370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
             405                 410                 415

Cys Asp Tyr Val Ser Asn Lys Gly Val Asp Thr Val Ser Val Gly Asn
             420                 425                 430

Thr Leu Tyr Tyr Val Asn Lys Leu Glu Gly Lys Asn Leu Tyr Val Lys
         435                 440                 445

Gly Glu Pro Ile Ile Asn Tyr Tyr Asp Pro Leu Val Phe Pro Ser Asp
         450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
             485                 490                 495

Tyr Ile Pro Glu Ala Pro Arg Asp Gly Gln Ala Tyr Val Arg Lys Asp
             500                 505                 510

Gly Glu Trp Val Leu Leu Ser Thr Phe Leu Gly Gly Ile Glu Gly Arg
         515                 520                 525

<210> SEQ ID NO 21
<211> LENGTH: 528
<212> TYPE: PRT
<213> ORGANISM: Artificial Sequence
<220> FEATURE:
<223> OTHER INFORMATION: A2_F24 N67I+S215P: A2, linker stabilized,
      fibritin

<400> SEQUENCE: 21

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
             20                  25                  30

Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
         50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
             85                  90                  95

Met Gln Ser Thr Pro Ala Thr Asn Asn Gln Ala Arg Gly Ser Gly Ser

```
                100             105             110
Gly Arg Ser Leu Gly Phe Leu Leu Gly Val Gly Ser Ala Ile Ala Ser
            115             120             125

Gly Val Ala Val Ser Lys Val Leu His Leu Glu Gly Glu Val Asn Lys
        130             135             140

Ile Lys Ser Ala Leu Leu Ser Thr Asn Lys Ala Val Val Ser Leu Ser
145             150             155             160

Asn Gly Val Ser Val Leu Thr Ser Lys Val Leu Asp Leu Lys Asn Tyr
                165             170             175

Ile Asp Lys Gln Leu Leu Pro Ile Val Asn Lys Gln Ser Cys Ser Ile
            180             185             190

Pro Asn Ile Glu Thr Val Ile Glu Phe Gln Gln Lys Asn Asn Arg Leu
        195             200             205

Leu Glu Ile Thr Arg Glu Phe Ser Val Asn Ala Gly Val Thr Thr Pro
    210             215             220

Val Ser Thr Tyr Met Leu Thr Asn Ser Glu Leu Leu Ser Leu Ile Asn
225             230             235             240

Asp Met Pro Ile Thr Asn Asp Gln Lys Lys Leu Met Ser Asn Asn Val
                245             250             255

Gln Ile Val Arg Gln Gln Ser Tyr Ser Ile Met Ser Ile Ile Lys Glu
            260             265             270

Glu Val Leu Ala Tyr Val Val Gln Leu Pro Leu Tyr Gly Val Ile Asp
        275             280             285

Thr Pro Cys Trp Lys Leu His Thr Ser Pro Leu Cys Thr Thr Asn Thr
    290             295             300

Lys Glu Gly Ser Asn Ile Cys Leu Thr Arg Thr Asp Arg Gly Trp Tyr
305             310             315             320

Cys Asp Asn Ala Gly Ser Val Ser Phe Phe Pro Gln Ala Glu Thr Cys
                325             330             335

Lys Val Gln Ser Asn Arg Val Phe Cys Asp Thr Met Asn Ser Leu Thr
            340             345             350

Leu Pro Ser Glu Val Asn Leu Cys Asn Val Asp Ile Phe Asn Pro Lys
        355             360             365

Tyr Asp Cys Lys Ile Met Thr Ser Lys Thr Asp Val Ser Ser Ser Val
    370             375             380

Ile Thr Ser Leu Gly Ala Ile Val Ser Cys Tyr Gly Lys Thr Lys Cys
385             390             395             400

Thr Ala Ser Asn Lys Asn Arg Gly Ile Ile Lys Thr Phe Ser Asn Gly
                405             410             415

Cys Asp Tyr Val Ser Asn Lys Gly Val Asp Thr Val Ser Val Gly Asn
            420             425             430

Thr Leu Tyr Tyr Val Asn Lys Gln Glu Gly Lys Ser Leu Tyr Val Lys
        435             440             445

Gly Glu Pro Ile Ile Asn Phe Tyr Asp Pro Leu Val Phe Pro Ser Asp
    450             455             460

Glu Phe Asp Ala Ser Ile Ser Gln Val Asn Glu Lys Ile Asn Gln Ser
465             470             475             480

Leu Ala Phe Ile Arg Lys Ser Asp Glu Leu Leu Ser Ala Ile Gly Gly
                485             490             495

Tyr Ile Pro Glu Ala Pro Arg Asp Gly Gln Ala Tyr Val Arg Lys Asp
            500             505             510

Gly Glu Trp Val Leu Leu Ser Thr Phe Leu Gly Gly Ile Glu Gly Arg
        515             520             525
```

-continued

```
<210> SEQ ID NO 22
<211> LENGTH: 528
<212> TYPE: PRT
<213> ORGANISM:

```
                355                 360                 365
Tyr Asp Cys Lys Ile Met Thr Ser Lys Thr Asp Ile Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Leu Glu Gly Lys Asn Leu Tyr Val Lys
            435                 440                 445

Gly Glu Pro Ile Ile Asn Tyr Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 23
<211> LENGTH: 528
<212> TYPE: PRT
<213> ORGANISM: Artificial Sequence
<220> FEATURE:
<223> OTHER INFORMATION: A2_F24 N67I+E92D: RSV A2, linker stabilized,
      fibritin

<400> SEQUENCE: 23

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190
```

Ser Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 24
<211> LENGTH: 528
<212> TYPE: PRT
<213> ORGANISM: Artificial Sequence
<220> FEATURE:
<223> OTHER INFORMATION: F24- N67I+E92D RSV B1, linker stabilized,
      fibritin

<400> SEQUENCE: 24

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

-continued

```
Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
 50                  55                  60

Lys Glu Ile Lys Cys Asn Gly Thr Asp Thr Lys Val Lys Leu Ile Lys
 65                  70                  75                  80

Gln Glu Leu Asp Lys Tyr Lys Asn Ala Val Thr Asp Leu Gln Leu Leu
                 85                  90                  95

Met Gln Asn Thr Pro Ala Ala Asn Asn Gln Ala Arg Gly Ser Gly Ser
                100                 105                 110

Gly Arg Ser Leu Gly Phe Leu Leu Gly Val Gly Ser Ala Ile Ala Ser
                115                 120                 125

Gly Ile Ala Val Ser Lys Val Leu His Leu Glu Gly Glu Val Asn Lys
130                 135                 140

Ile Lys Asn Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
                180                 185                 190

Ser Asn Ile Glu Thr Val Ile Glu Phe Gln Gln Lys Asn Ser Arg Leu
                195                 200                 205

Leu Glu Ile Asn Arg Glu Phe Ser Val Asn Ala Gly Val Thr Thr Pro
                210                 215                 220

Leu Ser Thr Tyr Met Leu Thr Asn Ser Glu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Ile Tyr Gly Val Ile Asp
                275                 280                 285

Thr Pro Cys Trp Lys Leu His Thr Ser Pro Leu Cys Thr Thr Asn Ile
                290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
                340                 345                 350

Leu Pro Ser Glu Val Ser Leu Cys Asn Thr Asp Ile Phe Asn Ser Lys
                355                 360                 365

Tyr Asp Cys Lys Ile Met Thr Ser Lys Thr Asp Ile Ser Ser Ser Val
                370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Leu Glu Gly Lys Asn Leu Tyr Val Lys
                435                 440                 445
```

```
Gly Glu Pro Ile Ile Asn Tyr Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
            515                 520                 525

<210> SEQ ID NO 25
<211> LENGTH: 528
<212> TYPE: PRT
<213> ORGANISM: Artificial Sequence
<220> FEATURE:
<223> OTHER INFORMATION: A2_F24 N67I+K465Q RSV A2, linker stabilized,
      fibritin

<400> SEQUENCE: 25

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285
```

```
Thr Pro Cys Trp Lys Leu His Thr Ser Pro Leu Cys Thr Thr Asn Thr
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Gln Ser Leu Tyr Val Lys
        435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 26
<211> LENGTH: 528
<212> TYPE: PRT
<213> ORGANISM: Artificial Sequence
<220> FEATURE:
<223> OTHER INFORMATION: F24- N67I+K465Q RSV B1, linker stabilized,
      fibritin

<400> SEQUENCE: 26

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Gln Ala Arg Gly Ser Gly Ser
            100                 105                 110

Gly Arg Ser Leu Gly Phe Leu Leu Gly Val Gly Ser Ala Ile Ala Ser
```

```
            115                 120                 125
Gly Ile Ala Val Ser Lys Val Leu His Leu Glu Gly Glu Val Asn Lys
    130                 135                 140

Ile Lys Asn Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
            180                 185                 190

Pro Asn Ile Glu Thr Val Ile Glu Phe Gln Gln Lys Asn Ser Arg Leu
        195                 200                 205

Leu Glu Ile Asn Arg Glu Phe Ser Val Asn Ala Gly Val Thr Thr Pro
    210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Ile Tyr Gly Val Ile Asp
        275                 280                 285

Thr Pro Cys Trp Lys Leu His Thr Ser Pro Leu Cys Thr Thr Asn Ile
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
            340                 345                 350

Leu Pro Ser Glu Val Ser Leu Cys Asn Thr Asp Ile Phe Asn Ser Lys
        355                 360                 365

Tyr Asp Cys Lys Ile Met Thr Ser Lys Thr Asp Ile Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Leu Glu Gly Gln Asn Leu Tyr Val Lys
        435                 440                 445

Gly Glu Pro Ile Ile Asn Tyr Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 27
```

<211> LENGTH: 528
<212> TYPE: PRT
<213> ORGANISM: Artificial Sequence
<220> FEATURE:
<223> OTHER INFORMATION: A2_F24 N67I+S46G RSV A2, linker stabilized, fibritin

<400> SEQUENCE: 27

```
Met Glu Leu Leu Ile Le

```
                    370                 375                 380
Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                    405                 410                 415

Cys Asp Tyr Val Ser Asn Lys Gly Val Asp Thr Val Ser Val Gly Asn
                    420                 425                 430

Thr Leu Tyr Tyr Val Asn Lys Gln Glu Gly Lys Ser Leu Tyr Val Lys
                    435                 440                 445

Gly Glu Pro Ile Ile Asn Phe Tyr Asp Pro Leu Val Phe Pro Ser Asp
                    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                    485                 490                 495

Tyr Ile Pro Glu Ala Pro Arg Asp Gly Gln Ala Tyr Val Arg Lys Asp
                    500                 505                 510

Gly Glu Trp Val Leu Leu Ser Thr Phe Leu Gly Gly Ile Glu Gly Arg
                    515                 520                 525

<210> SEQ ID NO 28
<211> LENGTH: 528
<212> TYPE: PRT
<213> ORGANISM: Artificial Sequence
<220> FEATURE:
<223> OTHER INFORMATION: F24- N67I+S46G RSV B1, linker stabilized,
      fibritin

<400> SEQUENCE: 28

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
                20                  25                  30

Tyr Gln Ser Thr Cys Ser Ala Val Ser Arg Gly Tyr Phe Gly Ala Leu
                35                  40                  45

Arg Thr Gly Trp Tyr Thr Ser Val Ile Thr Ile Glu Leu Ser Asn Ile
50                  55                  60

Lys Glu Ile Lys Cys Asn Gly Thr Asp Thr Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Asn Thr Pro Ala Ala Asn Asn Gln Ala Arg Gly Ser Gly Ser
                100                 105                 110

Gly Arg Ser Leu Gly Phe Leu Leu Gly Val Gly Ser Ala Ile Ala Ser
                115                 120                 125

Gly Ile Ala Val Ser Lys Val Leu His Leu Glu Gly Glu Val Asn Lys
                130                 135                 140

Ile Lys Asn Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
                180                 185                 190

Ser Asn Ile Glu Thr Val Ile Glu Phe Gln Gln Lys Asn Ser Arg Leu
                195                 200                 205
```

-continued

Leu Glu Ile Asn Arg Glu Phe Ser Val Asn Ala Gly Val Thr Thr Pro
210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Ile Tyr Gly Val Ile Asp
        275                 280                 285

Thr Pro Cys Trp Lys Leu His Thr Ser Pro Leu Cys Thr Thr Asn Ile
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
            340                 345                 350

Leu Pro Ser Glu Val Ser Leu Cys Asn Thr Asp Ile Phe Asn Ser Lys
        355                 360                 365

Tyr Asp Cys Lys Ile Met Thr Ser Lys Thr Asp Ile Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Leu Glu Gly Lys Asn Leu Tyr Val Lys
        435                 440                 445

Gly Glu Pro Ile Ile Asn Tyr Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 29
<211> LENGTH: 528
<212> TYPE: PRT
<213> ORGANISM: Artificial Sequence
<220> FEATURE:
<223> OTHER INFORMATION: A2_F24 E92D+S215P: A2, linker stabilized,
      fibritin

<400> SEQUENCE: 29

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

```
Arg Thr Gly Trp Tyr Thr Ser Val Ile Thr Ile Glu Leu Ser Asn Ile
 50                  55                  60

Lys Lys Asn Lys Cys Asn Gly Thr Asp Ala Lys Ile Lys Leu Ile Lys
 65                  70                  75                  80

Gln Glu Leu Asp Lys Tyr Lys Asn Ala Val Thr Asp Leu Gln Leu Leu
                 85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460
```

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 30
<211> LENGTH: 528
<212> TYPE: PRT
<213> ORGANISM: Artificial Sequence
<220> FEATURE:
<223> OTHER INFORMATION: F24-E92D+S215P: RSV B1, linker stabilized, fibritin

<400> SEQUENCE: 30

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Asn Thr Pro Ala Ala Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Ile Ala Val Ser Lys Val Leu His Leu Glu Gly Glu Val Asn Lys
    130                 135                 140

Ile Lys Asn Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
            180                 185                 190

Pro Asn Ile Glu Thr Val Ile Glu Phe Gln Gln Lys Asn Ser Arg Leu
        195                 200                 205

Leu Glu Ile Asn Arg Glu Phe Ser Val Asn Ala Gly Val Thr Thr Pro
    210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Ile Tyr Gly Val Ile Asp
        275                 280                 285

Thr Pro Cys Trp Lys Leu His Thr Ser Pro Leu Cys Thr Thr Asn Ile
    290                 295                 300

```
Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
                340                 345                 350

Leu Pro Ser Glu Val Ser Leu Cys Asn Thr Asp Ile Phe Asn Ser Lys
            355                 360                 365

Tyr Asp Cys Lys Ile Met Thr Ser Lys Thr Asp Ile Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Leu Glu Gly Lys Asn Leu Tyr Val Lys
            435                 440                 445

Gly Glu Pro Ile Ile Asn Tyr Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 31
<211> LENGTH: 528
<212> TYPE: PRT
<213> ORGANISM: Artificial Sequence
<220> FEATURE:
<223> OTHER INFORMATION: A2_F24 N67I+S215P+K508E: A2, linker stabilized,
      fibritin

<400> SEQUENCE: 31

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
```

```
            130                 135                 140
Ile Lys Ser Ala Leu Leu Ser Thr Asn Lys Ala Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Glu Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 32
<211> LENGTH: 528
<212> TYPE: PRT
<213> ORGANISM: Artificial Sequence
```

<220> FEATURE:
<223> OTHER INFORMATION: A2_F24 N67I+S215P+E487I: A2, linker stabilized, fibritin

<400> SEQUENCE: 32

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
```

```
                385                 390                 395                 400

Thr Ala Ser Asn Lys Asn Arg Gly Ile Ile Lys Thr Phe Ser Asn Gly
                        405                 410                 415

Cys Asp Tyr Val Ser Asn Lys Gly Val Asp Thr Val Ser Val Gly Asn
                        420                 425                 430

Thr Leu Tyr Tyr Val Asn Lys Gln Glu Gly Lys Ser Leu Tyr Val Lys
                        435                 440                 445

Gly Glu Pro Ile Ile Asn Phe Tyr Asp Pro Leu Val Phe Pro Ser Asp
                        450                 455                 460

Ile Phe Asp Ala Ser Ile Ser Gln Val Asn Glu Lys Ile Asn Gln Ser
        465                 470                 475                 480

Leu Ala Phe Ile Arg Lys Ser Asp Glu Leu Leu Ser Ala Ile Gly Gly
                        485                 490                 495

Tyr Ile Pro Glu Ala Pro Arg Asp Gly Gln Ala Tyr Val Arg Lys Asp
                        500                 505                 510

Gly Glu Trp Val Leu Leu Ser Thr Phe Leu Gly Gly Ile Glu Gly Arg
                        515                 520                 525

<210> SEQ ID NO 33
<211> LENGTH: 528
<212> TYPE: PRT
<213> ORGANISM: Artificial Sequence
<220> FEATURE:
<223> OTHER INFORMATION: A2_F24 N67I+S215P+E487Q: A2, linker stabilized,
      fibritin

<400> SEQUENCE: 33

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
            50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
                100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
                180                 185                 190

Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
    210                 215                 220
```

-continued

```
Val Ser Thr Tyr Met Leu Thr Asn Ser Glu Leu Ser Leu Ile Asn
225                 230                 235                 240

Asp Met Pro Ile Thr Asn Asp Gln Lys Lys Leu Met Ser Asn Asn Val
            245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Gln Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 34
<211> LENGTH: 528
<212> TYPE: PRT
<213> ORGANISM: Artificial Sequence
<220> FEATURE:
<223> OTHER INFORMATION: A2_F24 N67I+S215P+E487N: A2, linker stabilized,
      fibritin

<400> SEQUENCE: 34

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60
```

-continued

```
Lys Lys Ile Lys Cys Asn Gly Thr Asp Ala Lys Ile Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Asn Phe Asp Ala Ser Ile Ser Gln Val Asn Glu Lys Ile Asn Gln Ser
465                 470                 475                 480
```

-continued

```
Leu Ala Phe Ile Arg Lys Ser Asp Glu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 35
<211> LENGTH: 528
<212> TYPE: PRT
<213> ORGANISM: Artificial Sequence
<220> FEATURE:
<223> OTHER INFORMATION: A2_F24 N67I+S215P+D486N: A2, linker stabilized,
      fibritin

<400> SEQUENCE: 35

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320
```

-continued

```
Cys Asp Asn Ala Gly Ser Val Ser Phe Phe Pro Gln Ala Glu Thr Cys
            325                 330                 335
Lys Val Gln Ser Asn Arg Val Phe Cys Asp Thr Met Asn Ser Leu Thr
        340                 345                 350
Leu Pro Ser Glu Val Asn Leu Cys Asn Val Asp Ile Phe Asn Pro Lys
    355                 360                 365
Tyr Asp Cys Lys Ile Met Thr Ser Lys Thr Asp Val Ser Ser Ser Val
370                 375                 380
Ile Thr Ser Leu Gly Ala Ile Val Ser Cys Tyr Gly Lys Thr Lys Cys
385                 390                 395                 400
Thr Ala Ser Asn Lys Asn Arg Gly Ile Ile Lys Thr Phe Ser Asn Gly
            405                 410                 415
Cys Asp Tyr Val Ser Asn Lys Gly Val Asp Thr Val Ser Val Gly Asn
        420                 425                 430
Thr Leu Tyr Tyr Val Asn Lys Gln Glu Gly Lys Ser Leu Tyr Val Lys
    435                 440                 445
Gly Glu Pro Ile Ile Asn Phe Tyr Asp Pro Leu Val Phe Pro Ser Asn
450                 455                 460
Glu Phe Asp Ala Ser Ile Ser Gln Val Asn Glu Lys Ile Asn Gln Ser
465                 470                 475                 480
Leu Ala Phe Ile Arg Lys Ser Asp Glu Leu Leu Ser Ala Ile Gly Gly
            485                 490                 495
Tyr Ile Pro Glu Ala Pro Arg Asp Gly Gln Ala Tyr Val Arg Lys Asp
        500                 505                 510
Gly Glu Trp Val Leu Leu Ser Thr Phe Leu Gly Gly Ile Glu Gly Arg
    515                 520                 525

<210> SEQ ID NO 36
<211> LENGTH: 528
<212> TYPE: PRT
<213> ORGANISM: Artificial Sequence
<220> FEATURE:
<223> OTHER INFORMATION: A2_F24 N67I+S215P+K465E: A2, linker stabilized,
      fibritin

<400> SEQUENCE: 36

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Lys Ile Lys Cys Asn Gly Thr Asp Ala Lys Ile Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Gln Ala Arg Gly Ser Gly Ser
            100                 105                 110
Gly Arg Ser Leu Gly Phe Leu Leu Gly Val Gly Ser Ala Ile Ala Ser
        115                 120                 125
Gly Val Ala Val Ser Lys Val Leu His Leu Glu Gly Glu Val Asn Lys
    130                 135                 140
Ile Lys Ser Ala Leu Leu Ser Thr Asn Lys Ala Val Val Ser Leu Ser
```

```
           145                 150                 155                 160
Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
                180                 185                 190

Pro Asn Ile Glu Thr Val Ile Glu Phe Gln Gln Lys Asn Asn Arg Leu
                195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Leu Tyr Gly Val Ile Asp
                275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
                355                 360                 365

Tyr Asp Cys Lys Ile Met Thr Ser Lys Thr Asp Val Ser Ser Ser Val
                370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Glu Ser Leu Tyr Val Lys
                435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
                515                 520                 525

<210> SEQ ID NO 37
<211> LENGTH: 528
<212> TYPE: PRT
<213> ORGANISM: Artificial Sequence
<220> FEATURE:
<223> OTHER INFORMATION: A2_F24 N67I+S215P+K465Q: A2, linker stabilized,
      fibritin
```

<400> SEQUENCE: 37

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
```

```
                    405                 410                 415
        Cys Asp Tyr Val Ser Asn Lys Gly Val Asp Thr Val Ser Val Gly Asn
                    420                 425                 430

Thr Leu Tyr Tyr Val Asn Lys Gln Glu Gly Gln Ser Leu Tyr Val Lys
                    435                 440                 445

Gly Glu Pro Ile Ile Asn Phe Tyr Asp Pro Leu Val Phe Pro Ser Asp
                    450                 455                 460

Glu Phe Asp Ala Ser Ile Ser Gln Val Asn Glu Lys Ile Asn Gln Ser
        465                 470                 475                 480

Leu Ala Phe Ile Arg Lys Ser Asp Glu Leu Leu Ser Ala Ile Gly Gly
                        485                 490                 495

Tyr Ile Pro Glu Ala Pro Arg Asp Gly Gln Ala Tyr Val Arg Lys Asp
                        500                 505                 510

Gly Glu Trp Val Leu Leu Ser Thr Phe Leu Gly Gly Ile Glu Gly Arg
                        515                 520                 525

<210> SEQ ID NO 38
<211> LENGTH: 528
<212> TYPE: PRT
<213> ORGANISM: Artificial Sequence
<220> FEATURE:
<223> OTHER INFORMATION: A2_F24 N67I+S215P+N426S: A2, linker stabilized,
      fibritin

<400> SEQUENCE: 38

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240
```

-continued

Asp Met Pro Ile Thr Asn Asp Gln Lys Lys Leu Met Ser Asn Asn Val
            245                 250                 255

Gln Ile Val Arg Gln Gln Ser Tyr Ser Ile Met Ser Ile Ile Lys Glu
        260                 265                 270

Glu Val Leu Ala Tyr Val Val Gln Leu Pro Leu Tyr Gly Val Ile Asp
    275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Ser Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 39
<211> LENGTH: 528
<212> TYPE: PRT
<213> ORGANISM: Artificial Sequence
<220> FEATURE:
<223> OTHER INFORMATION: A2_F24 N67I+S215P+K421N: A2, linker stabilized,
      fibritin

<400> SEQUENCE: 39

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

```
Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Asn Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495
```

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 40
<211> LENGTH: 528
<212> TYPE: PRT
<213> ORGANISM: Artificial Sequence
<220> FEATURE:
<223> OTHER INFORMATION: A2_F24 N67I+S215P+K209Q: A2, linker stabilized,
      fibritin

<400> SEQUENCE: 40

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Gln Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

```
Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
            370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
            515                 520                 525

<210> SEQ ID NO 41
<211> LENGTH: 528
<212> TYPE: PRT
<213> ORGANISM: Artificial Sequence
<220> FEATURE:
<223> OTHER INFORMATION: A2_F24 N67I+S215P+K201Q: A2, linker stabilized,
      fibritin

<400> SEQUENCE: 41

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
            130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
```

165                 170                 175
Ile Asp Gln Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
        210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 42
<211> LENGTH: 528
<212> TYPE: PRT
<213> ORGANISM: Artificial Sequence
<220> FEATURE:
<223> OTHER INFORMATION: A2_F24 N67I+S215P+V185N: A2, linker stabilized,
      fibritin

<400> SEQUENCE: 42

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Asn Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
```

-continued

```
                420             425             430
Thr Leu Tyr Tyr Val Asn Lys Gln Glu Gly Lys Ser Leu Tyr Val Lys
            435             440             445
Gly Glu Pro Ile Ile Asn Phe Tyr Asp Pro Leu Val Phe Pro Ser Asp
            450             455             460
Glu Phe Asp Ala Ser Ile Ser Gln Val Asn Glu Lys Ile Asn Gln Ser
465             470             475             480
Leu Ala Phe Ile Arg Lys Ser Asp Glu Leu Leu Ser Ala Ile Gly Gly
            485             490             495
Tyr Ile Pro Glu Ala Pro Arg Asp Gly Gln Ala Tyr Val Arg Lys Asp
            500             505             510
Gly Glu Trp Val Leu Leu Ser Thr Phe Leu Gly Gly Ile Glu Gly Arg
            515             520             525

<210> SEQ ID NO 43
<211> LENGTH: 528
<212> TYPE: PRT
<213> ORGANISM: Artificial Sequence
<220> FEATURE:
<223> OTHER INFORMATION: A2_F24 N67I+S215P+G184N: A2, linker stabilized,
      fibritin

<400> SEQUENCE: 43

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
        50                  55                  60
Lys Lys Ile Lys Cys Asn Gly Thr Asp Ala Lys Ile Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Gln Ala Arg Gly Ser Gly Ser
            100                 105                 110
Gly Arg Ser Leu Gly Phe Leu Leu Gly Val Gly Ser Ala Ile Ala Ser
            115                 120                 125
Gly Val Ala Val Ser Lys Val Leu His Leu Glu Gly Glu Val Asn Lys
        130                 135                 140
Ile Lys Ser Ala Leu Leu Ser Thr Asn Lys Ala Val Val Ser Leu Ser
145                 150                 155                 160
Asn Asn Val Ser Val Leu Thr Ser Lys Val Leu Asp Leu Lys Asn Tyr
                165                 170                 175
Ile Asp Lys Gln Leu Leu Pro Ile Val Asn Lys Gln Ser Cys Ser Ile
            180                 185                 190
Pro Asn Ile Glu Thr Val Ile Glu Phe Gln Gln Lys Asn Asn Arg Leu
            195                 200                 205
Leu Glu Ile Thr Arg Glu Phe Ser Val Asn Ala Gly Val Thr Thr Pro
        210                 215                 220
Val Ser Thr Tyr Met Leu Thr Asn Ser Glu Leu Leu Ser Leu Ile Asn
225                 230                 235                 240
Asp Met Pro Ile Thr Asn Asp Gln Lys Lys Leu Met Ser Asn Asn Val
                245                 250                 255
```

-continued

```
Gln Ile Val Arg Gln Gln Ser Tyr Ser Ile Met Ser Ile Ile Lys Glu
                260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 44
<211> LENGTH: 528
<212> TYPE: PRT
<213> ORGANISM: Artificial Sequence
<220> FEATURE:
<223> OTHER INFORMATION: A2_F24 N67I+S215P+N175P: A2, linker stabilized,
      fibritin

<400> SEQUENCE: 44

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95
```

```
Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Pro Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510
```

```
Gly Glu Trp Val Leu Leu Ser Thr Phe Leu Gly Ile Glu Gly Arg
            515                 520                 525
```

<210> SEQ ID NO 45
<211> LENGTH: 528
<212> TYPE: PRT
<213> ORGANISM: Artificial Sequence
<220> FEATURE:
<223> OTHER INFORMATION: A2_F24 N67I+S215P+E92D: A2, linker stabilized, fibritin

<400> SEQUENCE: 45

```
Met Glu Leu Leu Ile Leu Lys Ala Asn Ala Ile Thr Thr Ile Leu Thr
  1               5                  10                  15

Ala Val Thr Phe Cys Phe Ala Ser Gly Gln Asn Ile Thr Glu Glu Phe
                 20                  25                  30

Tyr Gln Ser Thr Cys Ser Ala Val Ser Lys Gly Tyr Leu Ser Ala Leu
             35                  40                  45

Arg Thr Gly Trp Tyr Thr Ser Val Ile Thr Ile Glu Leu Ser Asn Ile
 50                  55                  60

Lys Lys Ile Lys Cys Asn Gly Thr Asp Ala Lys Ile Lys Leu Ile Lys
 65                  70                  75                  80

Gln Glu Leu Asp Lys Tyr Lys Asn Ala Val Thr Asp Leu Gln Leu Leu
                 85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
        210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350
```

```
Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
                435                 440                 445

Gly Glu Pro Ile Ile Asn Phe Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
        500                 505                 510

Gly Glu Trp Val Leu Leu Ser Thr Phe Leu Gly Gly Ile Glu Gly Arg
        515                 520                 525

<210> SEQ ID NO 46
<211> LENGTH: 528
<212> TYPE: PRT
<213> ORGANISM: Artificial Sequence
<220> FEATURE:
<223> OTHER INFORMATION: A2_F24 N67I+S215P+K80E: A2, linker stabilized,
      fibritin

<400> SEQUENCE: 46

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Glu
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
```

```
                    180                 185                 190
Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
        210                 215                 220

Val Ser Thr Tyr Met Leu Thr Asn Ser Glu Leu Ser Leu Ile Asn
225                 230                 235                 240

Asp Met Pro Ile Thr Asn Asp Gln Lys Lys Leu Met Ser Asn Asn Val
                    245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                    325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                    405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                    485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 47
<211> LENGTH: 528
<212> TYPE: PRT
<213> ORGANISM: Artificial Sequence
<220> FEATURE:
<223> OTHER INFORMATION: A2_F24 N67I+S215P+K77E: A2, linker stabilized,
      fibritin

<400> SEQUENCE: 47

Met Glu Leu Leu Ile Leu Lys Ala Asn Ala Ile Thr Thr Ile Leu Thr
1               5                   10                  15
```

-continued

```
Ala Val Thr Phe Cys Phe Ala Ser Gly Gln Asn Ile Thr Glu Phe
                20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
        50                  55                  60
Lys Lys Ile Lys Cys Asn Gly Thr Asp Ala Lys Ile Glu Leu Ile Lys
 65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Gln Ala Arg Gly Ser Gly Ser
            100                 105                 110
Gly Arg Ser Leu Gly Phe Leu Leu Gly Val Gly Ser Ala Ile Ala Ser
        115                 120                 125
Gly Val Ala Val Ser Lys Val Leu His Leu Glu Gly Glu Val Asn Lys
130                 135                 140
Ile Lys Ser Ala Leu Leu Ser Thr Asn Lys Ala Val Val Ser Leu Ser
145                 150                 155                 160
Asn Gly Val Ser Val Leu Thr Ser Lys Val Leu Asp Leu Lys Asn Tyr
                165                 170                 175
Ile Asp Lys Gln Leu Leu Pro Ile Val Asn Lys Gln Ser Cys Ser Ile
            180                 185                 190
Pro Asn Ile Glu Thr Val Ile Glu Phe Gln Gln Lys Asn Asn Arg Leu
        195                 200                 205
Leu Glu Ile Thr Arg Glu Phe Ser Val Asn Ala Gly Val Thr Thr Pro
210                 215                 220
Val Ser Thr Tyr Met Leu Thr Asn Ser Glu Leu Leu Ser Leu Ile Asn
225                 230                 235                 240
Asp Met Pro Ile Thr Asn Asp Gln Lys Lys Leu Met Ser Asn Asn Val
                245                 250                 255
Gln Ile Val Arg Gln Gln Ser Tyr Ser Ile Met Ser Ile Ile Lys Glu
            260                 265                 270
Glu Val Leu Ala Tyr Val Val Gln Leu Pro Leu Tyr Gly Val Ile Asp
        275                 280                 285
Thr Pro Cys Trp Lys Leu His Thr Ser Pro Leu Cys Thr Thr Asn Thr
290                 295                 300
Lys Glu Gly Ser Asn Ile Cys Leu Thr Arg Thr Asp Arg Gly Trp Tyr
305                 310                 315                 320
Cys Asp Asn Ala Gly Ser Val Ser Phe Phe Pro Gln Ala Glu Thr Cys
                325                 330                 335
Lys Val Gln Ser Asn Arg Val Phe Cys Asp Thr Met Asn Ser Leu Thr
            340                 345                 350
Leu Pro Ser Glu Val Asn Leu Cys Asn Val Asp Ile Phe Asn Pro Lys
        355                 360                 365
Tyr Asp Cys Lys Ile Met Thr Ser Lys Thr Asp Val Ser Ser Ser Val
370                 375                 380
Ile Thr Ser Leu Gly Ala Ile Val Ser Cys Tyr Gly Lys Thr Lys Cys
385                 390                 395                 400
Thr Ala Ser Asn Lys Asn Arg Gly Ile Ile Lys Thr Phe Ser Asn Gly
                405                 410                 415
Cys Asp Tyr Val Ser Asn Lys Gly Val Asp Thr Val Ser Val Gly Asn
            420                 425                 430
Thr Leu Tyr Tyr Val Asn Lys Gln Glu Gly Lys Ser Leu Tyr Val Lys
```

```
                      435                 440                 445
Gly Glu Pro Ile Ile Asn Phe Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 48
<211> LENGTH: 528
<212> TYPE: PRT
<213> ORGANISM: Artificial Sequence
<220> FEATURE:
<223> OTHER INFORMATION: A2_F24 N67I+S215P+S46G: A2, linker stabilized,
      fibritin

<400> SEQUENCE: 48

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270
```

```
Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
                355                 360                 365

Tyr Asp Cys Lys Ile Met Thr Ser Lys Thr Asp Val Ser Ser Ser Val
            370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 49
<211> LENGTH: 528
<212> TYPE: PRT
<213> ORGANISM: Artificial Sequence
<220> FEATURE:
<223> OTHER INFORMATION: A2_F24: RSV S46G A2, linker stabilized,
      fibritin

<400> SEQUENCE: 49

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Gly Ala Leu
            35                  40                  45

Arg Thr Gly Trp Tyr Thr Ser Val Ile Thr Ile Glu Leu Ser Asn Ile
        50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
                100                 105                 110
```

-continued

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
                180                 185                 190

Ser Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
        210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 50
<211> LENGTH: 528
<212> TYPE: PRT
<213> ORGANISM: Artificial Sequence
<220> FEATURE:
<223> OTHER INFORMATION: A2_F24: RSV K465Q A2, linker stabilized, fibritin

<400> SEQUENCE: 50

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Ser Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365
```

```
Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Gln Ser Leu Tyr Val Lys
                435                 440                 445

Gly Glu Pro Ile Ile Asn Phe Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
        515                 520                 525

<210> SEQ ID NO 51
<211> LENGTH: 528
<212> TYPE: PRT
<213> ORGANISM: Artificial Sequence
<220> FEATURE:
<223> OTHER INFORMATION: A2_F24: RSV N67I A2, linker stabilized,
      fibritin

<400> SEQUENCE: 51

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
                100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
        130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
                180                 185                 190

Ser Asn Ile Glu Thr Val Ile Glu Phe Gln Gln Lys Asn Asn Arg Leu
```

```
            195                 200                 205
Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                    245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Leu Tyr Gly Val Ile Asp
                275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
                355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
                435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
                515                 520                 525
```

<210> SEQ ID NO 52
<211> LENGTH: 528
<212> TYPE: PRT
<213> ORGANISM: Artificial Sequence
<220> FEATURE:
<223> OTHER INFORMATION: A2_F24: RSV E92D A2, linker stabilized, fibritin

<400> SEQUENCE: 52

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30
```

```
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
 50                  55                  60
Lys Lys Asn Lys Cys Asn Gly Thr Asp Ala Lys Ile Lys Leu Ile Lys
 65                  70                  75                  80
Gln Glu Leu Asp Lys Tyr Lys Asn Ala Val Thr Asp Leu Gln Leu Leu
                 85                  90                  95
Met Gln Ser Thr Pro Ala Thr Asn Asn Gln Ala Arg Gly Ser Gly Ser
            100                 105                 110
Gly Arg Ser Leu Gly Phe Leu Leu Gly Val Gly Ser Ala Ile Ala Ser
            115                 120                 125
Gly Val Ala Val Ser Lys Val Leu His Leu Glu Gly Glu Val Asn Lys
130                 135                 140
Ile Lys Ser Ala Leu Leu Ser Thr Asn Lys Ala Val Val Ser Leu Ser
145                 150                 155                 160
Asn Gly Val Ser Val Leu Thr Ser Lys Val Leu Asp Leu Lys Asn Tyr
                165                 170                 175
Ile Asp Lys Gln Leu Leu Pro Ile Val Asn Lys Gln Ser Cys Ser Ile
            180                 185                 190
Ser Asn Ile Glu Thr Val Ile Glu Phe Gln Gln Lys Asn Asn Arg Leu
            195                 200                 205
Leu Glu Ile Thr Arg Glu Phe Ser Val Asn Ala Gly Val Thr Thr Pro
            210                 215                 220
Val Ser Thr Tyr Met Leu Thr Asn Ser Glu Leu Leu Ser Leu Ile Asn
225                 230                 235                 240
Asp Met Pro Ile Thr Asn Asp Gln Lys Lys Leu Met Ser Asn Asn Val
                245                 250                 255
Gln Ile Val Arg Gln Gln Ser Tyr Ser Ile Met Ser Ile Ile Lys Glu
            260                 265                 270
Glu Val Leu Ala Tyr Val Val Gln Leu Pro Leu Tyr Gly Val Ile Asp
            275                 280                 285
Thr Pro Cys Trp Lys Leu His Thr Ser Pro Leu Cys Thr Thr Asn Thr
            290                 295                 300
Lys Glu Gly Ser Asn Ile Cys Leu Thr Arg Thr Asp Arg Gly Trp Tyr
305                 310                 315                 320
Cys Asp Asn Ala Gly Ser Val Ser Phe Phe Pro Gln Ala Glu Thr Cys
                325                 330                 335
Lys Val Gln Ser Asn Arg Val Phe Cys Asp Thr Met Asn Ser Leu Thr
            340                 345                 350
Leu Pro Ser Glu Val Asn Leu Cys Asn Val Asp Ile Phe Asn Pro Lys
            355                 360                 365
Tyr Asp Cys Lys Ile Met Thr Ser Lys Thr Asp Val Ser Ser Ser Val
            370                 375                 380
Ile Thr Ser Leu Gly Ala Ile Val Ser Cys Tyr Gly Lys Thr Lys Cys
385                 390                 395                 400
Thr Ala Ser Asn Lys Asn Arg Gly Ile Ile Lys Thr Phe Ser Asn Gly
                405                 410                 415
Cys Asp Tyr Val Ser Asn Lys Gly Val Asp Thr Val Ser Val Gly Asn
            420                 425                 430
Thr Leu Tyr Tyr Val Asn Lys Gln Glu Gly Lys Ser Leu Tyr Val Lys
            435                 440                 445
Gly Glu Pro Ile Ile Asn Phe Tyr Asp Pro Leu Val Phe Pro Ser Asp
```

```
                        450                 455                 460
Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
            515                 520                 525
```

<210> SEQ ID NO 53
<211> LENGTH: 228
<212> TYPE: PRT
<213> ORGANISM: Artificial Sequence
<220> FEATURE:
<223> OTHER INFORMATION: CR9501 heavy chain

<400> SEQUENCE: 53

```
Gln Val Gln Leu Val Gln Ser Gly Pro Gly Leu Val Lys Pro Ser Gln
1               5                   10                  15

Thr Leu Ala Leu Thr Cys Asn Val Ser Gly Ala Ser Ile Asn Ser Asp
            20                  25                  30

Asn Tyr Tyr Trp Thr Trp Ile Arg Gln Arg Pro Gly Gly Gly Leu Glu
        35                  40                  45

Trp Ile Gly His Ile Ser Tyr Thr Gly Asn Thr Tyr Tyr Thr Pro Ser
50                  55                  60

Leu Lys Ser Arg Leu Ser Met Ser Leu Glu Thr Ser Gln Ser Gln Phe
65                  70                  75                  80

Ser Leu Arg Leu Thr Ser Val Thr Ala Ala Asp Ser Ala Val Tyr Phe
                85                  90                  95

Cys Ala Ala Cys Gly Ala Tyr Val Leu Ile Ser Asn Cys Gly Trp Phe
            100                 105                 110

Asp Ser Trp Gly Gln Gly Thr Gln Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys
225
```

<210> SEQ ID NO 54
<211> LENGTH: 12
<212> TYPE: PRT
<213> ORGANISM: Artificial Sequence
<220> FEATURE:
<223> OTHER INFORMATION: CR9501 VH CDR1

<400> SEQUENCE: 54

```
Gly Ala Ser Ile Asn Ser Asp Asn Tyr Tyr Trp Thr
1               5                   10
```

<210> SEQ ID NO 55
<211> LENGTH: 16
<212> TYPE: PRT
<213> ORGANISM: Artificial Sequence
<220> FEATURE:
<223> OTHER INFORMATION: CR9501 VH CDR2

<400> SEQUENCE: 55

```
His Ile Ser Tyr Thr Gly Asn Thr Tyr Tyr Thr Pro Ser Leu Lys Ser
1               5                   10                  15
```

<210> SEQ ID NO 56
<211> LENGTH: 15
<212> TYPE: PRT
<213> ORGANISM: Artificial Sequence
<220> FEATURE:
<223> OTHER INFORMATION: CR9501 VH CDR3

<400> SEQUENCE: 56

```
Cys Gly Ala Tyr Val Leu Ile Ser Asn Cys Gly Trp Phe Asp Ser
1               5                   10                  15
```

<210> SEQ ID NO 57
<211> LENGTH: 214
<212> TYPE: PRT
<213> ORGANISM: Artificial Sequence
<220> FEATURE:
<223> OTHER INFORMATION: CR9502 heavy chain

<400> SEQUENCE: 57

```
Glu Ile Val Met Thr Gln Ser Pro Ser Ser Leu Ser Ala Ser Ile Gly
1               5                   10                  15

Asp Arg Val Thr Ile Thr Cys Gln Ala Ser Gln Asp Ile Ser Thr Tyr
            20                  25                  30

Leu Asn Trp Tyr Gln Gln Lys Pro Gly Gln Ala Pro Arg Leu Leu Ile
        35                  40                  45

Tyr Gly Ala Ser Asn Leu Glu Thr Gly Val Pro Ser Arg Phe Thr Gly
    50                  55                  60

Ser Gly Tyr Gly Thr Asp Phe Ser Val Thr Ile Ser Ser Leu Gln Pro
65                  70                  75                  80

Glu Asp Ile Ala Thr Tyr Tyr Cys Gln Gln Tyr Gln Tyr Leu Pro Tyr
                85                  90                  95

Thr Phe Ala Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

```
<210> SEQ ID NO 58
<211> LENGTH: 10
<212> TYPE: PRT
<213> ORGANISM: Artificial Sequence
<220> FEATURE:
<223> OTHER INFORMATION: CR9502 VH CDR1

<400> SEQUENCE: 58

Gly Phe Thr Phe Ser Gly His Thr Ile Ala
1               5                   10

<210> SEQ ID NO 59
<211> LENGTH: 17
<212> TYPE: PRT
<213> ORGANISM: Artificial Sequence
<220> FEATURE:
<223> OTHER INFORMATION: CR9502 VH CDR2

<400> SEQUENCE: 59

Trp Val Ser Thr Asn Asn Gly Asn Thr Glu Tyr Ala Gln Lys Ile Gln
1               5                   10                  15

Gly

<210> SEQ ID NO 60
<211> LENGTH: 12
<212> TYPE: PRT
<213> ORGANISM: Artificial Sequence
<220> FEATURE:
<223> OTHER INFORMATION: CR9502 VH CDR3

<400> SEQUENCE: 60

Glu Trp Leu Val Met Gly Gly Phe Ala Phe Asp His
1               5                   10

<210> SEQ ID NO 61
<211> LENGTH: 214
<212> TYPE: PRT
<213> ORGANISM: Artificial Sequence
<220> FEATURE:
<223> OTHER INFORMATION: CR9501 light chain

<400> SEQUENCE: 61

Glu Ile Val Met Thr Gln Ser Pro Ser Ser Leu Ser Ala Ser Ile Gly
1               5                   10                  15

Asp Arg Val Thr Ile Thr Cys Gln Ala Ser Gln Asp Ile Ser Thr Tyr
            20                  25                  30

Leu Asn Trp Tyr Gln Gln Lys Pro Gly Gln Ala Pro Arg Leu Leu Ile
        35                  40                  45

Tyr Gly Ala Ser Asn Leu Glu Thr Gly Val Pro Ser Arg Phe Thr Gly
    50                  55                  60

Ser Gly Tyr Gly Thr Asp Phe Ser Val Thr Ile Ser Ser Leu Gln Pro
65                  70                  75                  80

Glu Asp Ile Ala Thr Tyr Tyr Cys Gln Gln Tyr Gln Tyr Leu Pro Tyr
                85                  90                  95

Thr Phe Ala Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 62
<211> LENGTH: 11
<212> TYPE: PRT
<213> ORGANISM: Artificial Sequence
<220> FEATURE:
<223> OTHER INFORMATION: CR9501 VL CDR1

<400> SEQUENCE: 62

```
Gln Ala Ser Gln Asp Ile Ser Thr Tyr Leu Asn
1               5                   10
```

<210> SEQ ID NO 63
<211> LENGTH: 7
<212> TYPE: PRT
<213> ORGANISM: Artificial Sequence
<220> FEATURE:
<223> OTHER INFORMATION: CR9501 VL CDR2

<400> SEQUENCE: 63

```
Gly Ala Ser Asn Leu Glu Thr
1               5
```

<210> SEQ ID NO 64
<211> LENGTH: 9
<212> TYPE: PRT
<213> ORGANISM: Artificial Sequence
<220> FEATURE:
<223> OTHER INFORMATION: CR9501 VL CDR3

<400> SEQUENCE: 64

```
Gln Gln Tyr Gln Tyr Leu Pro Tyr Thr
1               5
```

<210> SEQ ID NO 65
<211> LENGTH: 215
<212> TYPE: PRT
<213> ORGANISM: Artificial Sequence
<220> FEATURE:
<223> OTHER INFORMATION: CR9502 light chain

<400> SEQUENCE: 65

```
Gln Ser Val Leu Thr Gln Ala Ser Ser Val Ser Ala Pro Gly Gln
1               5                   10                  15

Thr Ala Arg Ile Thr Cys Gly Ala Asn Asn Ile Gly Ser Gln Asn Val
            20                  25                  30

His Trp Tyr Gln Gln Lys Pro Gly Gln Ala Pro Val Leu Val Val Tyr
        35                  40                  45

Asp Asp Arg Asp Arg Pro Ser Gly Ile Pro Asp Arg Phe Ser Gly Ser
    50                  55                  60

Asn Ser Gly Asn Thr Ala Thr Leu Thr Ile Ser Arg Val Glu Ala Gly
65                  70                  75                  80
```

```
Asp Glu Ala Asp Tyr Tyr Cys Gln Val Trp Asp Ser Ser Arg Asp Gln
                85                  90                  95

Ala Val Ile Phe Gly Gly Gly Thr Lys Leu Thr Val Leu Gly Gln Pro
        100                 105                 110

Lys Ala Ala Pro Ser Val Thr Leu Phe Pro Pro Ser Ser Glu Glu Leu
    115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Ile Ala Pro Thr Glu Cys Ser
    210                 215

<210> SEQ ID NO 66
<211> LENGTH: 11
<212> TYPE: PRT
<213> ORGANISM: Artificial Sequence
<220> FEATURE:
<223> OTHER INFORMATION: CR9502 VL CDR1

<400> SEQUENCE: 66

Gly Ala Asn Asn Ile Gly Ser Gln Asn Val His
1               5                   10

<210> SEQ ID NO 67
<211> LENGTH: 7
<212> TYPE: PRT
<213> ORGANISM: Artificial Sequence
<220> FEATURE:
<223> OTHER INFORMATION: CR9502 VL CDR2

<400> SEQUENCE: 67

Asp Asp Arg Asp Arg Pro Ser
1               5

<210> SEQ ID NO 68
<211> LENGTH: 12
<212> TYPE: PRT
<213> ORGANISM: Artificial Sequence
<220> FEATURE:
<223> OTHER INFORMATION: CR9502 VL CDR3

<400> SEQUENCE: 68

Gln Val Trp Asp Ser Ser Arg Asp Gln Ala Val Ile
1               5                   10

<210> SEQ ID NO 69
<211> LENGTH: 574
<212> TYPE: PRT
<213> ORGANISM: Artificial Sequence
<220> FEATURE:
<223> OTHER INFORMATION: RSV F protein CL57-v224 full length sequence

<400> SEQUENCE: 69

Met Glu Leu Pro Ile Leu Lys Thr Asn Ala Ile Thr Thr Ile Leu Ala
1               5                   10                  15
```

```
Ala Val Thr Leu Cys Phe Ala Ser Ser Gln Asn Ile Thr Glu Glu Phe
                 20                  25                  30

Tyr Gln Ser Thr Cys Ser Ala Val Ser Lys Gly Tyr Leu Ser Ala Leu
             35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Ala Asn Asn Arg Ala Arg Glu Leu Pro
                100                 105                 110

Arg Phe Met Asn Tyr Thr Leu Asn Asn Thr Lys Asn Asn Val Thr
                115                 120                 125

Leu Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Ser Asn Ile Glu Thr Val Ile Glu Phe Gln
                210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Ile
                370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430
```

```
Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Val Gly Lys Ser Thr Thr Asn Ile Met Ile Thr
            515                 520                 525

Thr Ile Ile Ile Val Ile Ile Val Ile Leu Leu Leu Ile Ala Val
        530                 535                 540

Gly Leu Phe Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 70
<211> LENGTH: 513
<212> TYPE: PRT
<213> ORGANISM: Artificial Sequence
<220> FEATURE:
<223> OTHER INFORMATION: Ectodomain, RSV CL57-v224

<400> SEQUENCE: 70

```
Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220
```

-continued

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu

<210> SEQ ID NO 71
<211> LENGTH: 544
<212> TYPE: PRT
<213> ORGANISM: Artificial Sequence
<220> FEATURE:
<223> OTHER INFORMATION: PreF, RSV A2, fibritin

<400> SEQUENCE: 71

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
```

-continued

```
                65                  70                  75                  80
        Gln Glu Leu Asp Lys Tyr Lys Asn Ala Val Thr Glu Leu Gln Leu Leu
                        85                  90                  95

Met Gln Ser Thr Pro Ala Thr Asn Asn Arg Ala Arg Arg Glu Leu Pro
                        100                 105                 110

Arg Phe Met Asn Tyr Thr Leu Asn Asn Ala Lys Lys Thr Asn Val Thr
                        115                 120                 125

Leu Ser Lys Lys Arg Lys Arg Arg Phe Leu Gly Phe Leu Leu Gly Val
                        130                 135                 140

Gly Ser Ala Ile Ala Ser Gly Val Ala Val Ser Lys Val Leu His Leu
        145                 150                 155                 160

Glu Gly Glu Val Asn Lys Ile Lys Ser Ala Leu Leu Ser Thr Asn Lys
                        165                 170                 175

Ala Val Val Ser Leu Ser Asn Gly Val Ser Val Leu Thr Ser Lys Val
                        180                 185                 190

Leu Asp Leu Lys Asn Tyr Ile Asp Lys Gln Leu Leu Pro Ile Val Asn
                        195                 200                 205

Lys Gln Ser Cys Ser Ile Ser Asn Ile Glu Thr Val Ile Glu Phe Gln
                        210                 215                 220

Gln Lys Asn Asn Arg Leu Leu Glu Ile Thr Arg Glu Phe Ser Val Asn
        225                 230                 235                 240

Ala Gly Val Thr Thr Pro Val Ser Thr Tyr Met Leu Thr Asn Ser Glu
                        245                 250                 255

Leu Leu Ser Leu Ile Asn Asp Met Pro Ile Thr Asn Asp Gln Lys Lys
                        260                 265                 270

Leu Met Ser Asn Asn Val Gln Ile Val Arg Gln Gln Ser Tyr Ser Ile
                        275                 280                 285

Met Ser Ile Ile Lys Glu Glu Val Leu Ala Tyr Val Val Gln Leu Pro
                        290                 295                 300

Leu Tyr Gly Val Ile Asp Thr Pro Cys Trp Lys Leu His Thr Ser Pro
        305                 310                 315                 320

Leu Cys Thr Thr Asn Thr Lys Glu Gly Ser Asn Ile Cys Leu Thr Arg
                        325                 330                 335

Thr Asp Arg Gly Trp Tyr Cys Asp Asn Ala Gly Ser Val Ser Phe Phe
                        340                 345                 350

Pro Gln Ala Glu Thr Cys Lys Val Gln Ser Asn Arg Val Phe Cys Asp
                        355                 360                 365

Thr Met Asn Ser Leu Thr Leu Pro Ser Glu Val Asn Leu Cys Asn Val
                        370                 375                 380

Asp Ile Phe Asn Pro Lys Tyr Asp Cys Lys Ile Met Thr Ser Lys Thr
        385                 390                 395                 400

Asp Val Ser Ser Ser Val Ile Thr Ser Leu Gly Ala Ile Val Ser Cys
                        405                 410                 415

Tyr Gly Lys Thr Lys Cys Thr Ala Ser Asn Lys Asn Arg Gly Ile Ile
                        420                 425                 430

Lys Thr Phe Ser Asn Gly Cys Asp Tyr Val Ser Asn Lys Gly Val Asp
                        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
                        465                 470                 475                 480

Leu Val Phe Pro Ser Asp Glu Phe Asp Ala Ser Ile Ser Gln Val Asn
                        485                 490                 495
```

```
Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

<210> SEQ ID NO 72
<211> LENGTH: 544
<212> TYPE: PRT
<213> ORGANISM: Artificial Sequence
<220> FEATURE:
<223> OTHER INFORMATION: PreF N67I S215P, RSV A2, fibritin

<400> SEQUENCE: 72

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320
```

```
Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

<210> SEQ ID NO 73
<211> LENGTH: 544
<212> TYPE: PRT
<213> ORGANISM: Artificial Sequence
<220> FEATURE:
<223> OTHER INFORMATION: PreF N67I S215P, RSV B1, fibritin

<400> SEQUENCE: 73

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140
```

```
Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Pro Asn Ile Glu Thr Val Ile Glu Phe Gln
210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Ser Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Asp Thr Cys Lys Val Gln Ser Asn Arg Val Phe Cys Asp
355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
        500                 505                 510

Leu Ser Ala Ile Gly Gly Tyr Ile Pro Glu Ala Pro Arg Asp Gly Gln
    515                 520                 525

Ala Tyr Val Arg Lys Asp Gly Glu Trp Val Leu Leu Ser Thr Phe Leu
    530                 535                 540

<210> SEQ ID NO 74
<211> LENGTH: 544
```

```
<212> TYPE: PRT
<213> ORGANISM: Artificial Sequence
<220> FEATURE:
<223> OTHER INFORMATION: RSV N67I S215P, RSV CL57-v224, fibritin

<400> SEQUENCE: 74
```

| | | | | | | | | | |

```
Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
530                 535                 540
```

<210> SEQ ID NO 75
<211> LENGTH: 522
<212> TYPE: PRT
<213> ORGANISM: Artificial Sequence
<220> FEATURE:
<223> OTHER INFORMATION: PreFL N67I S215P, RSV CL57-v224, fibritin, Loop

<400> SEQUENCE: 75

```
Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Ser Thr Pro Ala Ala Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Ile Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
            165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
            195                 200                 205
```

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Ile Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu
    515                 520

<210> SEQ ID NO 76
<211> LENGTH: 544
<212> TYPE: PRT
<213> ORGANISM: Artificial Sequence
<220> FEATURE:
<223> OTHER INFORMATION: PreF N67I S215P E487Q, RSV A2, fibritin

<400> SEQUENCE: 76

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

-continued

Arg Thr Gly Trp Tyr Thr Ser Val Ile Thr Ile Glu Leu Ser Asn Ile
    50              55                  60

Lys Lys Ile Lys Cys Asn Gly Thr Asp Ala Lys Ile Lys Leu Ile Lys
65              70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro

```
                465                 470                 475                 480
Leu Val Phe Pro Ser Asp Gln Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
                530                 535                 540

<210> SEQ ID NO 77
<211> LENGTH: 544
<212> TYPE: PRT
<213> ORGANISM: Artificial Sequence
<220> FEATURE:
<223> OTHER INFORMATION: PreF N67I S215P K201N, RSV A2, fibritin

<400> SEQUENCE: 77

Met Glu Leu Leu Ile Leu Lys Ala Asn Ala Ile Thr Thr Ile Leu Thr
 1               5                  10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
                50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Arg Lys Arg Arg Phe Leu Gly Phe Leu Leu Gly Val
                130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Asn Gln Leu Leu Pro Ile Val Asn
                195                 200                 205

Lys Gln Ser Cys Ser Ile Pro Asn Ile Glu Thr Val Ile Glu Phe Gln
                210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
```

-continued

```
                290                 295                 300
Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
                370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
                530                 535                 540
```

<210> SEQ ID NO 78
<211> LENGTH: 544
<212> TYPE: PRT
<213> ORGANISM: Artificial Sequence
<220> FEATURE:
<223> OTHER INFORMATION: PreF N67I S215P E92D, RSV A2, fibritin

<400> SEQUENCE: 78

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
```

```
            115                 120                 125
Leu Ser Lys Lys Arg Lys Arg Arg Phe Leu Gly Phe Leu Leu Gly Val
            130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asp Lys Gln Leu Leu Pro Ile Val Asn
            195                 200                 205
Lys Gln Ser Cys Ser Ile Pro Asn Ile Glu Thr Val Ile Glu Phe Gln
    210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
            275                 280                 285
Met Ser Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
            370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Gln Glu Gly
            450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
                500                 505                 510
Leu Ser Ala Ile Gly Gly Tyr Ile Pro Glu Ala Pro Arg Asp Gly Gln
            515                 520                 525
Ala Tyr Val Arg Lys Asp Gly Glu Trp Val Leu Leu Ser Thr Phe Leu
530                 535                 540
```

<210> SEQ ID NO 79
<211> LENGTH: 544
<212> TYPE: PRT
<213> ORGANISM: Artificial Sequence
<220> FEATURE:
<223> OTHER INFORMATION: PreF N67I S215P D486N, RSV A2, fibritin

<400> SEQUENCE: 79

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365
```

```
Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asn Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
530                 535                 540
```

```
<210> SEQ ID NO 80
<211> LENGTH: 574
<212> TYPE: PRT
<213> ORGANISM: Artificial Sequence
<220> FEATURE:
<223> OTHER INFORMATION: Fwt N67I S215P, membrane-bound RSV F, A2

<400> SEQUENCE: 80
```

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190
```

Leu Asp Leu Lys Asn Tyr Ile Asp Lys Gln Leu Leu Pro Ile Val Asn
            195                 200                 205

Lys Gln Ser Cys Ser Ile Pro Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
        515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 81
<211> LENGTH: 552
<212> TYPE: PRT
<213> ORGANISM: Artificial Sequence
<220> FEATURE:

<223> OTHER INFORMATION: Fs1 N67I S215P, membrane-bound RSV F, A2

<400> SEQUENCE: 81

```

```
Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
                485                 490                 495

Val Lys Ser Thr Thr Asn Ile Met Ile Thr Thr Ile Ile Ile Val Ile
            500                 505                 510

Ile Val Ile Leu Leu Ser Leu Ile Ala Val Gly Leu Leu Leu Tyr Cys
        515                 520                 525

Lys Ala Arg Ser Thr Pro Val Thr Leu Ser Lys Asp Gln Leu Ser Gly
530                 535                 540

Ile Asn Asn Ile Ala Phe Ser Asn
545                 550
```

<210> SEQ ID NO 82
<211> LENGTH: 574
<212> TYPE: PRT
<213> ORGANISM: Artificial Sequence
<220> FEATURE:
<223> OTHER INFORMATION: Fwt N67I S215P E92D, membrane-bound RSV F, A2

<400> SEQ

```
Lys Gln Ser Cys Ser Ile Pro Asn Ile Glu Thr Val Ile Glu Phe Gln
    210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
            245                 250                 255
Leu Leu Ser Leu Ile Asn Asp Met Pro Ile Thr Asn Asp Gln Lys Lys
        260                 265                 270
Leu Met Ser Asn Asn Val Gln Ile Val Arg Gln Gln Ser Tyr Ser Ile
    275                 280                 285
Met Ser Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
            325                 330                 335
Thr Asp Arg Gly Trp Tyr Cys Asp Asn Ala Gly Ser Val Ser Phe Phe
        340                 345                 350
Pro Gln Ala Glu Thr Cys Lys Val Gln Ser Asn Arg Val Phe Cys Asp
    355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
            405                 410                 415
Tyr Gly Lys Thr Lys Cys Thr Ala Ser Asn Lys Asn Arg Gly Ile Ile
        420                 425                 430
Lys Thr Phe Ser Asn Gly Cys Asp Tyr Val Ser Asn Lys Gly Val Asp
    435                 440                 445
Thr Val Ser Val Gly Asn Thr Leu Tyr Tyr Val Asn Lys Gln Glu Gly
450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
            485                 490                 495
Glu Lys Ile Asn Gln Ser Leu Ala Phe Ile Arg Lys Ser Asp Glu Leu
        500                 505                 510
Leu His Asn Val Asn Ala Val Lys Ser Thr Thr Asn Ile Met Ile Thr
    515                 520                 525
Thr Ile Ile Ile Val Ile Ile Val Ile Leu Leu Ser Leu Ile Ala Val
530                 535                 540
Gly Leu Leu Leu Tyr Cys Lys Ala Arg Ser Thr Pro Val Thr Leu Ser
545                 550                 555                 560
Lys Asp Gln Leu Ser Gly Ile Asn Asn Ile Ala Phe Ser Asn
            565                 570

<210> SEQ ID NO 83
<211> LENGTH: 552
<212> TYPE: PRT
<213> ORGANISM: Artificial Sequence
<220> FEATURE:
<223> OTHER INFORMATION: Fs1 N67I S215P E92D, membrane-bound RSV F, A2

<400> SEQUENCE: 83
```

```
Met Glu Leu Leu Ile Leu Lys Ala Asn Ala Ile Thr Thr Ile Leu Thr
 1               5                  10                  15

Ala Val Thr Phe Cys Phe Ala Ser Gly Gln Asn Ile Thr Glu Glu Phe
             20                  25                  30

Tyr Gln Ser Thr Cys Ser Ala Val Ser Lys Gly Tyr Leu Ser Ala Leu
             35                  40                  45

Arg Thr Gly Trp Tyr Thr Ser Val Ile Thr Ile Glu Leu Ser Asn Ile
     50                  55                  60

Lys Lys Ile Lys Cys Asn Gly Thr Asp Ala Lys Ile Lys Leu Ile Lys
 65                  70                  75                  80

Gln Glu Leu Asp Lys Tyr Lys Asn Ala Val Thr Asp Leu Gln Leu Leu
                 85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
        130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
        210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
```

-continued

```
                420             425             430
Thr Leu Tyr Tyr Val Asn Lys Gln Glu Gly Lys Ser Leu Tyr Val Lys
            435             440             445

Gly Glu Pro Ile Ile Asn Phe Tyr Asp Pro Leu Val Phe Pro Ser Asp
            450             455             460

Glu Phe Asp Ala Ser Ile Ser Gln Val Asn Glu Lys Ile Asn Gln Ser
465             470             475             480

Leu Ala Phe Ile Arg Lys Ser Asp Glu Leu Leu His Asn Val Asn Ala
            485             490             495

Val Lys Ser Thr Thr Asn Ile Met Ile Thr Thr Ile Ile Ile Val Ile
            500             505             510

Ile Val Ile Leu Leu Ser Leu Ile Ala Val Gly Leu Leu Leu Tyr Cys
            515             520             525

Lys Ala Arg Ser Thr Pro Val Thr Leu Ser Lys Asp Gln Leu Ser Gly
            530             535             540

Ile Asn Asn Ile Ala Phe Ser Asn
545             550
```

<210> SEQ ID NO 84
<211> LENGTH: 574
<212> TYPE: PRT
<213> ORGANISM: Artificial Sequence
<220> FEATURE:
<223> OTHER INFORMATION: Fwt N67I S215P E487Q, membrane-bound RSV F, A2

<400> SEQUENCE: 84

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65              70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145             150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Pro Asn Ile Glu Thr Val Ile Glu Phe Gln
        210                 215                 220

Gln Lys Asn Asn Arg Leu Leu Glu Ile Thr Arg Glu Phe Ser Val Asn
```

| | | 225 | | | 230 | | | 235 | | | 240 |

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Gln Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
            515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 85
<211> LENGTH: 552
<212> TYPE: PRT
<213> ORGANISM: Artificial Sequence
<220> FEATURE:
<223> OTHER INFORMATION: Fsl N67I S215P E487Q, membrane-bound RSV F, A2

<400> SEQUENCE: 85

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe

```
                    20                  25                  30
Tyr Gln Ser Thr Cys Ser Ala Val Ser Lys Gly Tyr Leu Ser Ala Leu
                35                  40                  45
Arg Thr Gly Trp Tyr Thr Ser Val Ile Thr Ile Glu Leu Ser Asn Ile
            50                  55                  60
Lys Lys Ile Lys Cys Asn Gly Thr Asp Ala Lys Ile Lys Leu Ile Lys
 65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Gln Ala Arg Gly Ser Gly Ser
            100                 105                 110
Gly Arg Ser Leu Gly Phe Leu Leu Gly Val Gly Ser Ala Ile Ala Ser
            115                 120                 125
Gly Val Ala Val Ser Lys Val Leu His Leu Glu Gly Glu Val Asn Lys
            130                 135                 140
Ile Lys Ser Ala Leu Leu Ser Thr Asn Lys Ala Val Val Ser Leu Ser
145                 150                 155                 160
Asn Gly Val Ser Val Leu Thr Ser Lys Val Leu Asp Leu Lys Asn Tyr
                165                 170                 175
Ile Asp Lys Gln Leu Leu Pro Ile Val Asn Lys Gln Ser Cys Ser Ile
            180                 185                 190
Pro Asn Ile Glu Thr Val Ile Glu Phe Gln Gln Lys Asn Asn Arg Leu
            195                 200                 205
Leu Glu Ile Thr Arg Glu Phe Ser Val Asn Ala Gly Val Thr Thr Pro
            210                 215                 220
Val Ser Thr Tyr Met Leu Thr Asn Ser Glu Leu Leu Ser Leu Ile Asn
225                 230                 235                 240
Asp Met Pro Ile Thr Asn Asp Gln Lys Lys Leu Met Ser Asn Asn Val
                245                 250                 255
Gln Ile Val Arg Gln Gln Ser Tyr Ser Ile Met Ser Ile Ile Lys Glu
            260                 265                 270
Glu Val Leu Ala Tyr Val Val Gln Leu Pro Leu Tyr Gly Val Ile Asp
            275                 280                 285
Thr Pro Cys Trp Lys Leu His Thr Ser Pro Leu Cys Thr Thr Asn Thr
            290                 295                 300
Lys Glu Gly Ser Asn Ile Cys Leu Thr Arg Thr Asp Arg Gly Trp Tyr
305                 310                 315                 320
Cys Asp Asn Ala Gly Ser Val Ser Phe Phe Pro Gln Ala Glu Thr Cys
                325                 330                 335
Lys Val Gln Ser Asn Arg Val Phe Cys Asp Thr Met Asn Ser Leu Thr
            340                 345                 350
Leu Pro Ser Glu Val Asn Leu Cys Asn Val Asp Ile Phe Asn Pro Lys
            355                 360                 365
Tyr Asp Cys Lys Ile Met Thr Ser Lys Thr Asp Val Ser Ser Ser Val
            370                 375                 380
Ile Thr Ser Leu Gly Ala Ile Val Ser Cys Tyr Gly Lys Thr Lys Cys
385                 390                 395                 400
Thr Ala Ser Asn Lys Asn Arg Gly Ile Ile Lys Thr Phe Ser Asn Gly
                405                 410                 415
Cys Asp Tyr Val Ser Asn Lys Gly Val Asp Thr Val Ser Val Gly Asn
            420                 425                 430
Thr Leu Tyr Tyr Val Asn Lys Gln Glu Gly Lys Ser Leu Tyr Val Lys
            435                 440                 445
```

```
Gly Glu Pro Ile Ile Asn Phe Tyr Asp Pro Leu Val Phe Pro Ser Asp
    450                 455                 460

Gln Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
                485                 490                 495

Val Lys Ser Thr Thr Asn Ile Met Ile Thr Thr Ile Ile Ile Val Ile
            500                 505                 510

Ile Val Ile Leu Leu Ser Leu Ile Ala Val Gly Leu Leu Leu Tyr Cys
        515                 520                 525

Lys Ala Arg Ser Thr Pro Val Thr Leu Ser Lys Asp Gln Leu Ser Gly
    530                 535                 540

Ile Asn Asn Ile Ala Phe Ser Asn
545                 550

<210> SEQ ID NO 86
<211> LENGTH: 574
<212> TYPE: PRT
<213> ORGANISM: Artificial Sequence
<220> FEATURE:
<223> OTHER INFORMATION: Fwt N67I S215P D486N, membrane-bound RSV F, A2

<400> SEQUENCE: 86

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255
```

```
Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asn Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
        515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 87
<211> LENGTH: 552
<212> TYPE: PRT
<213> ORGANISM: Artificial Sequence
<220> FEATURE:
<223> OTHER INFORMATION: Fs1 N67I S215P D486N, membrane-bound RSV F, A2

<400> SEQUENCE: 87

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

-continued

```
Arg Thr Gly Trp Tyr Thr Ser Val Ile Thr Ile Glu Leu Ser Asn Ile
     50                  55                  60

Lys Lys Ile Lys Cys Asn Gly Thr Asp Ala Lys Ile Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asn
450                 455                 460
```

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
            485                 490                 495

Val Lys Ser Thr Thr Asn Ile Met Ile Thr Thr Ile Ile Ile Val Ile
        500                 505                 510

Ile Val Ile Leu Leu Ser Leu Ile Ala Val Gly Leu Leu Leu Tyr Cys
    515                 520                 525

Lys Ala Arg Ser Thr Pro Val Thr Leu Ser Lys Asp Gln Leu Ser Gly
    530                 535                 540

Ile Asn Asn Ile Ala Phe Ser Asn
545                 550

<210> SEQ ID NO 88
<211> LENGTH: 574
<212> TYPE: PRT
<213> ORGANISM: Artificial Sequence
<220> FEATURE:
<223> OTHER INFORMATION: Fwt N67I S215P S46G, membrane-bound RSV F, A2

<400> SEQUENCE: 88

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

```
Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
            515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570
```

<210> SEQ ID NO 89
<211> LENGTH: 552
<212> TYPE: PRT
<213> ORGANISM: Artificial Sequence
<220> FEATURE:
<223> OTHER INFORMATION: Fs1 N67I S215P S46G, membrane-bound R

```
Lys Lys Ile Lys Cys Asn Gly Thr Asp Ala Lys Ile Lys Leu Ile Lys
 65                  70                  75                  80

Gln Glu Leu Asp Lys Tyr Lys Asn Ala Val Thr Glu Leu Gln Leu Leu
             85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
            130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
            245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
            290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
```

```
              485                 490                 495
Val Lys Ser Thr Thr Asn Ile Met Ile Thr Thr Ile Ile Ile Val Ile
            500                 505                 510

Ile Val Ile Leu Leu Ser Leu Ile Ala Val Gly Leu Leu Leu Tyr Cys
            515                 520                 525

Lys Ala Arg Ser Thr Pro Val Thr Leu Ser Lys Asp Gln Leu Ser Gly
            530                 535                 540

Ile Asn Asn Ile Ala Phe Ser Asn
545                 550

<210> SEQ ID NO 90
<211> LENGTH: 529
<212> TYPE: PRT
<213> ORGANISM: Artificial Sequence
<220> FEATURE:
<223> OTHER INFORMATION: AAA47881PIV5

<400> SEQUENCE: 90

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
```

```
            290                 295                 300
Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Thr Met Ala Cys Leu Gln Gly Asn
                340                 345                 350

Leu Thr Arg Cys Thr Phe Ser Pro Val Val Gly Ser Phe Leu Thr Arg
                355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
                420                 425                 430

Thr Ile Lys Leu Glu Ser Ser Gln Ile Leu Ser Ile Asp Pro Leu Asp
                435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Trp Lys Leu Leu
                500                 505                 510

Thr Ile Val Val Ala Asn Arg Asn Arg Met Glu Asn Phe Val Tyr His
                515                 520                 525

Lys

<210> SEQ ID NO 91
<211> LENGTH: 574
<212> TYPE: PRT
<213> ORGANISM: Artificial Sequence
<220> FEATURE:
<223> OTHER INFORMATION: FUS_HRSV1B

<400> SEQUENCE: 91

Met Glu Leu Leu Ile His Arg Ser Ser Ala Ile Phe Leu Thr Leu Ala
1               5                   10                  15

Val Asn Ala Leu Tyr Leu Th

```
Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asn Asn Arg Leu Leu Pro Ile Val Asn
            195                 200                 205

Gln Gln Ser Cys Arg Ile Ser Asn Ile Glu Thr Val Ile Glu Phe Gln
210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
530                 535                 540
```

```
Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

<210> SEQ ID NO 92
<211> LENGTH: 454
<212> TYPE: PRT
<213> ORGANISM: Artificial Sequence
<220> FEATURE:
<223> OTHER INFORMATION: ACO83301HRSVA2ref

<400> SEQUENCE: 92

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335
```

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ile Val Ile Ile Val
                405                 410                 415

Ile Leu Leu Ser Leu Ile Ala Val Gly Leu Leu Leu Tyr Cys Lys Ala
            420                 425                 430

Arg Ser Thr Pro Val Thr Leu Ser Lys Asp Gln Leu Ser Gly Ile Asn
            435                 440                 445

Asn Ile Ala Phe Ser Asn
    450

<210> SEQ ID NO 93
<211> LENGTH: 45
<212> TYPE: PRT
<213> ORGANISM: Artificial Sequence
<220> FEATURE:
<223> OTHER INFORMATION: artificial sequence

<400> SEQUENCE: 93

Pro Ala Ala Asn Asn Arg Ala Arg Arg Glu Ala Pro Gln Tyr Met Asn
1               5                   10                  15

Tyr Thr Ile Asn Thr Thr Lys Asn Leu Asn Val Ser Ile Ser Lys Lys
            20                  25                  30

Arg Lys Arg Arg Phe Leu Gly Phe Leu Leu Gly Val Gly
        35                  40                  45

<210> SEQ ID NO 94
<211> LENGTH: 23
<212> TYPE: PRT
<213> ORGANISM: Artificial Sequence
<220> FEATURE:
<223> OTHER INFORMATION: modified sequence

<400> SEQUENCE: 94

Pro Ala Ala Asn Asn Gln Ala Arg Gly Ser Gly Ser Gly Arg Ser Leu
1               5                   10                  15

Gly Phe Leu Leu Gly Val Gly
            20

<210> SEQ ID NO 95
<211> LENGTH: 63
<212> TYPE: PRT
<213> ORGANISM: Artificial Sequence
<220> FEATURE:
<223> OTHER INFORMATION: sequence of residues 150 - 212 of RSV-F is

<400> SEQUENCE: 95

Ser Gly Val Ala Val Ser Lys Val Leu His Leu Glu Gly Glu Val Asn
1               5                   10                  15

Lys Ile Lys Ser Ala Leu Leu Ser Thr Asn Lys Ala Val Val Ser Leu
            20                  25                  30

Ser Asn Gly Val Ser Val Leu Thr Ser Lys Val Leu Asp Leu Lys Asn
        35                  40                  45

Tyr Ile Asp Lys Gln Leu Leu Pro Ile Val Asn Lys Gln Ser Cys

```
<210> SEQ ID NO 96
<211> LENGTH: 15
<212> TYPE: PRT
<213> ORGANISM: Artificial Sequence
<220> FEATURE:
<223> OTHER INFORMATION: HRAb1b2 178-192

<400> SEQUENCE: 96

Val Val Ser Leu Ser Asn Gly Val Ser Val Leu Thr Ser Lys Val
1               5                  10                  15

<210> SEQ ID NO 97
<211> LENGTH: 15
<212> TYPE: PRT
<213> ORGANISM: Artificial Sequence
<220> FEATURE:
<223> OTHER INFORMATION: 3fhi:B 179-193

<400> SEQUENCE: 97

Glu Met Asp Val Tyr Val Asn Asn Glu Trp Ala Thr Ser Val Gly
1               5                  10                  15
```